US006844189B1

(12) United States Patent
Tavtigian et al.

(10) Patent No.: US 6,844,189 B1
(45) Date of Patent: Jan. 18, 2005

(54) CHROMOSOME 17P-LINKED PROSTATE CANCER SUSCEPTIBILITY GENE

(75) Inventors: Sean V. Tavtigian, Salt Lake City, UT (US); David H.-F. Teng, Salt Lake City, UT (US); Jacques Simard, St. Augustin de DesMaures (CA); Johanna M. Rommens, Toronto (CA); Lisa A. Cannon Albright, Salt Lake City, UT (US); Susan L. Neuhausen, Salt Lake City, UT (US)

(73) Assignees: Myriad Genetics, Inc., Salt Lake City, UT (US); University of Utah Research Foundation, Salt Lake City, UT (US); Hospital for Sick Children, Toronto (CA)

( * ) Notice: Subject to any disclaimer, the term of this patent is extended or adjusted under 35 U.S.C. 154(b) by 0 days.

(21) Appl. No.: 09/434,382

(22) Filed: Nov. 5, 1999

Related U.S. Application Data
(60) Provisional application No. 60/107,468, filed on Nov. 6, 1998.

(51) Int. Cl.[7] ........................... C12N 5/16; C12N 15/12; C12N 15/63
(52) U.S. Cl. ..................... 435/325; 435/69.1; 435/70.1; 435/320.1; 536/23.1; 536/23.5
(58) Field of Search ............................... 536/23.1, 23.5, 536/24.3, 24.31, 24.33; 435/69.1, 70.1, 325, 320.1, 91.2, 6

(56) References Cited

U.S. PATENT DOCUMENTS 5,925,519 A    7/1999  Jensen et al. ................... 435/6

OTHER PUBLICATIONS

Verma, et al, Nature, 1997, vol. 389, pp. 239–242.*
Eck, et al, Gene–Based Therapy, In: The Pharmacological Basis of Therapeutics, Goodman and Gilman, Ed.s, 1996, pp. 77–101.*
New England Biolabs (1993/1994 Catalog.*
Ohagi et al., Identification and analysis of teh gene encoding human PC2, a prohormone convertase expressed in neuroendocrine tissues, PNAS, vol. 89, pp. 4977–4981, Jun. 1992.*
Bowie et al., Deciphering the Message in Protein Sequences: Tolerance to Amino Acid Substitutions, Science, vol. 247, pp. 1306–1310, Mar. 1990.*
Burgess et al., Possible Dissociation of the Heparin–binding and Mitogenic Activities of Heparin–binding (Acidic Fibroblast) Growth Factor–1 from It's Receptor–binding Activities by Site–directed Mutagenesis of a Single Lysine Residue, The Journal of Cell, Nov. 1990.*
Lazar et al., Transforming Growth Factor alpha: Mutation of Aspartic Acid 47 and Leucine 48 Results in Different Biological Activities, Molecular and Cellular Biology, pp. 1247–1252, Mar. 1988.*

Bork, Powers and Pitfalls in Sequence Analysis: The 70% Hurdle, Genome Research, pp. 398–400, 2000.*
Cooney, K.A. et al. (1997). "Prostate Cancer Susceptibility Locus on Chromosome 1q: a Confirmatory Study," *J. Natl. Can. Inst.* 89:955–959.
Cooney, K.A. et al. (1998). "Hereditary Prostate Cancer in African–American Families," *Seminars Urologic Oncol.* 16:202–206.
Xu, J. et al. (1998). "Evidence for a prostate cancer susceptibility locus on the X chromosome," *Nature Genet.* 20:175–179.
Database Gencore on EST, No. AC005277, Birren et al., "*Homo sapiens* chromosome 17, clone hRPK.597_M_12, complete sequence," Gene Sequence, Jul. 23, 1998.
Database Gencore on EST, No. N36229,Hillier et al., "yy30c04.sl Soares melanocyte 2NbHM *Homo sapiens* cDNA clone," Gene Sequence, Jul. 16, 1996.
X. Gao, et al., "Loss of Heterozygosity of the *BRCA1* and Other Loci on Chromosone 17q in Human Prostate Cancer," Cancer Research, vol. 55, Mar. 1, 1995, pp. 1002–1005.
C. W. Rinker–Schaeffer, et al., "Differential Suppression of Mammary and Prostate Cancer Metastasis by Human Chromosomes 17 and 11[1]," Cancer Research, vol. 54, Dec. 1, 1994, pp. 6249–6259.
S. V. Tavtigian, "A candidate prostate cancer susceptibility gene at chromosome 17p," Nature Genetics, vol. 27, Feb. 2001, pp. 172–180.

* cited by examiner

Primary Examiner—Alana M. Harris
Assistant Examiner—Anne L. Holleran
(74) Attorney, Agent, or Firm—Jeffrey Ihnen; Herbert L. Ley, III; Jay Z. Zhang

(57) ABSTRACT

The present invention relates generally to the field of human genetics. Specifically, the present invention relates to methods and materials used to isolate and detect a human prostate cancer predisposing gene (HPC2), some alleles of which cause susceptibility to cancer, in particular prostate cancer. More specifically, the present invention relates to germline mutations in the HPC2 gene and their use in the diagnosis of predisposition to prostate cancer. The invention also relates to presymptomatic therapy of individuals who carry deleterious alleles of the HPC2 gene. The invention further relates to somatic mutations in the HPC2 gene in human prostate cancer and their use in the diagnosis and prognosis of human prostate cancer. Additionally, the invention relates to somatic mutations in the HPC2 gene in other human cancers and their use in the diagnosis and prognosis of human cancers. The invention also relates to the therapy of human cancers which have a mutation in the HPC2 gene, (including gene therapy, protein replacement therapy, protein mimetics, and inhibitors). The invention further relates to the screening of drugs for cancer therapy. Finally, the invention relates to the screening of the HPC2 gene for mutations, which are useful for diagnosing the predisposition to prostate cancer.

26 Claims, 4 Drawing Sheets

```
Hs.HPC2.exon1        cgcgggcgtaggtgaccggcggctttctcagttttggtggagacgggcgc
Hs.HPC2.exon1.pep
Mm.HPC2.exon2        tggcggcgtgaggggtctggctgccttgtcagcctggtgtggtcgggtgc
Mm.HPC2.exon1.pep
                     |---------|---------|---------|---------|--------
                     1         11        21        31        41

Hs.HPC2.exon1        ATGTGGGCGCTTTGCTCGCTGCTGCGGTCCGCGGCCGGACGCACCATGTC
Hs.HPC2.exon1.pep    M--W--A--L--C--S--L--L--R--S--A--A--G--R--T--M--S-
Mm.HPC2.exon2        ATGTGGGCGCTCCGCTCACTGTTGCGTCCCCTTGGCCTGCGCACCATGTC
Mm.HPC2.exon1.pep    M--W--A--L--R--S--L--L--R--P--L--G--L--R--T--M--S-
                     |---------|---------|---------|---------|---------
                     51        61        71        81        91

Hs.HPC2.exon1        GCAGGGACGCACCATATCGCAGGCACCCGCCCGCCGCGAGCGGCCGCGCA
Hs.HPC2.exon1.pep    -Q--G--R--T--I--S--Q--A--P--A--R--R--E--R--P--R--K
Mm.HPC2.exon2        GCAGGGT----------------TCGGCTCGTCGGCCGCGGCCACCCA
Mm.HPC2.exon1.pep    -Q--G-----------------S--A--R--R--P--R--P--P--K
                     |---------|---------|---------|---------|---------
                     101       111       121       131       141

Hs.HPC2.exon1        AGGACCCGCTGCGGCACCTGCGCACGCGAGAGAAGCGCGGACCGTCGGGG
Hs.HPC2.exon1.pep    --D--P--L--R--H--L--R--T--R--E--K--R--G--P--S--G--
Mm.HPC2.exon2        AAGACCCACTGCGACACCTGCGTACGCGGGAGAAGCGCGGCCCGGGT---
Mm.HPC2.exon1.pep    --D--P--L--R--H--L--R--T--R--E--K--R--G--P--G-----
                     |---------|---------|---------|---------|---------
                     151       161       171       181       191

Hs.HPC2.exon1        TGCTCCGGCGGCCCAAACACCGTGTACCTGCAGGTGGTGGCAGCGGGTAG
Hs.HPC2.exon1.pep    C--S--G--G--P--N--T--V--Y--L--Q--V--V--A--A--G--S-
Mm.HPC2.exon2        ---CCCGGGGGCCCGAACACCGTGTACCTGCAGGTGGTGGCGGCGGGCGG
Mm.HPC2.exon1.pep    ---P--G--G--P--N--T--V--Y--L--Q--V--V--A--A--G--G-
                     |---------|---------|---------|---------|---------
                     201       211       221       231       241

Hs.HPC2.exon1        CCGGGACTCGGGCGCCGCGCTCTACGTCTTCTCCGAGTTCAACCGgtcag
Hs.HPC2.exon1.pep    -R--D--S--G--A--A--L--Y--V--F--S--E--F--N
Mm.HPC2.exon2        CCGGGACGCGGGGGCTGCTCTCTATGTCTTCTCGGAATACAACAGgtcag
Mm.HPC2.exon1.pep    -R--D--A--G--A--A--L--Y--V--F--S--E--Y--N
                     |---------|---------|---------|---------|---------
                     251       261       271       281       291

Hs.HPC2.exon1        tcaacgagccacgcccgtcccgctgggccctcagtgcggcgcagcctct
Hs.HPC2.exon1.pep
Mm.HPC2.exon2        agtgggccgacagccctgggggattggccccagcgccacgtgctcgggag
Mm.HPC2.exon1.pep
                     |---------|---------|---------|---------|---------
                     301       311       321       331       341
```

Figure 3

CHROMOSOME 17P-LINKED PROSTATE CANCER SUSCEPTIBILITY GENE

CROSS REFERENCE TO RELATED APPLICATION

The present invention is related to U.S. provisional patent application Ser. No. 60/107,468, filed 6 Nov. 1998, incorporated herein by reference.

BACKGROUND OF THE INVENTION

The present invention relates generally to the field of human genetics. Specifically, the present invention relates to methods and materials used to isolate and detect a human prostate cancer predisposing gene (HPC2), some mutant alleles of which cause susceptibility to cancer, in particular, prostate cancer. More specifically, the invention relates to germline mutations in the HPC2 gene and their use in the diagnosis of predisposition to prostate cancer. The present invention further relates to somatic mutations in the HPC2 gene in human prostate cancer and their use in the diagnosis and prognosis of human prostate cancer. The invention also relates to germline mutations in the HPC2 gene and their use in the diagnosis of predisposition to other human cancers. Additionally, the invention relates to somatic mutations in the HPC2 gene in other human cancers and their use in the diagnosis and prognosis of human cancers. The invention also relates to the therapy of human cancers which have a mutation in the HPC2 gene, including gene therapy, protein replacement therapy and protein mimetics. The invention further relates to the screening of drugs for cancer therapy. Finally, the invention relates to the screening of the HPC2 gene for mutations, which are useful for diagnosing the predisposition to prostate cancer.

The publications and other materials used herein to illuminate the background of the invention, and in particular, cases to provide additional details respecting the practice, are incorporated herein by reference, and for convenience, are referenced by author and date in the following text and respectively grouped in the appended List of References.

The genetics of cancer is complicated, involving the function of three loosely defined classes of genes: (1) dominant, positive regulators of the transformed state (oncogenes); (2) recessive, negative regulators of the transformed state (tumor suppressor genes); (3) genes that modify risk without playing a direct role in the biology of transformed cells (risk modifiers).

Specific germline alleles of certain oncogenes and tumor suppressor genes are causally associated with predisposition to cancer. This set of genes is referred to as tumor predisposition genes. Some of the tumor predisposition genes which have been cloned and characterized influence susceptibility to: 1) Retinoblastoma (RB1); 2) Wilms' tumor (WT1); 3) Li-Fraumeni (TP53); 4) Familial adenomatous polyposis (APC); 5) Neurofibromatosis type 1 (NF1); 6) Neurofibromatosis type 2 (NF2); 7) von Hippel-Lindau syndrome (VHL); 8) Multiple endocrine neoplasia type 2A (MEN2A); 9) Melanoma (CDKN2 and CDK4); 10) Breast and ovarian cancer (BRCA1 and BRCA2); 11) Cowden disease (MMAC1); 12) Multiple endocrine neoplasia (MEN1); 13) Nevoid basal cell carcinoma syndrome (PTC); 14) Tuberous sclerosis 2 (TSC2); 15) *Xeroderma pigmentosum* (genes involved in nucleotide excision repair); 16) Hereditary nonpolyposis colorectal cancer (genes involved in mismatch repair).

Specific germline alleles of certain risk modifier genes are also associated with predisposition to cancer, but the increased risk is sometimes only clearly expressed when it is combined with certain environmental, dietary, or other factors. Alcohol dehydrogenase (ADH) oxidizes ethanol to acetaldehyde, a chemical which is both mutagenic and carcinogenic in lab animals. The enzyme encoded by the $ADH3^1$ allele oxidizes ethanol relatively quickly, whereas the enzyme encoded by the $ADH3^2$ allele oxidizes ethanol more slowly. $ADH3^1$ homozygotes presumably have a high capacity for synthesis of acetaldehyde; those who also drink heavily are at increased risk for oral cavity, esophageal, and (in women) breast cancer relative to $ADH3^2$ homozygotes who drink equally heavily (Harty et al., 1997; Hori et al., 1997; Shields, 1997). The acetyltransferases encoded by N-acetyltransferase 1 (NAT1) and N-acetyltransferase 2 (NAT2) catalyze the acetylation of numerous xenobiotics including the aromatic amine carcinogens derived from smoking tobacco products. Individuals who are homozygous for slow acetylating forms of NAT2 who are also heavy smokers are at greater risk for lung, bladder, and (in females) breast cancer than individuals who smoke equally heavily but are homozygous for fast acetylating forms of NAT2 (Shields, 1997; Bouchardy et al., 1998).

The risk of hormone related cancers such as breast and prostate cancer may be modulated by allelic variants in enzymes that play a role in estrogen or androgen metabolism, or variants in proteins that mediate the biological effects of estrogens or androgens. A polymorphic CAG repeat in the human androgen receptor gene encodes a polymorphic polyglutamine tract near the amino-terminus of the protein. The length of the polyglutamine tract is inversely correlated with the transcriptional activation activity of the androgen receptor and thus one aspect of the biological response to androgens. Men whose androgen receptor contains a relatively short polyglutamine tract are at higher risk for prostate cancer, especially high stage/high histologic grade prostate cancer, than men whose androgen receptor contains a relatively long polyglutamine tract (Giovannucci et al., 1997).

Prostate cancer is the most common cancer in men in many western countries, and the second leading cause of cancer deaths in men. It accounts for more than 40,000 deaths in the US annually. The number of deaths is likely to continue rising over the next 10 to 15 years. In the US, prostate cancer is estimated to cost $1.5 billion per year in direct medical expenses. In addition to the burden of suffering, it is a major public-health issue. Numerous studies have provided evidence for familial clustering of prostate cancer, indicating that family history is a major risk factor for this disease (Cannon et al., 1982; Steinberg et al., 1990; Carter et al, 1993).

Prostate cancer has long been recognized to be, in part, a familial disease. Numerous investigators have examined the evidence for genetic inheritance and concluded that the data are most consistent with dominant inheritance for a major susceptibility locus or loci. Woolf (1960), described a relative risk of 3.0 of developing prostate cancer among first-degree relatives of prostate cancer cases in Utah using death certificate data. Relative risks ranging from 3 to 11 for first-degree relatives of prostate cancer cases have been reported (Cannon et al., 1982; Woolf, 1960; Fincham et al., 1990; Meikle et al., 1985; Krain, 1974; Morganti et al., 1956; Goldgar et al., 1994). Carter et al. (1992) performed segregation analysis on families ascertained through a single prostate cancer proband. The analysis suggested Mendelian inheritance in a subset of families through autosomal dominant inheritance of a rare (q=0.003), high-risk allele with estimated cumulative risk of prostate cancer for carriers of 88% by age 85. Inherited prostate cancer susceptibility accounted for a significant proportion of early-onset disease, and overall was responsible for 9% of prostate occurrence by age 85. Recent results demonstrate that at least four loci exist which convey susceptibility to prostate cancer as well as other cancers. These loci are HPC1 on chromosome 1 q, (Smith et al., 1996), HPC2 on chromosome 17p (this patent application, Example 1), HPCX on chromosome Xp (Xu et al., 1998), and one or more loci responsible for the unmapped residual.

Detection of genetic linkage for prostate cancer susceptibility to a defined segment of a chromosome requires that DNA sequence variants within that chromosomal segment confer the cancer susceptibility. This is usually taken to mean that the causal sequence variant(s) will either alter the expression of one or more linked genes or will alter the function of one of the linked genes. However, detection of the genetic linkage does not necessarily provide evidence for what class of gene (i.e. tumor suppressor, oncogene, or risk modifier) is affected by the causal sequence variant(s).

Most strategies for proceeding from genetic linkage of prostate cancer susceptibility to chromosome 17p to identification of the 17p-linked prostate cancer predisposing gene (HPC2) require precise genetic localization studies to define a discrete segment of the chromosome within which the causal sequence variant(s) must map. Gene identification projects based on precise genetic localization are called positional cloning projects. The general strategy in positional cloning is to find all of the genes located within the genetically defined interval, identify sequence variants in and around those genes, and then determine which of those sequence variants either alter the expression or the function of one (or more) of the associated genes. Segregation of such sequence variants with the disease in the linked kindreds must also be demonstrated. We have executed a positional cloning project in the HPC2 region of chromosome 17p and found a gene, herein named HPC2, germline mutations which predispose individuals to prostate cancer.

SUMMARY OF THE INVENTION

The present invention relates generally to the field of human genetics. Specifically, the present invention relates to methods and materials used to isolate and detect a human prostate cancer predisposing gene (HPC2), some alleles of which cause susceptibility to cancer, in particular prostate cancer. More specifically, the present invention relates to germline mutations in the HPC2 gene and their use in the diagnosis of predisposition to prostate cancer. The invention also relates to presymptomatic therapy of individuals who carry deleterious alleles of the HPC2 gene. The invention further relates to somatic mutations in the HPC2 gene in human prostate cancer and their use in the diagnosis and prognosis of human prostate cancer. Additionally, the invention relates to somatic mutations in the HPC2 gene in other human cancers and their use in the diagnosis and prognosis of human cancers. The invention also relates to the therapy of human cancers which have a mutation in the HPC2 gene, (including gene therapy, protein replacement therapy, protein mimetics, and inhibitors). The invention further relates to the screening of drugs for cancer therapy. Finally, the invention relates to the screening of the HPC2 gene for mutations, which are useful for diagnosing the predisposition to prostate cancer. The HPC2 gene is useful as a marker for the HPC2 locus and as a marker for prostate cancer.

BRIEF DESCRIPTION OF THE DRAWINGS

FIG. 3 is an alignment of the sequence of exon 1 of the human HPC2 gene with exon 1 of the mouse HPC2 gene. The figure also shows an alignment of the peptide sequence encoded by exon 1 of the human HPC2 gene with the peptide sequence encoded by exon 1 of the mouse HPC2 gene. The human DNA sequence is SEQ ID NO:210; the human amino acid sequence is SEQ ID NO:211; the mouse DNA sequence is SEQ ID NO:212 and the mouse amino acid sequence is SEQ ID NO:23.

BRIEF DESCRIPTION OF THE TABLES

Figure 1:
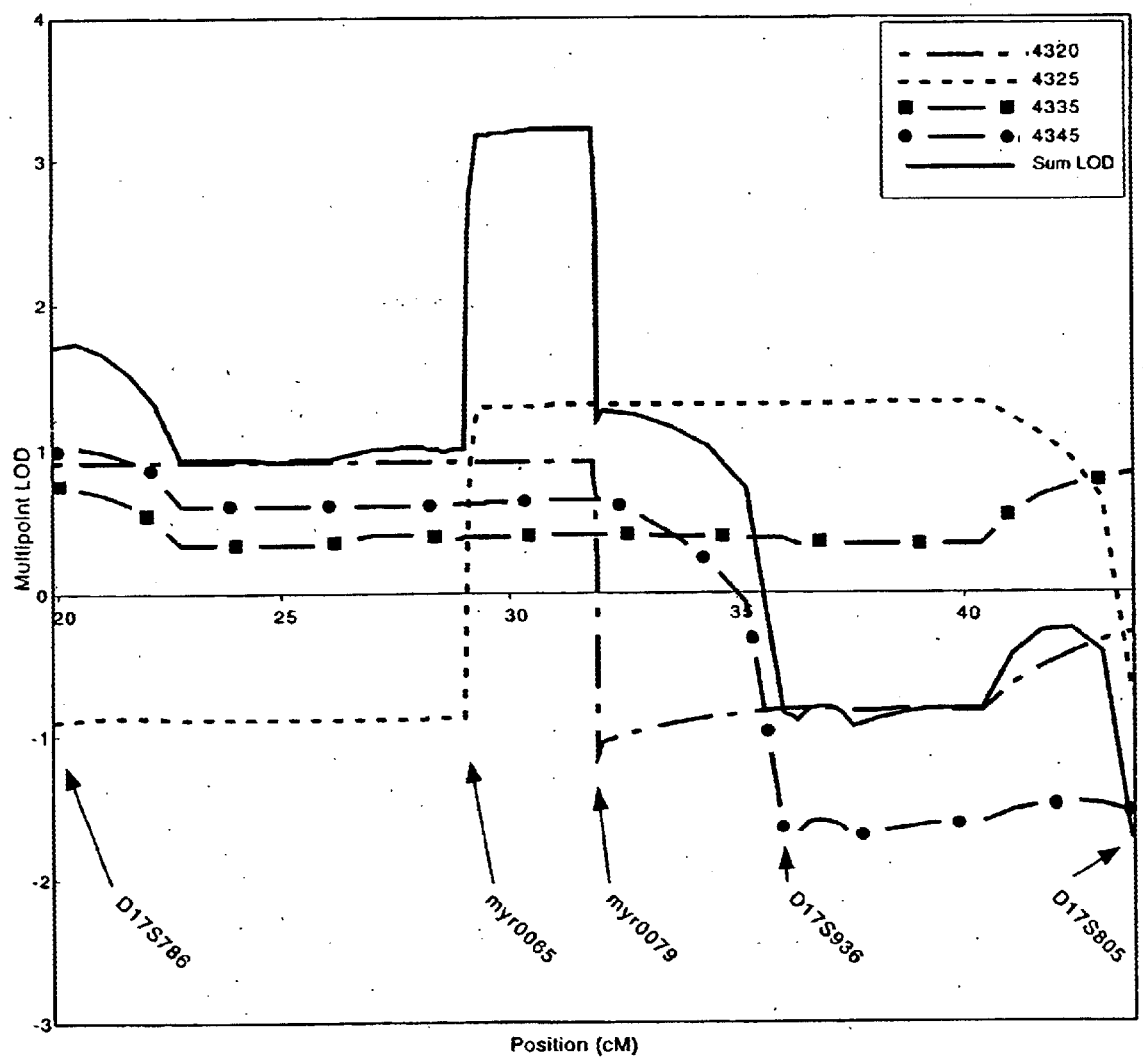
FIG. 1 is a multipoint linkage analysis of 4 kindreds that show suggestive evidence for linkage to the HPC2 prostate cancer susceptibility locus relative to chromosome 17p markers.

Table 1 is a compilation of 2-point LOD scores for markers in the HPC2 region.

Table 2 is a list of the accession numbers of human EST sequences used to assemble a tentative, partial cDNA sequence of the human HPC2 gene.

Table 3 is a list of the primers used for obtaining 5' RACE products that contained the start codon and part of the 5' UTR of the human HPC2 gene, primers used to prepare a full length human HPC2 expression construct, and primers used to check the sequence of that construct.

Table 4 is a list of the accession numbers of mouse EST sequences used to assemble a tentative, partial cDNA sequence of the mouse HPC2 gene.

Table 5 is a list of the primers used for obtaining 5' RACE products that contained the start codon and part of the 5' UTR of the mouse HPC2 gene, primers used to prepare a full length mouse HPC2 expression construct, and primers used to check the sequence of that construct.

Table 6 is a list of the primers used to mutation screen the human HPC2 gene from genomic DNA.

Table 7 is a summary of germline sequence variants of the human HPC2-gene.

SUMMARY OF SEQUENCE LISTING

SEQ ID NO:1 is the nucleotide sequence for the human HPC2 cDNA from the start codon through the stop codon. SEQ ID NO:2 is the amino acid sequence for the human HPC2 protein. SEQ ID NO:3 is the nucleotide sequence for the human HPC2 cDNA from 50 base pairs before the start codon through the end of the 3' UTR. SEQ ID NO:4 to SEQ ID NO:27 are the sequences of exon 1 to exon 24 of the human HPC2 gene. SEQ ID NO:28 is the genomic sequence of the human HPC2 gene. SEQ ID NOs:29–190 are nucleotide sequences of primers used to identify the human and/or mouse HPC2 genes or to screen for mutations. SEQ ID NOs:191–209 are nucleotide sequences of the HPC2 around and including various sequence variants. SEQ ID NO:210 is the nucleotide sequence of human HPC2 exon 1 and SEQ ID NO:211 is the corresponding amino acid sequence. SEQ ID NO:213 is nucleotide sequence of mouse HPC2 exon 1 and SEQ ID NO:213 is the corresponding amino acid sequence.

DETAILED DESCRIPTION OF THE INVENTION

The present invention provides an isolated polynucleotide comprising all, or a portion of the HPC2 locus or of a mutated HPC2 locus, preferably at least eight bases and not more than about 27 kb in length. Such polynucleotides may be antisense polynucleotides. The present invention also provides a recombinant construct comprising such an isolated polynucleotide, for example, a recombinant construct suitable for expression in a transformed host cell.

Also provided by the present invention are methods of detecting a polynucleotide comprising a portion of the HPC2 locus or its expression product in an analyte. Such methods may further comprise the step of amplifying the portion of the HPC2 locus, and may further include a step of providing a set of polynucleotides which are primers for amplification of said portion of the HPC2 locus. The method is useful for either diagnosis of the predisposition to cancer or the diagnosis or prognosis of cancer. The HPC2 gene is useful as a marker for the HPC2 locus and as a marker for prostate cancer.

The present invention also provides isolated antibodies, preferably monoclonal antibodies, which specifically bind to an isolated polypeptide comprised of at least five amino acid residues encoded by the HPC2 locus.

The present invention also provides kits for detecting in an analyte a polynucleotide comprising a portion of the HPC2 locus, the kits comprising a polynucleotide complementary to the portion of the HPC2 locus packaged in a suitable container, and instruction for its use.

The present invention further provides methods of preparing a polynucleotide comprising polymerizing nucleotides to yield a sequence comprised of at least eight consecutive nucleotides of the HPC2 locus; and methods of preparing a polypeptide comprising polymerizing amino acids to yield a sequence comprising at least five amino acids encoded within the HPC2 locus.

The present invention further provides methods of screening the HPC2 gene to identify mutations. Such methods may further comprise the step of amplifying a portion of the HPC2 locus, and may further include a step of providing a set of polynucleotides which are primers for amplification of said portion of the HPC2 locus. Such methods may also include a step of providing the complete set of short polynucleotides defined by the sequence of HPC2 or discrete subsets of that sequence, all single-base substitutions of that sequence or discrete subsets of that sequence, all 1-, 2-, 3-, or 4-base deletions of that sequence or discrete subsets of that sequence, and all 1-, 2-, 3-, or 4-base insertions in that sequence or discrete subsets of that sequence. The method is useful for identifying mutations for use in either diagnosis of the predisposition to cancer or the diagnosis or prognosis of cancer.

The present invention further provides methods of screening suspected HPC2 mutant alleles to identify mutations in the HPC2 gene.

In addition, the present invention provides methods to screen drugs for inhibition or restoration of HPC2 gene product function as an anticancer therapy.

Finally, the present invention provides the means necessary for production of gene-based therapies directed at cancer cells. These therapeutic agents may take the form of polynucleotides comprising all or a portion of the HPC2 locus placed in appropriate vectors or delivered to target cells in more direct ways such that the function of the HPC2 protein is reconstituted. Therapeutic agents may also take the form of polypeptides based on either a portion of, or the entire protein sequence of HPC2. These may functionally replace the activity of HPC2 in vivo.

It is a discovery of the present invention that the HPC2 locus which predisposes individuals to prostate cancer, is a gene encoding an HPC2 protein, which has been found to be non-identical to publicly available protein or cDNA sequences. This gene is termed HPC2 herein. It is a discovery of the present invention that mutations in the HPC2 locus in the germline are indicative of a predisposition to prostate cancer. Finally, it is a discovery of the present invention that germline mutations in the HPC2 locus are also associated with prostate cancer and other types of cancer. The mutational events of the HPC2 locus can involve deletions, insertions and nucleotide substitutions within the coding sequence and the non-coding sequence.

Useful Diagnostic Techniques

According to the diagnostic and prognostic method of the present invention, alteration of the wild-type HPC2 locus is detected. In addition, the method can be performed by detecting the wild-type HPC2 locus and confirming the lack of a predisposition to cancer at the HPC2 locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues, e.g., in the tumor tissue, and are not inherited in the germline. Germline mutations can be found in any of a body's tissues and are inherited. If only a single allele is somatically mutated, an early neoplastic state is indicated. However, if both alleles are somatically mutated, then a late neoplastic state is indicated. The finding of HPC2 mutations thus provides both diagnostic and prognostic information. An HPC2 allele which is not deleted (e.g., found on the sister chromosome to a chromosome carrying an HPC2 deletion) can be screened for other mutations, such as insertions, small deletions, and point mutations. It is believed that many mutations found in tumor tissues will be those leading to decreased expression of the HPC2 gene product. However, mutations leading to non-functional gene products would also lead to a cancerous state. Point mutational events may occur in regulatory regions, such as in the promoter of the gene, leading to loss or diminution of expression of the mRNA. Point mutations may also abolish proper RNA processing, leading to reduction or loss of expression of the HPC2 gene product, expression of an altered HPC2 gene product, or to a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis, hybridization using nucleic acid modified with gold nanoparticles and PCR-SSCP, as discussed in detail further below. Also useful is the recently developed technique of DNA microchip technology.

Predisposition to cancers, such as prostate cancer, and the other cancers identified herein, can be ascertained by testing any tissue of a human for mutations of the HPC2 gene. For example, a person who has inherited a germline HPC2 mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the HPC2 gene. Alteration of a wild-type HPC2 allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. For a gene as large as HPC2, manual sequencing is very labor-intensive, but under optimal conditions, mutations in the coding sequence of a gene are rarely missed. Another approach is the single-stranded conformation polymorphism assay (SSCA) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments which have shifted mobility on SSCA gels are then sequenced to determine the exact nature of the DNA sequence variation. Other approaches based on the detection of mismatches between the two complementary DNA strands include clamped denaturing gel electrophoresis (CDGE) (Sheffield et al, 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

In order to detect the alteration of the wild-type HPC2 gene in a tissue, it is helpful to isolate the tissue free from surrounding normal tissues. Means for enriching tissue preparation for tumor cells are known in the art. For example, the tissue may be isolated from paraffin or cryostat sections. Cancer cells may also be separated from normal cells by flow cytometry. These techniques, as well as other techniques for separating tumor cells from normal cells, are well known in the art. If the tumor tissue is highly contaminated with normal cells, detection of mutations is more difficult.

Detection of point mutations may be accomplished by molecular cloning of the HPC2 allele(s) and sequencing the allele(s) using techniques well known in the art. Alternatively, the gene sequences can be amplified directly from a genomic DNA preparation from the tumor tissue, using known techniques. The DNA sequence of the amplified sequences can then be determined.

There are six well known methods for a more complete, yet still indirect, test for confirming the presence of a susceptibility allele: 1) single-stranded conformation analysis (SSCA) (Orita et al., 1989); 2) denaturing gradient gel electrophoresis (DGGE) (Wartell et al., 1990; Sheffield et al, 1989); 3) RNase protection assays (Finkelstein et al, 1990; Kinszler et al., 1991); 4) allele-specific oligonucleotides (ASOs) (Conner et al, 1983); 5) the use of proteins which recognize nucleotide mismatches, such as the E. coli mutS protein (Modrich, 1991); and 6) allele-specific PCR (Ruano and Kidd, 1989). For allele-specific PCR, primers are used which hybridize at their 3' ends to a particular HPC2 mutation. If the particular HPC2 mutation is not present, an amplification product is not observed. Amplification Refractory Mutation System (ARMS) can also be used, as disclosed in European Patent Application Publication No. 0332435 and in Newton et al, 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the HPC2 mutation found in that individual. Other techniques for detecting insertions and deletions as known in the art can be used.

In the first three methods (SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of tumor samples. An example of a mismatch cleavage technique is the RNase protection method. In the practice of the present invention, the method involves the use of a labeled riboprobe which is complementary to the human wild-type HPC2 gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the HPC2 mRNA or gene but can be a segment of either. If the riboprobe comprises only a segment of the HPC2 mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al, 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the HPC2 gene can also be detected using Southern hybridization, especially if the changes are gross rearrangements, such as deletions and insertions.

DNA sequences of the HPC2 gene which have been amplified by use of PCR may also be screened using allele-specific probes. These probes are nucleic acid oligomers, each-of which contains a region of the HPC2 gene sequence harboring a known mutation. For example, one oligomer may be about 30 nucleotides in length (although shorter and longer oligomers are also usable as well recognized by those of skill in the art), corresponding to a portion of the HPC2 gene sequence. By use of a battery of such allele-specific probes, PCR amplification products can be screened to identify the presence of a previously identified mutation in the HPC2 gene. Hybridization of allele-specific probes with amplified HPC2 sequences can be performed, for example, on a nylon filter. Hybridization to a particular probe under high stringency hybridization conditions indicates the presence of the same mutation in the tumor tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Nature Genetics, 1996). Also see Fodor (1997).

The most definitive test for mutations in a candidate locus is to directly compare genomic HPC2 sequences from cancer patients with those from a control population. Alternatively, one could sequence messenger RNA after amplification, e.g., by PCR, thereby eliminating the necessity of determining the exon structure of the candidate gene.

Mutations from cancer patients falling outside the coding region of HPC2 can be detected by examining the non-coding regions, such as introns and regulatory sequences near or within the HPC2 gene. An early indication that mutations in noncoding regions are important may come from Northern blot experiments that reveal messenger RNA molecules of abnormal size or abundance in cancer patients as compared to control individuals.

Alteration of HPC2 mRNA expression can be detected by any techniques known in the art. These include Northern blot analysis, PCR amplification and RNase protection. Diminished mRNA expression indicates an alteration of the wild-type HPC2 gene. Alteration of wild-type HPC2 genes can also be detected by screening for alteration of wild-type HPC2 protein. For example, monoclonal antibodies immunoreactive with HPC2 can be used to screen a tissue. Lack of cognate antigen would indicate an HPC2 mutation. Antibodies specific for products of mutant alleles could also be used to detect mutant HPC2 gene product. Such immunological assays can be done in any convenient formats known in the art. These include Western blots, immunohistochemical assays and ELISA assays. Any means for detecting an altered HPC2 protein can be used to detect alteration of wild-type HPC2 genes. Functional assays, such as protein binding determinations, can be used. In addition, assays can be used which detect HPC2 biochemical function. Finding a mutant HPC2 gene product indicates alteration of a wild-type HPC2 gene.

Mutant HPC2 genes or gene products can also be detected in other human body samples, such as serum, stool, urine and sputum. The same techniques discussed above for detection of mutant HPC2 genes or gene products in tissues can be applied to other body samples. Cancer cells are sloughed off from tumors and appear in such body samples. In addition, the HPC2 gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant HPC2 genes or gene products.

The methods of diagnosis of the present invention are applicable to any tumor in which HPC2 has a role in tumorigenesis. The diagnostic method of the present invention is useful for clinicians, so they can decide upon an appropriate course of treatment.

The primer pairs of the present invention are useful for determination of the nucleotide sequence of a particular HPC2 allele using PCR. The pairs of single-stranded DNA primers can be annealed to sequences within or surrounding the HPC2 gene on chromosome 17 in order to prime amplifying DNA synthesis of the HPC2 gene itself. A complete set of these primers allows synthesis of all of the nucleotides of the HPC2 gene coding sequences, i.e., the exons. The set of primers preferably allows synthesis of both intron and exon sequences. Allele-specific primers can also be used. Such primers anneal only to particular HPC2 mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from HPC2 sequences or sequences adjacent to HPC2, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of the HPC2 open reading frame shown in SEQ ID NOs:1 and 3, design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the HPC2 gene or mRNA using other techniques.

It has been discovered that individuals with the wild-type HPC2 gene do not have cancer which results from the HPC2 allele. However, mutations which interfere with the function of the HPC2 protein are involved in the pathogenesis of cancer. Thus, the presence of an altered (or a mutant) HPC2 gene which produces a protein having a loss of function, or altered function, directly correlates to an increased risk of cancer. In order to detect an HPC2 gene mutation, a biological sample is prepared and analyzed for a difference between the sequence of the HPC2 allele being analyzed and the sequence of the wild-type HPC2 allele. Mutant HPC2 alleles can be initially identified by any of the techniques described above. The mutant alleles are then sequenced to identify the specific mutation of the particular mutant allele. Alternatively, mutant HPC2 alleles can be initially identified by identifying mutant (altered) HPC2 proteins, using conventional techniques. The mutant alleles are then sequenced to identify the specific mutation for each allele. The mutations, especially those which lead to an altered function of the HPC2 protein, are then used for the diagnostic and prognostic methods of the present invention.

Definitions

The present invention employs the following definitions:

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al, 1990 (for PCR); and Wu and Wallace, 1989 (for LCR); U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the HPC2 region are preferably complementary to, and hybridize specifically to sequences in the HPC2 region or in regions that flank a target region therein. HPC2 sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf, 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the HPC2 polypeptides and fragments thereof or to polynucleotide sequences from the HPC2 region, particularly from the HPC2 locus or a portion thereof. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the HPC2 polypeptide or fragment. Monoclonal antibodies may be made by injecting mice with the protein polypeptides, fusion proteins or fragments thereof. Monoclonal antibodies will be screened by ELISA and tested for specific immunoreactivity with HPC2 polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ $M^{-1}$ or preferably $10^{-9}$ to $10^{-10}$ $M^{-1}$ or stronger will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837, 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. Further binding partners can be identified using, e.g., the two-hybrid yeast screening assay as described herein.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

As used herein, the terms "diagnosing" or "prognosing," as used in the context of neoplasia, are used to indicate 1) the classification of lesions as neoplasia, 2) the determination of the severity of the neoplasia, or 3) the monitoring of the disease progression, prior to, during and after treatment.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The antisense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"HPC2 Allele" refers to normal alleles of the HPC2 locus as well as alleles carrying variations that predispose individuals to develop prostate cancer. Such predisposing alleles are also called "HPC2 susceptibility alleles".

"HPC2 Locus", "HPC2 Gene", "HPC2 Nucleic Acids" or "HPC2 Polynucleotide" each refer to polynucleotides, all of which are in the HPC2 region, that are likely to be expressed in normal tissue, certain alleles of which predispose an individual to develop prostate cancers. Mutations at the HPC2 locus may be involved in the initiation and/or progression of other types of tumors. The locus is indicated in part by mutations that predispose individuals to develop cancer. These mutations fall within the HPC2 region described infra. The HPC2 locus is intended to include coding sequences, intervening sequences and regulatory elements controlling transcription and/or translation. The HPC2 locus is intended to include all allelic variations of the DNA sequence.

These terms, when applied to a nucleic acid, refer to a nucleic acid which encodes an HPC2 polypeptide, fragment, homolog or variant, including, e.g., protein fusions or deletions. The nucleic acids of the present invention will possess a sequence which is either derived from, or substantially similar to a natural HPC2-encoding gene or one having substantial homology with a natural HPC2-encoding gene or a portion thereof.

The HPC2 gene or nucleic acid includes normal alleles of the HPC2 gene, including silent alleles having no effect on the amino acid sequence of the HPC2 polypeptide as well as alleles leading to amino acid sequence variants of the HPC2 polypeptide that do not substantially affect its function. These terms also include alleles having one or more mutations which adversely affect the function of the HPC2 polypeptide. A mutation may be a change in the HPC2 nucleic acid sequence which produces a deleterious change in the amino acid sequence of the HPC2 polypeptide, resulting in partial or complete loss of HPC2 function, or may be a change in the nucleic acid sequence which results in the loss of effective HPC2 expression or the production of aberrant forms of the HPC2 polypeptide.

The HPC2 nucleic acid may be that shown in SEQ ID NOs:1, 3 or 28 or it may be an allele as described above or a variant or derivative differing from that shown by a change which is one or more of addition, insertion, deletion and substitution of one or more nucleotides of the sequence shown. Changes to the nucleotide sequence may result in an amino acid change at the protein level, or not, as determined by the genetic code.

Thus, nucleic acid according to the present invention may include a sequence different from the sequence shown in SEQ ID NOs:1, 3 or 28 yet encode a polypeptide with the same amino acid sequence as shown in SEQ ID NO:1. That is, nucleic acids of the present invention include sequences which are degenerate as a result of the genetic code. On the other hand, the encoded polypeptide may comprise an amino acid sequence which differs by one or more amino acid residues from the amino acid sequence shown in SEQ ID NO:2. Nucleic acid encoding a polypeptide which is an amino acid sequence variant, derivative or allele of the amino acid sequence shown in SEQ ID NO:2 is also provided by the present invention.

The HPC2 gene also refers to (a) any DNA sequence that (i) hybridizes to the complement of the DNA sequences that encode the amino acid sequence set forth in SEQ ID NO:2 under highly stringent conditions (Ausubel et al., 1992) and (ii) encodes a gene product functionally equivalent to HPC2, or (b) any DNA sequence that (i) hybridizes to the complement of the DNA sequences that encode the amino acid sequence set forth in SEQ ID NO:2 under less stringent conditions, such as moderately stringent conditions (Ausubel et al., 1992) and (ii) encodes a gene product functionally equivalent to HPC2. The invention also includes nucleic acid molecules that are the complements of the sequences described herein.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the HPC2 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it will often be altered, e.g., by deletion, substitution or insertion.

cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with an HPC2-encoding sequence. In this context, oligomers of as low as 8 nucleotides, more generally 8–17 nucleotides, can be used for probes, especially in connection with chip technology.

Techniques for nucleic acid manipulation are described generally, for example, in Sambrook et al., 1989 or Ausubel et al, 1992. Reagents useful in applying such techniques, such as restriction enzymes and the like, are widely known in the art and commercially available from such vendors as New England BioLabs, Boehringer Mannheim, Amersham, Promega Biotec, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See GenBank, National Institutes of Health.

"HPC2 Region" refers to a portion of human chromosome 17 bounded by the markers D17S947 and D17S799. This region contains the HPC2 locus, including the HPC2 gene.

As used herein, the terms "HPC2 locus", "HPC2 allele" and "HPC2 region" all refer to the double-stranded DNA comprising the locus, allele, or region, as well as either of the single-stranded DNAs comprising the locus, allele or region.

As used herein, a "portion" of the HPC2 locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides. The present invention includes all novel nucleic acids having at least 8 nucleotides derived from any of SEQ ID NOs:1 or 3–28, its complement or functionally equivalent nucleic acid sequences. The present invention does not include nucleic acids which exist in the prior art. That is, the present invention includes all nucleic acids having at least 8 nucleotides derived from any of SEQ ID NOs:1 or 3–28 with the proviso that it does not include nucleic acids existing in the prior art.

"HPC2 protein" or "HPC2 polypeptide" refers to a protein or polypeptide encoded by the HPC2 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native HPC2 sequence, preferably in excess of about 90%, and more preferably at least about 95% homologous. Also included are proteins encoded by DNA which hybridize under high or low stringency conditions, to HPC2-encoding nucleic acids and closely related polypeptides or proteins retrieved by antisera to the HPC2 protein(s).

An HPC2 polypeptide may be that derived from any of the exons described herein which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of an HPC2 polypeptide. Such polypeptides may have an amino acid sequence which differs from that derived from any of the exons described herein by one or more of addition, substitution, deletion or insertion of one or more amino acids. Preferred such polypeptides have HPC2 function.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with an HPC2 polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art (Kyte and Doolittle, 1982). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is further discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression.

The term peptide mimetic or mimetic is intended to refer to a substance which has the essential biological activity of an HPC2 polypeptide. A peptide mimetic may be a peptide-containing molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of a natural HPC2 polypeptide.

"Probes". Polynucleotide polymorphisms associated with HPC2 alleles which predispose to certain cancers or are associated with most cancers are detected by hybridization with a polynucleotide probe which forms a stable hybrid with that of the target sequence, under highly stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that is meant to be read as "high stringency" conditions are used.) Since such indications identify neutral DNA polymorphisms as well as mutations, these indications need further analysis to demonstrate detection of an HPC2 susceptibility allele. An example of high stringency conditions is to hybridize to filer bound DNA in 0.5 M NaHPO$_4$, 7% sodium dodecyl sulfate (SDS), 1 mM EDTA at 65° C. and to wash in 0.1×SSC/0.1% SDS at 68° C. (Ausubel et al., 1992). Less stringent conditions, such as moderately stringent conditions, are defined as above but with the wash step being in 0.2×SSC/0.1% SDS at 42° C.

Probes for HPC2 alleles may be derived from the sequences of the HPC2 region, its cDNA, functionally equivalent sequences, or the complements thereof. The probes may be of any suitable length, which span all or a portion of the HPC2 region, and which allow specific hybridization to the HPC2 region. If the target sequence contains a sequence identical to that of the probe, the probes may be short, e.g., in the range of about 8–30 base pairs, since the hybrid will be relatively stable under even highly stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 9 kb, usually fewer than about 1.0 kb, from a polynucleotide sequence encoding HPC2 are preferred as probes. This definition therefore includes probes of sizes 8 nucleotides through 9000 nucleotides. Thus, this definition includes probes of 8, 12, 15, 20, 25, 40, 60, 80, 100, 200, 300, 400 or 500 nucleotides or probes having any number of nucleotides within these ranges of values (e.g., 9, 10, 11, 16, 23, 30, 38, 50, 72; 121, etc., nucleotides), or probes having more than 500 nucleotides. The probes may also be used to determine whether mRNA encoding HPC2 is present in a cell or tissue. The present invention includes all novel probes having at least 8 nucleotides derived from any of SEQ ID NOs:1 or 3–28 its complement or functionally equivalent nucleic acid sequences. The present invention does not include probes which exist in the prior art. That is, the present invention includes all probes having at least 8 nucleotides derived from any of SEQ ID NOs:1 or 3–28 with the proviso that they do not include probes existing in the prior art.

Similar considerations and nucleotide lengths are also applicable to primers which may be used for the amplification of all or part of the HPC2 gene. Thus, a definition for primers includes primers of 8, 12, 15, 20, 25, 40, 60, 80, 100, 200, 300, 400, 500 nucleotides, or primers having any number of nucleotides within these ranges of values (e.g., 9, 10, 11, 16, 23, 30, 38, 50, 72, 121, etc. nucleotides), or primers having more than 500 nucleotides, or any number of nucleotides between 500 and 9000. The primers may also be used to determine whether mRNA encoding HPC2 is present in a cell or tissue. The present invention includes all novel primers having at least 8 nucleotides derived from the HPC2 locus for amplifying the HPC2 gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for HPC2 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}$P, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of HPC2 polypeptides. Immunological activities include both immunogenic function in a target immune system, as well as sharing of immunological epitopes for binding, serving as either a competitor or substitute antigen for an epitope of the HPC2 protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for HPC2 polypeptides or fragments thereof is described below.

The present invention also provides for fusion polypeptides, comprising HPC2 polypeptides and fragments. Homologous polypeptides may be fusions between two or more HPC2 polypeptide sequences or between the sequences of HPC2 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See Godowski et al., 1988.

Fusion proteins will typically be made by either recombinant nucleic acid methods, as described below, or may be chemically synthesized. Techniques for the synthesis of polypeptides are described, for example, in Merrifield, 1963.

"Protein purification" refers to various methods for the isolation of the HPC2 polypeptides from other biological material, such as from cells transformed with recombinant nucleic acids encoding HPC2, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

An HPC2 protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Identity means the degree of sequence relatedness between two polypeptide or two polynucleotides sequences as determined by the identity of the match between two strings of such sequences. Identity can be readily calculated. While there exist a number of methods to measure identity between two polynucleotide or polypeptide sequences, the term "identity" is well known to skilled artisans (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Methods commonly employed to determine identity between two sequences include, but are not limited to those disclosed in *Guide to Huge Computers*, Martin J. Bishop, ed., Academic Press, San Diego, 1994, and Carillo, H., and Lipman, D. (1988). Preferred methods to determine identity are designed to give the largest match between the two sequences tested. Such methods are codified in computer programs. Preferred computer program methods to determine identity between two sequences include, but are not limited to, GCG program package (Devereux et al. (1984), BLASTP, BLASTN, FASTA (Altschul et al. (1990); Altschul et al. (1997)).

Alternatively, substantial homology or similarity exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. See, e.g., Wetmur and Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more ususally at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705, as well as the software described above with reference to nucleic acid homology. Protein analysis software matches similar sequences using measures of homology assigned to various If substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type HPC2 nucleic acid or wild-type HPC2 polypeptide. The modified polypeptide will be substantially homologous to the wild-type HPC2 polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type HPC2 polypeptide. Alternatively, the similarity of function (activity) of the modified polypeptide may be higher than the activity of the wild-type HPC2 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type HPC2 gene function produces the modified protein described above.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al, 1982; Sambrook et al, 1989; Ausubel et al, 1992; Glover, 1985;

Anand, 1992; Guthrie and Fink, 1991. A general discussion of techniques and materials for human gene mapping, including mapping of human chromosome 1, is provided, e.g., in White and Lalouel, 1988.

Preparation of Recombinant or Chemically Synthesized Nucleic Acids: Vectors, Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention is described, e.g., in Sambrook et al., 1989 or Ausubel et al., 1992.

The polynucleotides of the present invention may also be produced by chemical synthesis, e.g., by the phosphoramidite method described by Beaucage and Caruthers, 1981 or the triester method according to Matteucci and Caruthers, 1981, and may be performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate, whether from a native HPC2 protein or from other receptors or from secreted polypeptides of the same or related species, which allow the protein to cross and/or lodge in cell membranes, and thus attain its functional topology, or be secreted from the cell. Such vectors may be prepared by means of standard recombinant techniques well known in the art and discussed, for example, in Sambrook et al., 1989 or Ausubel et al. 1992.

An appropriate promoter and other necessary vector sequences will be selected so as to be functional in the host, and may include, when appropriate, those naturally associated with HPC2 genes. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England BioLabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Moloney leukemia virus, mouse tumor virus, avian sarcoma viruses, adenovirus II, bovine papilloma virus or polyoma. Insection promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, Cold Spring Harbor, N.Y. (1983). See also, e.g., U.S. Pat. Nos. 5,691,198; 5,735,500; 5,747,469 and 5,436,146.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al., 1988), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the HPC2 nucleic acids or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or *Pseudomonas* may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan, 1979. Examples of commonly used mammalian host cell lines are VERO and HeLa cells, Chinese hamster ovary (CHO) cells, and W138, BHK, and COS cell lines, although it will be appreciated by the skilled practitioner that other cell lines may be appropriate, e.g., to provide higher expression, desirable glycosylation patterns, or other features. An example of a commonly used insect cell line is SF9.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of HPC2 polypeptides.

The HPC2 gene products can also be expressed in transgenic animals. Animals of any species, including, but not limited to, mice, rats, rabbits, guinea pigs, pigs, micro-pigs, goats and non-human primates, e.g., baboons, monkeys and chimpanzees, may be used to generate HPC2 transgenic animals.

Any technique known in the art may be used to introduce the HPC2 gene transgene into animals to produce the founder lines of transgenic animals. Such techniques include, but are not limited to, pronuclear microinjection (U.S. Pat. No. 4,873,191); retrovirus mediated gene transfer into germ lines (Van der Putten et al., 1985); gene targeting in embryonic stem cells (Thompson et al., 1989); electroporation of embryos (Lo, 1983); and sperm-mediated gene transfer (Lavitrano et al., 1989); etc. For a review of such techniques, see Gordon (1989), which is incorporated by reference herein in its entirety.

The present invention provides for transgenic animals that carry the HPC2 transgene in all their cells, as well as animals which carry the transgene in some, but not all of their cells, i.e., mosaic animals. The transgene may be integrated as a single transgene or in concatamers, e.c., head-to-head tandems or head-to-tail tandems. The transgene may also be selectively introduced into and activated in a particular cell type by following, for example, the teaching of Lasko et al. (1992). The regulatory sequences required for such a cell-type specific activation will depend upon the particular cell type of interest, and will be apparent to those of skill in the art. When it is desired that the HPC2 gene transgene be integrated into the chromosomal site of the endogenous HPC2 gene, gene targeting is preferred. Briefly, when such a technique is to be utilized, vectors containing some nucleotide sequences homologous to the endogenous HPC2 gene are designed for the purpose of integrating, via homologous recombination with chromosomal sequences, into and disrupting the function of the nucleotide sequence of the endogenous HPC2 gene. The transgene may also be selectively introduced into a particular cell type, thus inactivating the endogenous HPC2 gene in only that cell type, by following, for example, the teaching of Gu et al. (1994). The regulatory sequences required for such a cell-type specific inactivation will depend upon the particular cell type of interest, and will be apparent to those of skill in the art.

Once transgenic animals have been generated, the expression of the recombinant HPC2 gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Samples of HPC2 gene-expressing tissue, may also be evaluated immunocytochemically using antibodies specific for the HPC2 transgene product.

Antisense polynucleotide sequences are useful in preventing or diminishing the expression of the HPC2 locus, as will be appreciated by those skilled in the art. For example, polynucleotide vectors containing all or a portion of the HPC2 locus or other sequences from the HPC2 region (particularly those flanking the HPC2 locus) may be placed under the control of a promoter in an antisense orientation and introduced into a cell. Expression of such an antisense construct within a cell will interfere with HPC2 transcription and/or translation and/or replication.

The probes and primers based on the HPC2 gene sequences disclosed herein are used to identify homologous HPC2 gene sequences and proteins in other species. These HPC2 gene sequences and proteins are used in the diagnostic/prognostic, therapeutic and drug screening methods described herein for the species from which they have been isolated.

Methods of Use: Nucleic Acid Diagnosis and Diagnostic Kits

In order to detect the presence of an HPC2 allele predisposing an individual to cancer, a biological sample such as blood is prepared and analyzed for the presence or absence of susceptibility alleles of HPC2. In order to detect the presence of neoplasia, the progression toward malignancy of a precursor lesion, or as a prognostic indicator, a biological sample of the lesion is prepared and analyzed for the presence or absence of mutant alleles of HPC2. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant HPC2 sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for cancer susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 17. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; Mifflin, 1989; U.S. Pat. No. 4,868,105, and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes see Jablonski et al., 1986.

Two-step label amplification methodologies are known in the art. These assays work on the principle that a small ligand (such as digoxigenin, biotin, or the like) is attached to a nucleic acid probe capable of specifically binding HPC2. Allele specific probes are also contemplated within the scope of this example and exemplary allele specific probes include probes encompassing the predisposing or potentially predisposing mutations summarized in Table 8 of this patent application.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et at., 1977 and Nguyen et al., 1992.

It is also contemplated within the scope of this invention that the nucleic acid probe assays of this invention will employ a cocktail of nucleic acid probes capable of detecting HPC2. Thus, in one example to detect the presence of HPC2 in a cell sample, more than one probe complementary to HPC2 is employed and in particular the number of different probes is alternatively 2, 3, or 5 different nucleic acid probe sequences. In another example, to detect the presence of mutations in the HPC2 gene sequence in a patient, more than one probe complementary to HPC2 is employed where the cocktail includes probes capable of binding to the allele-specific mutations identified in populations of patients with alterations in HPC2. In this embodiment, any number of probes can be used, and will preferably include probes corresponding to the major gene mutations identified as predisposing an individual to prostate cancer.

Methods of Use: Peptide Diagnosis and Diagnostic Kits

The neoplastic condition of lesions can also be detected on the basis of the alteration of wild-type HPC2 polypeptide. Such alterations can be determined by sequence analysis in accordance with conventional techniques. More preferably, antibodies (polyclonal or monoclonal) are used to detect differences in, or the absence of, HPC2 peptides. The antibodies may be prepared as discussed above under the heading "Antibodies" and as further shown in Examples 9 and 10. Other techniques for raising and purifying antibodies are well known in the art and any such techniques may be chosen to achieve the preparations claimed in this invention. In a preferred embodiment of the invention, antibodies will immunoprecipitate HPC2 proteins from solution as well as react with HPC2 protein on Western or immunoblots of polyacrylamide gels. In another preferred embodiment, antibodies will detect HPC2 proteins in paraffin or frozen tissue sections, using immunocytochemical techniques.

Preferred embodiments relating to methods for detecting HPC2 or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al. in U.S. Pat. Nos. 4,376,110 and 4,486,530, hereby incorporated by reference, and exemplified in Example 12.

Methods of Use: Drug Screening

This invention is particularly useful for screening compounds by using the HPC2 polypeptide or binding fragment thereof in any of a variety of drug screening techniques.

The HPC2 polypeptide or fragment employed in such a test may either be free in solution, affixed to a solid support, or borne on a cell surface. One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between an HPC2 polypeptide or fragment and the agent being tested, or examine the degree to which the formation of a complex between an HPC2 polypeptide or fragment and a known ligand is interfered with by the agent being tested.

Thus, the present invention provides methods of screening for drugs comprising contacting such an agent with an HPC2 polypeptide or fragment thereof and assaying (i) for the presence of a complex between the agent and the HPC2 polypeptide or fragment, or (ii) for the presence of a complex between the HPC2 polypeptide or fragment and a ligand, by methods well known in the art. In such competitive binding assays the HPC2 polypeptide or fragment is typically labeled. Free HPC2 polypeptide or fragment is separated from that present in a protein:protein complex, and the amount of free (i.e., uncomplexed) label is a measure of the binding of the agent being tested to HPC2 or its interference with HPC2:ligand binding, respectively. One may also measure the amount of bound, rather than free, HPC2. It is also possible to label the ligand rather than the HPC2 and to measure the amount of ligand binding to HPC2 in the presence and in the absence of the drug being tested.

Another technique for drug screening provides high throughput screening for compounds having suitable binding affinity to the HPC2 polypeptides and is described in detail in Geysen (published PCT WO 84/03564). Briefly stated, large numbers of different small peptide test compounds are synthesized on a solid substrate, such as plastic pins or some other surface. The peptide test compounds are reacted with HPC2 polypeptide and washed. Bound HPC2 polypeptide is then detected by methods well known in the art.

Purified HPC2 can be coated directly onto plates for use in the aforementioned drug screening techniques. However, non-neutralizing antibodies to the polypeptide can be used to capture antibodies to immobilize the HPC2 polypeptide on the solid phase.

This invention also contemplates the use of competitive drug screening assays in which neutralizing antibodies capable of specifically binding the HPC2 polypeptide compete with a test compound for binding to the HPC2 polypeptide or fragments thereof. In this manner, the antibodies can be used to detect the presence of any peptide which shares one or more antigenic determinants of the HPC2 polypeptide.

A further technique for drug screening involves the use of host eukaryotic cell lines or cells (such as described above) which have a nonfunctional HPC2 gene. These host cell lines or cells are defective at the HPC2 polypeptide level. The host cell lines or cells are grown in the presence of drug compound. The rate of growth of the host cells is measured to determine if the compound is capable of regulating the growth of HPC2 defective cells.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel et al., 1993; Fields and Song, 1989; Chevray and Nathans, 1992; Lee et al., 1995). This system may be used as a coarse screen prior to testing a substance for actual ability to modulate activity of the polypeptide. Alternatively, the screen could be used to screen test substances for binding to an HPC2 specific binding partner, or to find mimetics of an HPC2 polypeptide.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., HPC2 polypeptide) or, for example, of the HPC2-receptor or ligand complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., HPC2 polypeptide) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved HPC2 polypeptide activity or stability or which act as inhibitors, agonists, antagonists, etc. of HPC2 polypeptide activity. By virtue of the availability of cloned HPC2 sequences, sufficient amounts of the HPC2 polypeptide may be made available to perform such analytical studies as x-ray crystallography. In addition, the knowledge of the HPC2 protein sequence provided herein will guide those employing computer modeling techniques in place of, or in addition to x-ray crystallography.

Following identification of a substance which modulates or affects polypeptide activity, the substance may be investigated further. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment of prostate cancer, use of such a substance in the manufacture of a composition for administration, e.g., for treatment of prostate cancer, and a method of making a pharmaceutical composition comprising admixing such a substance with a pharmaceutically acceptable excipient, vehicle or carrier, and optionally other ingredients.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Methods of Use: Gene Therapy

According to the present invention, a method is also provided of supplying wild-type HPC2 function to a cell which carries mutant HPC2 alleles. Supplying such a function should suppress neoplastic growth of the recipient cells. The wild-type HPC2 gene or a part of the gene may be introduced into the cell in a vector such that the gene remains extrachromosomal. In such a situation, the gene will be expressed by the cell from the extrachromosomal location. If a gene fragment is introduced and expressed in a cell carrying a mutant HPC2 allele, the gene fragment should encode a part of the HPC2 protein which is required for non-neoplastic growth of the cell. More preferred is the situation where the wild-type HPC2 gene or a part thereof is introduced into the mutant cell in such a way that it recombines with the endogenous mutant HPC2 gene present in the cell. Such recombination requires a double recombination event which results in the correction of the HPC2 gene mutation. Vectors for introduction of genes both for recombination and for extrachromosomal maintenance are known in the art, and any suitable vector may be used. Methods for introducing DNA into cells such as electroporation, calcium phosphate coprecipitation and viral transduction are known in the art, and the choice of method is within the competence of the practitioner. Cells transformed with the wild-type HPC2 gene can be used as model systems to study cancer remission and drug treatments which promote such remission.

As generally discussed above, the HPC2 gene or fragment, where applicable, may be employed in gene therapy methods in order to increase the amount of the expression products of such genes in cancer cells. Such gene therapy is particularly appropriate for use in both cancerous and pre-cancerous cells, in which the level of HPC2 polypeptide is absent or diminished compared to normal cells. It may also be useful to increase the level of expression of a given HPC2 gene even in those tumor cells in which the mutant gene is expressed at a "normal" level, but the gene product is not fully functional.

Gene therapy would be carried out according to generally accepted methods, for example, as described by Friedman (1991) or Culver (1996). Cells from a patient's tumor would be first analyzed by the diagnostic methods described above, to ascertain the production of HPC2 polypeptide in the tumor cells. A virus or plasmid vector (see further details below), containing a copy of the HPC2 gene, linked to expression control elements and capable of replicating inside the tumor cells, is prepared. Alternatively, the vector may be replication deficient and is replicated in helper cells for use in gene therapy. Suitable vectors are known, such as disclosed in U.S. Pat. No. 5,252,479 and PCT published application WO 93/07282 and U.S. Pat. Nos. 5,691,198; 5,747,469; 5,436,146 and 5,753,500. The vector is then injected into the patient, either locally at the site of the tumor or systemically (in order to reach any tumor cells that may have metastasized to other sites). If the transfected gene is not permanently incorporated into the genome of each of the targeted tumor cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovaviruses, e.g., SV40 (Madzak et al., 1992), adenovirus (Berkner, 1992; Berkner et al, 1988; Gorziglia and Kapikian, 1992; Quantin et al, 1992; Rosenfeld et al., 1992; Wilkinson and Akrigg, 1992; Stratford-Perricaudet et al., 1990; Schneider et al, 1998), vaccinia virus (Moss, 1992; Moss, 1996), adeno-associated virus (Muzyczka, 1992; Ohi et at, 1990; Russell and Hirata, 1998), herpes viruses including HSV and EBV (Margolskee, 1992; Johnson et al., 1992; Fink et at, 1992; Breakefield and Geller, 1987; Freese et al, 1990; Fink et al., 1996), lentiviruses (Naldini et al., 1996), Sindbis and Semliki Forest virus (Berglund et al., 1993), and retroviruses of avian (Bandyopadhyay and Temin, 1984; Petropoulos et al., 1992), murine (Miller, 1992; Miller et al., 1985; Sorge et al., 1984; Mann and Baltimore, 1985; Miller et al, 1988), and human origin (Shimada et al, 1991; Helseth et al, 1990; Page et al., 1990; Buchschacher and Panganiban, 1992). Most human gene therapy protocols have been based on disabled murine retroviruses, although adenovirus and adeno-associated virus are also being used.

Nonviral gene transfer methods known in the art include chemical techniques such as calcium phosphate coprecipitation (Graham and van der Eb, 1973; Pellicer et al, 1980); mechanical techniques, for example microinjection (Anderson et al., 1980; Gordon et al, 1980; Brinster et al, 1981; Costantini and Lacy, 1981); membrane fusion-mediated transfer via liposomes (Felgner et al, 1987; Wang and Huang, 1989; Kaneda et al, 1989; Stewart et al., 1992; Nabel et al, 1990; Lim et al, 1991); and direct DNA uptake and receptor-mediated DNA transfer (Wolff et al., 1990; Wu et at, 1991; Zenke et al, 1990; Wu et al., 1989; Wolff et al, 1991; Wagner et al., 1990; Wagner et al., 1991; Cotten et al., 1990; Curiel et al., 1991; Curiel et al., 1992). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged. For other techniques for the delivery of adenovirus based vectors see Schneider et al. (1998) and U.S. Pat. Nos. 5,691,198; 5,747,469; 5,436,146 and 5,753,500.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes HPC2, expression will produce HPC2. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

Gene transfer techniques which target DNA directly to prostate tissues, e.g., epithelial cells of the prostate, are preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. One appropriate receptor/ligand pair may include the estrogen receptor and its ligand, estrogen (and estrogen analogues). These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy involves two steps which can be performed singly or jointly. In the first step, prepubescent females who carry an HPC2 susceptibility allele are treated with a gene delivery vehicle such that some or all of their mammary ductal epithelial precursor cells receive at least one additional copy of a functional normal HPC2 allele. In this step, the treated individuals have reduced risk of prostate cancer to the extent that the effect of the susceptible allele has been countered by the presence of the normal allele. In the second step of a preventive therapy, predisposed young females, in particular women who have received the proposed gene therapeutic treatment, undergo hormonal therapy to mimic the effects on the prostate of a full term pregnancy.

Methods of Use: Peptide Therapy

Peptides which have HPC2 activity can be supplied to cells which carry mutant or missing HPC2 alleles. Protein can be produced by expression of the cDNA sequence in bacteria, for example, using known expression vectors. Alternatively, HPC2 polypeptide can be extracted from HPC2-producing mammalian cells. In addition, the techniques of synthetic chemistry can be employed to synthesize HPC2 protein. Any of such techniques can provide the preparation of the present invention which comprises the HPC2 protein. Preparation is substantially free of other human proteins. This is most readily accomplished by synthesis in a microorganism or in vitro.

Active HPC2 molecules can be introduced into cells by microinjection or by use of liposomes, for example. Alternatively, some active molecules may be taken up by cells, actively or by diffusion. Extracellular application of the HPC2 gene product may be sufficient to affect tumor growth. Supply of molecules with HPC2 activity should lead to partial reversal of the neoplastic state. Other molecules with HPC2 activity (for example, peptides, drugs or organic compounds) may also be used to effect such a reversal. Modified polypeptides having substantially similar function are also used for peptide therapy.

Methods of Use: Transformed Hosts

Similarly, cells and animals which carry a mutant HPC2 allele can be used as model systems to study and test for substances which have potential as therapeutic agents. The cells are typically cultured epithelial cells. These may be isolated from individuals with HPC2 mutations, either somatic or germline. Alternatively, the cell line can be engineered to carry the mutation in the HPC2 allele, as described above. After a test substance is applied to the cells, the neoplastically transformed phenotype of the cell is determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant HPC2 alleles, usually from a second animal species, as well as insertion of disrupted homologous genes. Alternatively, the endogenous HPC2 gene(s) of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992) to produce knockout or transplacement animals. A transplacement is similar to a knockout because the endogenous gene is replaced, but in the case of a transplacement the replacement is by another version of the same gene. After test substances have been administered to the animals, the growth of tumors must be assessed. If the test substance prevents or suppresses the growth of tumors, then the test substance is a candidate therapeutic agent for the treatment of the cancers identified herein. These animal models provide an extremely important testing vehicle for potential therapeutic products.

In one embodiment of the invention, transgenic animals are produced which contain a functional transgene encoding a functional HPC2 polypeptide or variants thereof. Transgenic animals expressing HPC2 transgenes, recombinant cell lines derived from such animals and transgenic embryos may be useful in methods for screening for and identifying agents that induce or repress function of HPC2. Transgenic animals of the present invention also can be used as models for studying indications such as disease.

In one embodiment of the invention, a HPC2 transgene is introduced into a non-human host to produce a transgenic animal expressing a human or murine HPC2 gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous HPC2 by homologous recombination between the transgene and the endogenous gene; or the endogenous gene may be eliminated by deletion as in the preparation of "knock-out" animals. Typically, a HPC2 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress HPC2 or express a mutant form of the polypeptide. Alternatively, the absence of a HPC2 in "knock-out" mice permits the study of the effects that loss of HPC2 protein has on a cell in vivo. Knock-out mice also provide a model for the development of HPC2-related cancers.

Methods for producing knockout animals are generally described by Shastry (1995, 1998) and Osterrieder and Wolf (1998). The production of conditional knockout animals, in which the gene is active until knocked out at the desired time is generally described by Feil et al. (1996), Gagneten et al. (1997) and Lobe and Nagy (1998). Each of these references is incorporated herein by reference.

As noted above, transgenic animals and cell lines derived from such animals may find use in certain testing experiments. In this regard, transgenic animals and cell lines capable of expressing wild-type or mutant HPC2 may be exposed to test substances. These test substances can be screened for the ability to reduce overepression of wild-type HPC2 or impair the expression or function of mutant HPC2.

Pharmaceutical Compositions and Routes of Administration

The HPC2 polypeptides, antibodies, peptides and nucleic acids of the present invention can be formulated in pharmaceutical compositions, which are prepared according to conventional pharmaceutical compounding techniques. See, for example, Remington's Pharmaceutical Sciences 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in Reminton's Pharmaceutical Sciences.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731A and WO 90/07936.

The identification of the association between the HPC2 gene mutations prostate cancer permits the early presymptomatic screening of individuals to identify those at risk for li; developing prostate cancer. To identify such individuals, HPC2 alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO), dot blot analysis and PCR-SSCP analysis. Also useful is the recently developed technique of DNA microchip technology. For example, either (1) the nucleotide sequence of both the cloned alleles and normal HPC2 gene or appropriate fragment (coding sequence or genomic sequence) are determined and then compared, or (2) the RNA transcripts of the HPC2 gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the HPC2 gene in an individual to be tested are cloned using conventional techniques. For example, a blood sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences of the clones are then determined and compared to the normal HPC2 gene.

Alternatively, polymerase chain reactions (PCRs) are performed with primer pairs for the region or the exons of the HPC2 gene. PCRs can also be performed with primer pairs based on any sequence of the normal HPC2 gene. For example, primer pairs for one of the introns can be prepared and utilized. Finally, RT-PCR can also be performed on the mRNA. The amplified products are then analyzed by single stranded conformation polymorphisms (SSCP) using conventional techniques to identify any differences and these are then sequenced and compared to the normal gene sequence.

Individuals can be quickly screened for common HPC2 gene variants by amplifying the individual s DNA using suitable primer pairs and analyzing the amplified product, e.g., by dot-blot hybridization using allele-specific oligonucleotide probes.

The second method employs RNase A to assist in the detection of differences between the normal HPC2 gene and defective genes. This comparison is performed in steps using small (~500 bp) restriction fragments of the HPC2 gene as the probe. First, the HPC2 gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing inserts of the HPC2 gene fragments are transcribed in vitro using the SP6 transcription system, well known in the art, in the presence of $[\alpha-^{32}P]GTP$, generating radiolabeled RNA transcripts of both strands of the gene.

Individually, these RNA transcripts are used to form heteroduplexes with the allelic DNA using conventional techniques. Mismatches that occur in the RNA:DNA heteroduplex, owing to sequence differences between the HPC2 fragment and the HPC2 allele subclone from the individual, result in cleavage in the RNA strand when treated with RNase A. Such mismatches can be the result of point mutations or small deletions in the individual's allele. Cleavage of the RNA strand yields two or more small RNA fragments, which run faster on the denaturing gel than the RNA probe itself.

Any differences which are found, will identify an individual as having a molecular variant of the HPC2. These variants can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

Genetic testing will enable practitioners to identify individuals at risk prostate cancer, at, or even before, birth. Presymptomatic diagnosis of these epilepsies will enable prevention of these disorders.

EXAMPLES

The present invention is further detailed in the following Examples, which are offered by way of illustration and are not intended to limit the invention in any manner. Standard techniques well known in the art or the techniques specifically described below are utilized.

Example 1

Genetic Localization of HPC2

A set of high risk prostate cancer kindreds has been collected in Utah since 1990 for the purpose of localization of prostate cancer susceptibility loci. In February 1996, linkage analysis of data from a genome scan performed on a subset of the families noted evidence for linkage with markers on chromosome 17p. Subsequent analysis of more markers in this region of chromosome 17p in a larger set of families has led to strong linkage evidence for a susceptibility gene.

TABLE 1

Chromosome 17p two-point linkage evidence

| Marker | 17p map position | Heterogeneity Lod Score |
| --- | --- | --- |
| D17S786 | 20.0 | 4.21 |
| Myr 0022 | 25.5 | 3.99 |
| Myr 0088 | 27.0 | 3.46 |
| D17S947 | 31.6 | 2.32 |
| Myr 0084 | 31.9 | 3.02 |
| Myr 0079 | 32.0 | 0.99 |
| D17S805 | 43.6 | 2.25 |

The study of specific kindreds with strong evidence of linkage to chromosome 17p allows the definition of a most likely region for the susceptibility locus by identifying the smallest inherited piece of chromosome 17p shared by the prostate cancer cases in the kindred. The minimal genetically defined region is based on a telomeric recombinant in kindred 4325 and a centromeric recombinant in kindred 4320. Kindred 4325 was ascertained from a sibship of early onset prostate cancer cases. There are 6 affected brothers in this family, one of whom also has an affected son. Five of the 6 affected brothers, and the affected son, all share the same piece of chromosome 17p from somewhere below marker myr0065 down to and including marker D17S805. Kindred 4320 was also ascertained form a sibship of early onset prostate cancer cases. In this kindred 3 affected brothers and an affected nephew share a piece of chromosome 17p from D17S786 down to and including myr0084. Together, the kindred 4325 and kindred 4320 recombinants define a minimal region of about 1 megabase (FIG. 2A); this localization is well supported by a larger set of recombinants in both directions.

Example 2

Contig Assembly and Genomic Sequencing in the Minimal Genetically Defined HPC2 Region Contig assembly. Given a genetically defined interval flanked by meiotic recombinants, one needs to generate a contig of genomic clones that spans that interval. Publicly available resources, such as the Whitehead integrated maps of the human genome (e.g., the WICGR Chr 17 map) provide aligned chromosome maps of genetic markers, other sequence tagged sites (STSs), radiation hybrid map data, and CEPH yeast artificial chromosome (YAC) clones.

Figure 2A:
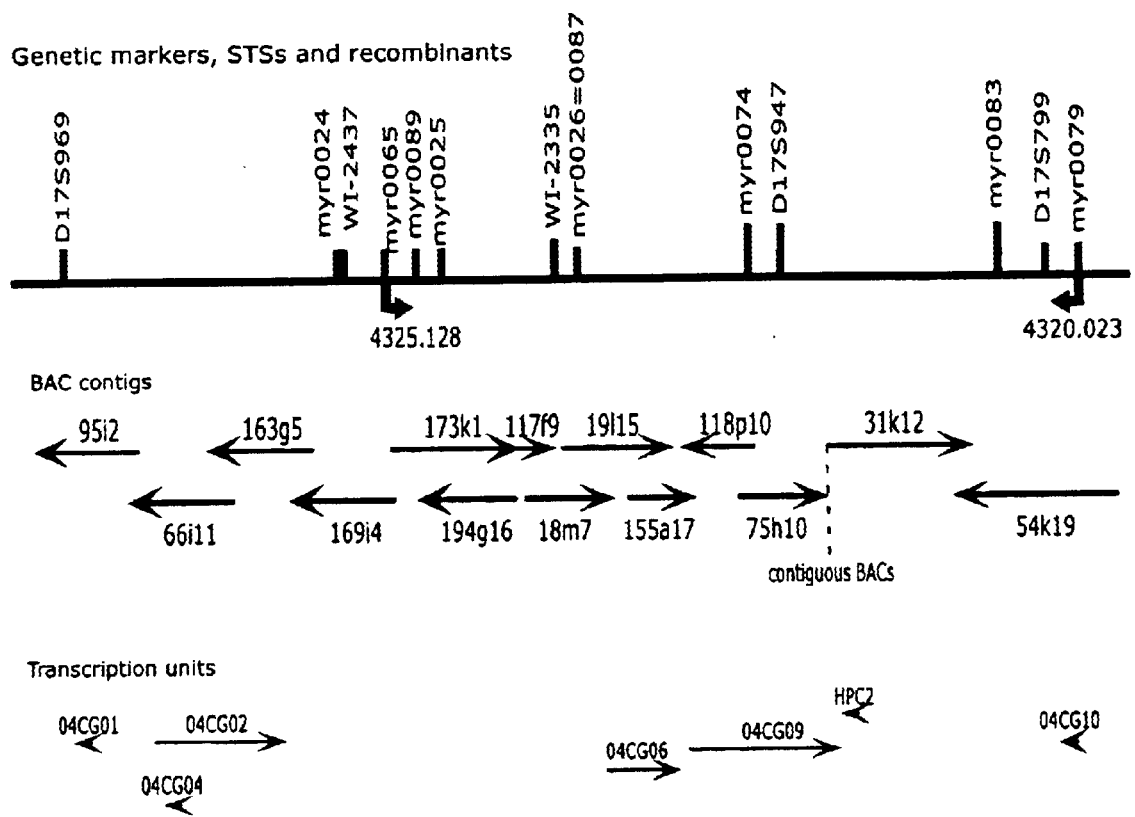
FIGS. 2A–B are diagrams showing the order of genetic markers and recombinant boundaries neighboring HPC2, a schematic map of BACs spanning the HPC2 region, a schematic map of transcription units within the HPC2 region, and two diagrams of the HPC2 transcription unit showing the locations of the exons of HPC2 relative to the BAC to which it maps and relative to each other. The individual exons are numbered.
Figure 2B:
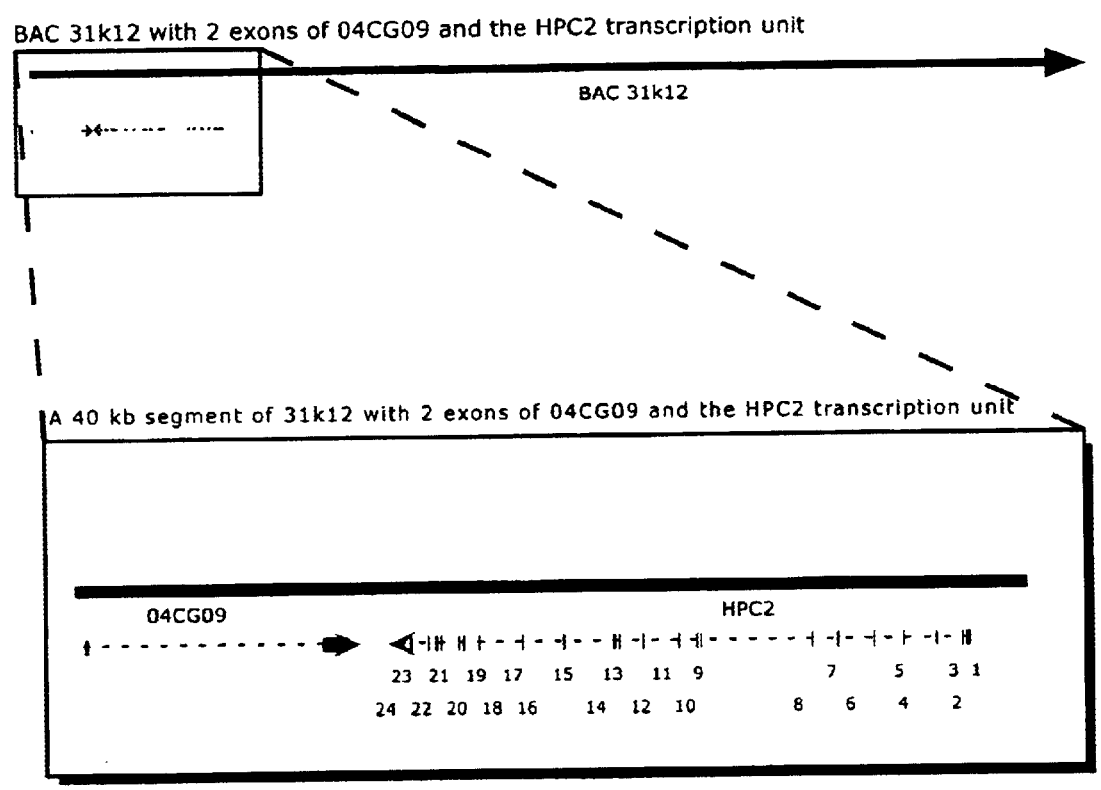

Oligonucleotide primer pairs for the markers located in the interval were synthesized and used to screen libraries of bacterial artificial chromosomes (BACs) to identify BACs in the region. The initial set of markers used was D17S969, WI-2437, WI2335, D17S947, and D17S799 (FIG. 2A). BACs identified with these markers were end-sequenced. PCR primers designed from those end sequences were used as markers to arrange the initial BACs into contigs. The outermost marker from each contig was used in successive rounds of BAC library screening, eventually enabling the completion of a BAC clone contig that spanned the genetically defined interval. A set of overlapping but non-redundant BAC clones that spanned this interval (FIG. 2A) was then selected for use in subsequent molecular cloning protocols such as genomic sequencing.

Genomic sequencing. Given a tiling path of BAC clones across a defined interval, one useful gene finding strategy is to generate an almost complete genomic sequence of that interval. Two types of random genomic clone sublibraries were prepared from each BAC on the tiling path; these were Sau 3A partial digest libraries with inserts in the 5 to 8 kb size range, and random shear libraries with inserts in the 1.0 to 1.5 kb size range. Plasmid DNA from individual clones from the Sau 3A sublibraries sufficient in number to generate an, on average, 1× redundant sequence of each BAC was prepared using an Autogen robotic plasmid preparation machine (Integrated Separation Systems). Insert DNA from individual clones from the random shear sublibraries sufficient in number to generate an, on average, 5× redundant sequence of each BAC, was prepared by PCR with vector primers directly from aliquots of bacterial cultures of each individual clone. The resulting DNA templates were subjected to DNA sequencing from both ends with M13 forward or reverse fluorescent dye-labeled primers on ABI 377 sequencers.

These sequences were assembled into sequence contigs using the program Acem.bly (Thierry-Mieg et al., 1995; Durbin and Thierry-Mieg, 1991). The genomic sequence contigs were placed in a Genetic Data Environment (GDE) (Smith et al., 1994) local database for subsequent similarity searches. Similarities among genomic DNA sequences and GenBank entries—both DNA and protein—were identified using BLAST (Altschul et al., 1990). The DNA sequences were also characterized with respect to short period repeats, CpG content, and long open reading frames.

Example 3

Sequence Assembly of the Human HPC2 Gene

A BLAST search of genomic sequences from BAC 31k12 against dbEST identified two independent sets of human ESTs that, when parsed across the BAC 31k12 genomic sequences, revealed the presence of two independent multi-exon candidate genes, 04CG09 and the HPC2 gene (FIG. 2A). A subset of the EST sequences assigned to HPC2 (Table 2) was assembled to produce a tentative partial cDNA sequence for the gene.

TABLE 2

Human ESTs used to assemble a tentative partial human HPC2 cDNA sequence

| EST Accession # | Exon Span |
| --- | --- |
| AA679618 | 1→6 |
| Z17886 | 4→8 |
| W37591 | 7→12 |
| AA310236 | 12→16 |
| R55841 | 15→19 |
| T34216 | 18→21 |
| AA634909 | 20→24 |
| AA504412 | 23→24 |
| R42795 | 24→polyA |

The individual exons of the human HPC2 gene were identified by parsing that tentative cDNA sequence across the BAC 31k12 genomic sequence (see schematics in FIGS. 2D and 2E). After we had identified the HPC2 gene, the MIT genome sequencing completely sequenced another BAC, 597m12, that also contains all of the exons of HPC2 (Genbank accession # AC005277) The sequence of the human HPC2 gene was corrected both by comparison of the sequences of the individual exons from the tentative cDNA assembly to the corresponding genomic sequences of BACs 31k12 and 597 m12, and by mutation screening the gene from a set of human genomic DNAs (see Example 5).

The original tentative human HPC2 cDNA sequence contained neither the start codon nor any of the 5' UTR. These were obtained by 5' RACE. Briefly, a biotinylated reverse primer, CA4cg07.BR2, was designed from the sequence of the third exon of the human HPC2 gene and used, along with the anchor primer 5ampA, for a first round of PCR amplification from human fetal liver cDNA that had been prepared such that the 5' ends of cDNA molecules are anchored with the sequence 5tag1. The resulting PCR products were captured on streptavidin paramagnetic particles (Dynal), washed, and used as template in a second round PCR amplification. A phosphorylated reverse primer, CA4cg07.PR2, was designed from the sequence of the second exon of the human HPC2 sequence and used, along with the nested phosphorylated anchor primer 5 ampB, for the second round PCR amplification. The resulting 5' RACE products were gel purified and sequenced with the primer CA4cg07.PR2 using dye-terminator chemistry and ABI 377 sequencers. Analysis of the sequences of these 5' RACE products yielded both the start codon and part of the 5' UTR including an in-frame stop codon (FIG. 3). Sequences of the primers used for 5' RACE are given in Table 4.

A full length human HPC2 cDNA was amplified from human head and neck cDNA using the primers CA4cg7.ATG and CA4cg7.TGA. The cDNA was ligated into the vector pGEM-T Easy (Promega) and transformed into *E. coli*. The sequence of the cDNA clone was confirmed by dye terminator sequencing on ABI 377 sequencers. Sequences of primers used to amplify the cDNA construct and confirm the sequence of the cDNA clone are also given in Table 3.

TABLE 3

Primers used in 5' RACE, cDNA cloning, and sequence confirmation of a full-length human HPC2 cDNA

|  | Sequence (SEQ ID NO:) |
|---|---|
| 5' RACE PRIMERS | |
| 5tag1 | CAG GAA TTC AGC ACA TAC TCA TTG TTC Agn n (29) |
| 5AmpA | CAG GAA TTC AGC ACA TAC TCA (30) |
| 5AmpB | (P)TT CAG CAC ATA CTC ATT GTT CA (31) |
| CA4cg07.BR2 | (B)TG AAC GCC TTC TCC ACA GT (32) |
| CA4cg07.PR2 | (P)GT ACC CGC TGC CAC CAC (33) |
| EXPRESSION CONSTRUCT PRIMERS | |
| CA4cg7.ATG | GCT AGG ATC CGC CAC CAT GTG GGC GCT TTG CTC (34) |
| CA4cg7.TGA | GCT ACT CGA GTC ACT GGG CTC TGA CCT TC (35) |
| SEQUENCING PRIMERS | |
| M13F20 | GTA AAA CGA CGG CCA GT (36) |
| M13R20 | GGA AAC AGC TAT GAC CAT G (37) |
| CA4cg7F1 | TGC GCA CGC GAG AGA AG (38) |
| CA4cg7R1 | CGC TTC TCT CGC GTG CG (39) |
| CA4cg7F2 | TCT AAT GTT GGG GGC TTA (40) |
| CA4cg7R2 | TAA GCC CCC AAC ATT AGA (41) |
| CA4cg7F3 | TGA AAA TGA GCC ACA CCT (42) |
| CA4cg7R3 | AGG TGT GGC TCA TTT TCA (43) |
| CA4cg7F4 | CAT TCA ACC CAT CTG TGA (44) |
| CA4cg7R4 | TCA CAG ATG GGT TGA ATG (45) |
| CA4cg7F5 | TGA ATG CCT CCT CAA GTA (46) |
| CA4cg7R5 | TAC TTG AGG AGG CAT TCA (47) |
| CA4cg7F6 | GCT ACT GGA CTG TGG TGA (48) |
| CA4cg7R6 | TCA CCA CAG TCC AGT AGC (49) |
| CA4cg7F7 | TGG AAG AGT TTC AGA CCT G (50) |
| CA4cg7R7 | CAG GTC TGA AAC TCT TCC A (51) |
| CA4cg7F8 | CGC AGG GAC GCA CCA TA (52) |
| CA4cg7R8 | GGT TGA ACT CGG AGA AGA (53) |
| CA4cg7F9 | CAA CTG GAA AAA TAC CTC G (54) |
| CA4cg7F10 | GCA GAG TCC AGA AAG GC (55) |
| CA4cg7F11 | AGA GGA AAC TTC TTG GTG C (56) |
| CA4cg7F12 | ACC AAG GAA AGG CAG ATG (57) |
| CA4cg7F13 | GTC AAC ATA GCC CCC GAC (58) |
| CA4cg7F14 | GGC TGC TGT GTT TGT GTC (59) |
| CA4cg7R14 | GAA GGC ATT TGG CAG GA (60) |
| CA4cg7F15 | TAT GAT TCC TGC CAA ATG (61) |
| CA4cg7R15 | TCC AGC CAG AGG TGT GC (62) |
| CA4cg7F16 | TGC GAG GCT CTG GTC CG (63) |
| CA4cg7R16 | GGG CAT TGT TGG AAA GTC (64) |
| CA4cg7F17 | TGT TTG CTG GCG ACA TC (65) | nn — the last 2 nucleotides of the anchor sequence 5tag1 are specific for each cDNA prep.
(P) indicates phosphate at the 5' end of the oligo
(B) indicates biotin at the 5' end of the oligo Example 4

Sequence Assembly of the Mouse HPC2 Gene

A BLAST search of the assembled HPC2 cDNA sequence against dbEST identified 5 mouse ESTs that derived from a very similar gene, the mouse ortholog of HPC2, Mm.HPC2; their accession numbers are listed in Table 4.

TABLE 4

Mouse ESTs used to assemble a tentative partial Mm.HPC2 cDNA sequence

| EST Accession # | Exon Span |
| --- | --- |
| AA563096 | 1→5 |
| AA518169 | 8→14 |
| AI132016 | 16→17 |
| AA184645 | 19→24 |
| AA174437 | 24→24 |

The original partial Mm.HPC2 cDNA sequence contained the start codon but little of the 5' UTR. More extensive 5' UTR sequence was obtained by 5' RACE. Briefly, a biotinylated reverse primer, m04cg07BR1, was designed from the sequence of the fourth exon of the mouse HPC2 gene and used, along with the anchor primer 5ampA, for a first round of PCR amplification from mouse embryo cDNA that had been prepared such that the 5' ends of cDNA molecules are anchored with the sequence 5tag1. The resulting PCR products were captured on streptavidin paramagnetic particles (Dynal), washed, and used as template in a second round PCR amplification. A phosphorylated reverse primer, m04cg07PR1, was designed from the sequence of the third exon of the mouse HPC2 sequence and used, along with the nested phosphorylated anchor primer 5ampB, for the second round PCR amplification. The resulting 5' RACE products were gel purified and sequenced with the primers m04cg07PR1 and m04cg07 exon2 rev using dye-terminator chemistry and ABI 377 sequencers. Analysis of the sequences of these 5' RACE products yielded both the start codon and part of the 5' UTR including an in-frame stop codon (FIG. 3). Sequences of the primers used for 5' RACE are given in Table 5.

More extensive 5' UTR sequence, sequence that may be from the promoter, and the sequences of intron 1 and intron 2 of of the mouse HPC2 gene were obtained by genomic sequencing. BAC 428n12 was obtained from a mouse genomic library by screening the library by PCR with a pair of primers (04CG7.m11f1 and 04CG7.m11r1, Table 5) derived from exon 11 of the mouse HPC2 cDNA sequence. A primer pair derived from the SP6 end sequence of BAC 428n12 (428n12.S6.F1 and 428n12.S6.F1, Table 5) was used to screen the mouse BAC library by PCR; several overlapping BACs, including BAC 199n11, were identified. BACs 428n12 and 199n11 were sequenced with a series of 13 sequencing primers (mcg7f1 to mcg7r7, Table 5) derived from mouse HPC2 cDNA dye-terminator chemistry and ABI 377 sequencers. A subset of these sequences were assembled into a genomic sequence contig extending from 280 bp upstream of the ATG start codon of exon 1 into exon 3.

A full length mouse HPC2 cDNA is amplified from mouse embryo, placenta, or fetal brain cDNA using the primers msCA4cg7.f out and msCA4cg7.r out The cDNA is reamplified with the primers msCA4cg7.ATG and msCA4cg7.TGA. The resulting PCR products are gel purified, ligated into the vector pGEM-T Easy (Promega), and transformed into E. coli. The sequence of the cDNA clone are confirmed dye terminator sequencing on ABI 377 sequencers. Sequences of primers in use to amplify the cDNA construct are also given in Table 5.

TABLE 5

Primers used in 5' RACE and cDNA cloning of a full-length mouse HPC2 cDNA

| | Sequence (SEQ ID NO:) |
| --- | --- |
| 5' RACE PRIMERS | |
| 5tag1 | CAG GAA TTC AGC ACA TAC TCA TTG TTC Agn n (66) |
| 5AmpA | CAG GAA TTC AGC ACA TAC TCA (67) |
| 5 Amp B | (P)TT CAG CAC ATA CTC ATT GTT CA (68) |
| m04cg07BR1 | (B)CA GAA CAC ATT TGG GAA GC (69) |
| m04cg07PR1 | (P)GA TGT TGT CCA AGC GAG C (70) |
| BAC library screening primers | |
| 04CG7.m11f1 | TGA CAC ACA GCA CCT GA (71) |
| 04CG7.m11r1 | GAA GAT GTC AGG GTG GA (72) |
| 428n12.S6.F1 | CAG GCA TAC CAC TAC AGA (73) |
| 428n12.S6.R1 | TAT CAA CTT CTA GGC AAG TG (74) |
| Genomic sequencing primers | |
| mcg7f1 | GCA CCA TGT CGC AGG GTT C (75) |
| mcg7r1 | GAA CCC TGC GAC ATG GTG C (76) |
| mcg7f2 | TCG CAG GGT TCG GCT CGT C (77) |
| mcg7r2 | AAC CCT GCG ACA TGG TGC G (78) |
| mcg7f3 | AAA GAC CCA CTG CGA CAC C (79) |
| mcg7r3 | GCA GGT GTC GCA GTG GGT C (80) |
| mcg7f4 | CCG AAC ACC GTG TAC CTG CA (81) |
| mcg7r4 | CAG GTA CAC GGT GTT CGG G (82) |
| mcg7f5 | GTC TTC TCG GAA TAC AAC AGG (83) |
| mcg7r5 | CTG TTG TAT TCC GAG AAG AC (84) |
| mcg7f6 | AAG GCG TCC AAC GAC TTA TG (85) |
| mcg7r6 | AGT CGT TGG ACG CCT TCT CC (86) |
| mcg7r7 | TCC GAG TCA GAA AGA TGT TG (87) |

TABLE 5-continued

Primers used in 5' RACE and cDNA cloning of a full-length mouse HPC2 cDNA

Sequence (SEQ ID NO:)

EXPRESSION CONSTRUCT PRIMERS

PRIMARY PCR

| | |
|---|---|
| msCA4cg7.f out | GCC TTG TCA GCC TGG TG (88) |
| msCA4cg7.r out | AGG AAG TGA GCA GAG CG (89) |

SECONDARY PCR

| | |
|---|---|
| msCA4cg7.ATG | GCT AAA GCT TGC CAC CAT GTG GGC GCT CCG CTC (90) |
| msCA4cg7.TGA | GCT ACT CGA GTC ACA CTC GCG CTC CTA (91) |

SEQUENCING PRIMERS

| | |
|---|---|
| m04cg07 exon2 rev | GCC TTC TCC GCA GTT A (92) | nn — the last 2 nucleotides of the anchor sequence 5tag1 are specific for each cDNA prep.
(P) indicates phosphate at the 5' end of the oligo
(B) indicates biotin at the 5' end of the oligo

Example 5

Mutation Screening of the Human HPC2 Gene

Using genomic DNAs from prostate kindred members, prostate cancer affecteds, and tumor cell lines as templates, nested PCR amplifications were performed to generate PCR products to screen for mutations in the HPC2 gene. The primers listed in Table 6 were used to amplify segments of the HPC2 gene. Using the outer primer pair for each amplicon (1A-1P, i.e., forward A and reverse P of amplicon 1), 10–20 ng of genomic DNA were subjected to a 25 cycle primary amplification, after which the PCR products were diluted 45-fold and reamplified using nested M13-tailed primers (1B-1Q, 1C-1R i.e., nested forward B and nested reverse Q of amplicon 1 or nested forward C and nested reverse R of amplicon 1) for another 23 cycles. In general, samples were amplified with Taq Platinum (Life Technologies) DNA polymerase; cycling parameters included an initial denaturation step at 95° C. for 3 min, followed by cycles of denaturation at 96° C. (12 s), annealing at 55° C. (15 s) and extension at 72° C. (30–60 s). After the PCR reactions, excess primers and deoxynucleotide triphosphates were digested with exonuclease I (United States Biochemicals) and shrimp alkaline phosphatase (Amersham). PCR products were sequenced with M13 forward or reverse fluorescent (Big Dye, ABI) dye-labeled primers on ABI 377 sequencers. Chromatograms were analyzed for the presence of polymorphisms or sequence aberrations in either the Macintosh program Sequencher (Gene Codes) or the Java program Mutscreen.

TABLE 6

Primers used to mutation screen the HPC2 gene from genomic DNA

| Exon/Primer name | Sequence (SEQ ID NO:) |
|---|---|
| HPC2 exon 1 | |
| ca4cg7.m1Anew | CCG CTT GAG ACG CTC TAG TAT (93) |
| ca4cg7.m1P | GCT CCG AAA GTG CTG ACA G (94) |
| ca4cg7.m1Bnew | GTT TTC CCA GTC ACG ACG TTT CTA TTG GAT GAG CAG CCT (95) |
| ca4cg7.m1Qnew | AGG AAA CAG CTA TGA CCA TGC CTG CGA TAT GGT GCG TC (96) |
| ca4cg7.m1C | GTT TTC CCA GTC ACG ACG CTC AGT TTT GGT GGA GAC G (97) |
| ca4cg7.m1Rnew | AGG AAA CAG CTA TGA CCA TGT GCC CCG ATG CTC AGA G (98) |
| HPC2 exons 2&3 | (primary) |
| ca4cg7.m2&23 A2 | AAT GGT GTC AGA GAG TTT ACA G (99) |
| ca4cg7.m2&23P | GCT ATT TGG GAG GCT GAG G (100) |
| HPC2 exon 2 | (nested) |
| ca4cg7.m2B | GTT TTC CCA GTC ACG ACG AAT GGT GTC AGA GAG TTT ACA G (101) |
| ca4cg7.m2Q | AGG AAA CAG CTA TGA CCA TGA ACA AGG ACC ACT TTT GCT AT (102) |
| HPC2 exon 3 | (nested) |
| ca4cg7.m23B | GTT TTC CCA GTC ACG ACG TTT ATA GCA AAA GTG GTC CTT G (103) |
| ca4cg7.m23Q | AGG AAA CAG CTA TGA CCA TGA GAC TTC CCA CCA GCC TC (104) |
| HPC2 exon 4 | |
| ca4.cg07.m24A | CCT TGC TGC TTC ACC CTA G (105) |
| ca4.cg07.m24P | TGC TTT ATA TGT GCT GCT ACG (106) |
| ca4.cg07.m24B | GTT TTC CCA GTC ACG ACG CAT CTT CCC TGG TTG TAC TTC (107) |
| ca4.cg07.m24Q | AGG AAA CAG CTA TGA CCA TCT GGA GGG CAG AAG ACT GAT (108) |

TABLE 6-continued

Primers used to mutation screen the HPC2 gene from genomic DNA

| Exon/Primer name | Sequence (SEQ ID NO:) |
|---|---|
| HPC2 exon 5 | |
| ca4cg7.m3A | CTA CAT TTG TTC AAC CAT AAC TG (109) |
| ca4cg7.m3P | GAT TTT GAG GTT TGA TGT TGA TG (110) |
| ca4cg7.m3B | GTT TTC CCA GTC ACG ACG CAT TTG TTC AAC CAT AAC TGC (111) |
| ca4cg7.m3Q | AGG AAA CAG CTA TGA CCA TAT TTG AGA GGT CAG GGC ATA (112) |
| HPC2 exon 6 | |
| ca4cg7.m4A | TCG TGT CAG ATT CCC ACC ATA (113) |
| ca4cg7.m4P | AGG CAT AAG TCA GAC ATC CGT (114) |
| ca4cg7.m4B | GTT TTC CCA GTC ACG ACG GTT ACT CTT CCC ACA CAT CTT C (115) |
| ca4cg7.m4Q | AGG AAA CAG CTA TGA CCA TCA CAG CAA GTG TTC AGT TTC TA (116) |
| HPC2 exon 7 | |
| ca4cg7.m5A | CAT TCC CAT GTA TGA ACG TCT (117) |
| ca4cg7.m5P | ATA GTA AGC CCA GGA AGA AGGA (118) |
| ca4cg7.m5B | GTT TTC CCA GTC ACG ACG CAT TCC CAT GTA TGA ACG TCT (119) |
| ca4cg7.m5Q | AGG AAA CAG CTA TGA CCA TCT ACA AGC ATT ACA AGG CAG AG (120) |
| HPC2 exon 8 | |
| ca4cg7.m6A | AGT GTC TTC AGC CTT TGT ATT G (121) |
| ca4cg7.m6P | ATC TGC TAT CTC TTC TTG TCT CA (122) |
| ca4cg7.m6B | GTT TTC CCA GTC ACG ACG ATC GGG TCA TAA TCA GTC TGT G (123) |
| ca4cg7.m6Q | AGG AAA CAG CTA TGA CCA TAT CTC TTC TTG TCT CAG GTA ACA (124) |
| HPC2 exons 9&10 | (primary) |
| ca4cg7.m7&8A | CTT CTG AAA GCA ATA AAC GCA T (125) |
| ca4cg7.m7&8P | GAT GTC CAA ACT GTT CCA CG (126) |
| HPC2 exon 9 | (nested) |
| ca4cg7.m7B | GTT TTC CCA GTC ACG ACG TAA AAC CAA CCT TCT TCA TTA G (127) |
| ca4cg7.m7Q | AGG AAA CAG CTA TGA CCA TAG CAA TGA TGG GAG CGA TG (128) |
| HPC2 exon 10 | (nested) |
| ca4cg7.m8B | GTT TTC CCA GTC ACG ACG GGC TTC TGG GGA CTC ACT G (129) |
| ca4cg7.m8Q | AGG AAA CAG CTA TGA CCA TCC TTC AAA AGT GGT GTC TGT AG (130) |
| HPC2 exon 11 | |
| ca4.cg07.m9A | GTA TCC ACA AAG AGA CCA GAA G (131) |
| ca4.cg07.m9P | CAC CAA CTA CCA ACA GTG ACT TA (132) |
| ca4.cg07.m9B | GTT TTC CCA GTC ACG ACG GCT CAC TGG ATA GGA TAT GTC AT (133) |
| ca4.cg07.m9Q | AGG AAA CAG CTA TGA CCA TCC AGA AAC ACA GCT CTT GCC (134) |
| HPC2 exon 12 | |
| ca4.cg07.m10A | GCT TGC CAG ATA CAG GAA TC (135) |
| ca4.cg07.m10P | ACA GAA AGT TTA GGC AGG TG (136) |
| ca4.cg07.m10B | GTT TTC CCA GTC ACG ACG ACG ATA CCC CTC CCT GGC T (137) |
| ca4.cg07.m10Q | AGG AAA CAG CTA TGA CCA TAC AGA AAG TTT AGG CAG GTG (138) |
| HPC2 exons 13&14 | (primary) |
| ca4.cg07.m11&12A | CCT CTC ACT CTT CCC AGC AC (139) |
| ca4.cg07.m11&12P | GGA GTA GGC TGC TTT TCT AAA T (140) |
| HPC2 exon 13 | (nested) |
| ca4.cg07.m11B | GTT TTC CCA GTC ACG ACG GAA CAC CTC ATC CTC ATT ACC A (141) |
| ca4.cg07.m11Q | AGG AAA CAG CTA TGA CCA TAA GAG ACA AAA CAC ATT CAT GG (142) |
| HPC2 exon 14 | (nested) |
| ca4.cg07.m12B | GTT TTC CCA GTC ACG ACG GTT TCC GCT GTA AGG TAG TGT (143) |
| ca4.cg07.m12Q | AGG AAA CAG CTA TGA CCA TCT GGA ACA TTT ACT ATG TGG CTA (144) |
| HPC2 exon 15 | |
| ca4.cg07.m13A | TGC TAG TGG GTA GAG GTC AG (145) |
| ca4.cg07.m13P | ACT GAA AGC CAG GTT AGA ATG (146) |
| ca4.cg07.m13B | GTT TTC CCA GTC ACG ACG ACC CTG TCC GTC ACC TGA G (147) |
| ca4.cg07.m13Q | AGG AAA CAG CTA TGA CCA TCC CAC CAG CAC TCC ACT TA (148) |
| HPC2 exon 16 | |
| ca4cg07.m14A | TGT GAA GAC GGG ATA ACC TGA (149) |
| ca4cg07.m14P | GAC AGG GCT TGA TAC CGCA (150) |
| ca4cg07.m14B | GTT TTC CCA GTC ACG ACG ATG CTG GCT CAC TTT TGA CC (151) |
| ca4cg07.m14Q | AGG AAA CAG CTA TGA CCA TGAC TGG TGA GTA CAG CAG GA (152) |

TABLE 6-continued

Primers used to mutation screen the HPC2 gene from genomic DNA

| Exon/Primer name | Sequence (SEQ ID NO:) |
|---|---|
| HPC2 exon 17 | |
| ca4.cg07.m15A | CCA GCC TTT GTG TAA GTC TAC (153) |
| ca4.cg07.m15P | TCT GGG CAA GTT TGG AAG C (154) |
| ca4.cg07.m15B | GTT TTC CCA GTC ACG ACG TCC AAA GCA GAC ATC AGC CTC (155) |
| ca4.cg07.m15Q | AGG AAA CAG CTA TGA CCA TGG AGG AAA AGA CGC AGC CA (156) |
| HPC2 exon 18 | |
| ca4.cg07.m16A | CGC TTT CTG CCT GTG ACA T (157) |
| ca4.cg07.m16P | TTC TGT CCT TCA GCC AAT GC (158) |
| ca4.cg07.m16B | GTT TTC CCA GTC ACG ACG TTA GAG GCT GGT GGG TGA C (159) |
| ca4.cg07.m16Q | AGG AAA CAG CTA TGA CCA TCA TCT CAA TAA AAA CTG GAG TGC (160) |
| HPC2 exon 19 | |
| ca4.cg07.m17A | CAC TTG ATG GGC GTT CTG AG (161) |
| ca4.cg07.m17P | TTC TGT CCT TCA GCC AAT GC (162) |
| ca4.cg07.m17B | GTT TTC CCA GTC ACG ACG TTC CAG CGG TTT ACA CAT CA (163) |
| ca4.cg07.m17Q | AGG AAA CAG CTA TGA CCA TTA CCC CAG TGT CCA CCT TG (164) |
| HPC2 exons 20&21 | (primary) |
| CA4CG7.m18&22A | GGG TTC TCC AGC CAA AGA CT (165) |
| CA4CG7.m18&22P | CTG AGT CTC CTG CCT CTG C (166) |
| HPC2 exon 20 | (nested) |
| ca4.cg07.m18B | GTT TTC CCA GTC ACG ACG GGG TTC TCC AGC CAA AGA CT (167) |
| ca4.cg07.m18Q | AGG AAA CAG CTA TGA CCA TGT GGG GCT GGA AGG CTC TG (168) |
| HPC2 exon 21 | (nested) |
| ca4.cg07.m22B | GTT TTC CCA GTC ACG ACG AAG AGG TAA GGG GCA CAG C (169) |
| ca4.cg07.m22Q | AGG AAA CAG CTA TGA CCA TCT GAG TCT CCT GCC TCT GC (170) |
| HPC2 exon 22 | |
| ca4.cg07.m19A | GCT GAG TGT TGA GAC CAG GA (171) |
| ca4.cg07.m19P | AGA CAA ACG ACG GCT GCT C (172) |
| ca4.cg07.m19B | GTT TTC CCA GTC ACG ACG TTG AGA CCA GGA AAC AGC AC (173) |
| ca4.cg07.m19Q | AGG AAA CAG CTA TGA CCA TGA GAG GAT GTG GGC GAC AA (174) |
| HPC2 exon 23 | |
| ca4.cg07.m20A | GGG AGA TGG TGC TGG CTA C (175) |
| ca4.cg07.m20P | CCT GGT TAG TGA TGG GTA GAT (176) |
| ca4.cg07.m20B | GTT TTC CCA GTC ACG ACG CAG GGT CTG TGC CAC TGT C (177) |
| ca4.cg07.m20Q | AGG AAA CAG CTA TGA CCA TCT CAG TGT GTA GAG TCC TGT C (178) |
| HPC2 exon 24 | splice acceptor and open reading frame |
| ca4.cg07.m21A | TTG ATT TTG AGA GCA TCT GGA C (179) |
| ca4.cg07.m21P | CTC GGA CAC TTA GAC CCA CTG (180) |
| ca4.cg07.m21B1 | GTT TTC CCA GTC ACG ACG TGC ATC CCT TCC AGC TCC T (181) |
| ca4.cg07.m21Q | AGG AAA CAG CTA TGA CCA TGA CAC ACA GCC TTC TGA GTT CA (182) |
| ca4.cg07.m21C | GTT TTC CCA GTC ACG ACG CCA CAC AGA GGA GCC ACA G (183) |
| ca4.cg07.m21R | AGG AAA CAG CTA TGA CCA TAC CAG TCC TAA GAG GCA TCT ATA (184) |
| HPC2 exon 24 | 3' untranslated region |
| ca4.cg07.m21.3'UTR A | CCA CAC AGA GGA GCC ACA G (185) |
| ca4.cg07.m21.3'UTR P | CCA GAG GTG CTC ACT ACG AC (186) |
| ca4.cg07.m21.3'UTR B | GTT TTC CCA GTC ACG ACG AGG TCA GAG CCC AGT GAA GAT (187) |
| ca4.cg07.m21.3'UTR Q | AGG AAA CAG CTA TGA CCA TCA TCT GCT TGC TTC CGT GTG (188) |
| ca4.cg07.m21.3'UTR C | GTT TTC CCA GTC ACG ACG TCA GGA TAG GTG GTA TGG AGC (189) |
| ca4.cg07.m21.3'UTR R | AGG AAA CAG CTA TGA CCA TCG GAC ACT TAG ACC CAC TGA T (190) |

TABLE 7

Sequence Variants

| Variant name | Sequence (SEQ ID NO:) | Coding effect* |
|---|---|---|
| C650T | AGACTCCGAGTYGAATGAAAATG (191) | Ser217Leu |
| A1560G | GGTGAGGGCACRTTTGGGCAGCT (192) | Thr520Thr |
| G1621A | GCACCCTGGCTRCTGTGTTTGTG (193) | Ala541Thr |
| 1641insG (normal) | GTGTCCCACCTG—CACGCAGATCA (194) | |
| (with insertion of G) | GTGTCCCACCTGGCACGCAGATCA (195) | frameshift |
| C1722T | AAGCCGCTTCAYCCTTTGCTGGT (196) | His574His |
| A1893G | GCTGTTGCGAACRTGTGATTTGGA (197) | Thr631Thr |

TABLE 7-continued

Sequence Variants

| Variant name | Sequence (SEQ ID NO:) | Coding effect* |
|---|---|---|
| C2632G | GAGGCTTGGGSTCCCACATAAG (198) | |
| C2687T | CCTGGCACAGCYGCGGGCCAGGA (199) | |
| G2801A | AATCCAGCAAARTGATTCCCTGC (200) | |
| IVS2 T-11C | Taaatgttttytcattcttag (201) | |
| IVS5 T-14C | Ttgctgttgtgyggttttcttgt (202) | |
| IVS10 23insGAT (normal) | ggttttcttgat—tcagcagttaca (203) | |
| (with insertion of GAT) | Ggttttcttgatgattcagcagttaca (204) | |
| IVS13 C15T | Gtgtctcagacyggccccttgtc (205) | |
| IVS14 A17T | Tgccatcttgawctaatggaatc (206) | |
| IVS14 T-8C | Cttctctctctycctgcagggat (207) | |
| IVS16 C41T | Catcaagggcaygtttacttttt (208) | |
| IVS19 C26G | Cagccttgcccsctgggctgttg (209) | |

*based on conceptual translation of the HPC2 ORF for each allele of the sequence variant.

In the course of mutation screening HPC2 from lymphocyte DNA collected from prostate cancer affecteds in our set of linked families, a frameshift mutation (1641insG) was detected in two affected brothers in kindred 4102. Individual 4102.001, diagnosed with prostate cancer at age 51, and his brother 4102.013, diagnosed with prostate cancer at age 46, both carry the frameshift. Further mutation screening in this kindred revealed that their mother, 4102.002, carries the frameshift. In addition, her maternal uncle 4102.053, diagnosed with prostate cancer at age 75 and deceased at age 76, also carried the frameshift.

The frameshift 1641insG throws translation of HPC2 out of frame following amino acid leucine547. Because the HPC2 protein shares significant sequence similarity with homologous proteins as evolutionarily distant as the E. coli elaC protein, and this region of shared sequence similarity extends over a segment of more than 180 amino acids downstream of leucine547, there is no doubt but that the frameshift 1641insG is deleterious to the function of the HPC2 protein.

Taken together, the observation that the frameshift HPC2 1641insG segregates with prostate cancer across three generations of kindred 4102, and the inference from shared sequence similarity that the framshift HPC2 1641 insG must be deleterious to the function of the HPC2 protein, establish that deleterious germline mutations in the HPC2 gene confer susceptibility to prostate cancer.

Example 6

Identification of HPC2-Interacting Proteins by Two-Hybrid Analysis

DNA fragments encoding all or portions of HPC2 are ligated to a two-hybrid DNA-binding domain vector such as pGBT.C such that the coding sequence of HPC2 is in-frame with coding sequence for the Gal4p DNA-binding domain. A plasmid that encodes a DNA-binding domain fusion to a fragment of HPC2 is introduced into the yeast reporter strain (such as J692) along with a 115 library of cDNAs fused to an activation domain. Transformants are spread onto 20–150 mm plates of selective media, such as yeast minimal media lacking leucine, tryptophan, and histidine, and containing 25 mM 3-amino-1,2,4-triazole. After one week incubation at 30° C., yeast colonies are assayed for expression of the lacZ reporter gene by beta-galactosidase filter assay. Colonies that both grow in the absence of histidine and are positive for production of beta-galactosidase are chosen for further characterization.

The activation domain plasmid is purified from positive colonies by the smash-and-grab technique. These plasmids are introduced into E. coli (e.g., DH10B (Gibco BRL) by electroporation and purified from E. coli by the alkaline lysis method. To test for the specificity of the interaction, specific activation domain plasmids are cotransformed into strain J692 with plasmids encoding various DNA-binding domain fusion proteins, including fusions to segments of HPC2 and human lamin C. Transformants from these experiments are assayed for expression of the HIS3 and lacZ reporter genes. Positives that express reporter genes with Hs HPC2 constructs and not with lamin C constructs encode bona fide HPC2-interacting proteins. These proteins are identified and characterized by sequence analysis of the insert of the appropriate activation domain plasmid.

Example 7

Identification of Orthologs of the Human HPC2 Gene

All species living on the Earth now are thought to have evolved from a single common ancestor that lived in the distant past, perhaps 3.5 to 4 billion years ago. This means that any pair of species must share a common ancestor species that lived at some time in the past. Admittedly, this view is a bit simplistic because, for instance, the nuclear genomes and mitochondrial genomes of eukaryotes are thought to have independent prokaryotic ancestries. During the evolution of an ancestral species into two or more extant daughter species, the genes present in the genome of the ancestral species evolve into the genes present in the genomes of the daughter species. The evolutionary history of the genes present in the daughter species can be quite complex because the individual genes can evolve through a diverse set of processes including nucleotide substitution, insertion, deletion, gene duplication, gene conversion, lateral transfer, etc. Even so, the evolutionary history of related genes in related organisms can often be sorted out, especially if the pair/set of species share a relatively recent common ancestor or if the genes being analyzed evolved primarily through nucleotide substitutions and/or small insertions 1 L and/or small deletions, but not gene duplications or gene conversions. When, upon analysis, it appears that a single gene in one species and a single gene in another species have evolved from a single gene in a common ancestor species, those genes are termed orthologs.

Knowledge of the identity of genes orthologous to disease-related human genes can often be quite useful.

Example 8

Analysis of the HPC2 Gene

The structure and function of HPC2 gene are determined according to the following methods.

Biological Studies. Mammalian expression vectors containing HPC2 cDNA are constructed and transfected into appropriate prostate carcinoma cells with lesions in the gene. Wild-type HPC2 cDNA as well as altered HPC2 cDNA are utilized. The altered HPC2 cDNA can be obtained from altered HPC2 alleles or produced as described below. Phenotypic reversion in cultures (e.g., cell morphology, doubling time, anchorage-independent growth) and in animals (e.g., tumorigenicity) is examined. The studies will employ both wild-type and mutant forms of the gene.

Molecular Genetics Studies. In vitro mutagenesis is performed to construct deletion mutants and missense mutants (by single base-pair substitutions in individual codons and alanine scanning mutagenesis). The mutants are used in biological, biochemical and biophysical studies.

Mechanism Studies. The ability of HPC2 protein to bind to known and unknown DNA sequences is examined. Its ability to transactivate promoters is analyzed by transient reporter expression systems in mammalian cells. Conventional procedures such as particle-capture and yeast two-hybrid system are used to discover and identify any functional partners. The nature and functions of the partners are characterized. These partners in turn are targets for drug discovery.

Structural Studies. Recombinant proteins are produced in E. coli, yeast, insect and/or mammalian cells and are used in crystallographical and NMR studies. Molecular modeling of the proteins is also employed. These studies facilitate structure-driven drug design.

Example 9

Generation of Polyclonal Antibody Against HPC2

Segments of HPC2 coding sequence are expressed as fusion protein in E. coli. The overexpressed proteins are purified by gel elution and used to immunize rabbits and mice using a procedure similar to the one described by Harlow and Lane, 1988. This procedure has been shown to generate Abs against various other proteins (for example, see Kraemer, et al., 1993).

Briefly, a stretch of HPC2 coding sequence was cloned as a fusion protein in plasmid PET5A (Novagen, Inc., Madison, Wis.). The HPC2 incorporated sequences might include SEQ ID NOs:1, 3 or 28 or portions thereof. After induction with IPTG, the overexpression of a fusion protein with the expected molecular weight is verified by SDS/PAGE. Fusion proteins are purified from the gel by electroelution. The identification of the protein as the HPC2 fusion product is verified by protein sequencing at the N-terminus. Next, the purified protein is used as immunogen in rabbits. Rabbits are immunized with 100 μg of the protein in complete Freund's adjuvant and boosted twice in 3 week intervals, first with 100 μg of immunogen in incomplete Freund's adjuvant followed by 100 μg of immunogen in PBS. Antibody containing serum is collected two weeks thereafter.

This procedure can be repeated to generate antibodies against mutant forms of the HPC2 protein. These antibodies, in conjunction with antibodies to wild type HPC2, are used to detect the presence and the relative level of the mutant forms in various tissues and biological fluids.

Example 10

Generation of Monoclonal Antibodies Specific for HPC2

Monoclonal antibodies are generated according to the following protocol. Mice are immunized with immunogen comprising intact HPC2 or HPC2 peptides (wild type or mutant) conjugated to keyhole limpet hemocyanin using glutaraldehyde or EDC as is well known.

The immunogen is mixed with an adjuvant. Each mouse receives four injections of 10 to 100 μg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988. Cells are plated at a density of $2 \times 10^5$ cells/well in 96 well tissue culture plates. Individual wells are examined for growth and the supernatants of wells with growth are tested for the presence of HPC2 specific antibodies by ELISA or RIA using wild type or mutant HPC2 target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

Example 11

Isolation of HPC2 Binding Peptides

Peptides that bind to the HPC2 gene product are isolated from both chemical and phage-displayed random peptide libraries as follows.

Fragments of the HPC2 gene product are expressed as GST and His-tag fusion proteins in both E. coli and SF9 cells. The fusion protein is isolated using either a glutathione matrix (for GST fusions proteins) or nickel chelation matrix (for His-tag fusion proteins). This target fusion protein preparation is either screened directly as described below, or eluted with glutathione or imidizole. The target protein is immobilized to either a surface such as polystyrene; or a resin such as agarose; or solid supports using either direct absorption, covalent linkage reagents such as glutaraldehyde, or linkage agents such as biotin-avidin.

Two types of random peptide libraries of varying lengths are generated: synthetic peptide libraries that may contain derivatized residues, for example by phosphorylation or myristylation, and phage-displayed peptide libraries which may be phosphorylated. These libraries are incubated with immobilized HPC1 gene product in a variety of physiological buffers. Next, unbound peptides are removed by repeated washes, and bound peptides recovered by a variety of elution reagents such as low or high pH, strong denaturants, glutathione, or imidizole. Recovered synthetic peptide mixtures are sent to commercial services for peptide microsequencing to identify enriched residues. Recovered phage are amplified, rescreened, plaque purified, and then sequenced to determined the identity of the displayed peptides.

Use of HPC1 binding peptides. Peptides identified from the above screens are synthesized in larger quantities as biotin conjugates by commercial services. These peptides are used in both solid and solution phase competition assays with HPC1 and its interacting partners identified in yeast 2-hybrid screens. Versions of these peptides that are fused to membrane-permeable motifs (Lin et al., 1995; Rojas et al., 1996) will be chemically synthesized, added to cultured cells and the effects on growth, apoptosis, differentiation, cofactor response, and internal changes will be assayed.

Example 12

Sandwich Assay for HPC2

Monoclonal antibody is attached to a solid surface such as a plate, tube, bead, or particle. Preferably, the antibody is attached to the well surface of a 96-well ELISA plate. 100 µl sample (e.g., serum, urine, tissue cytosol) containing the HPC2 peptide/protein (wild-type or mutant) is added to the solid phase antibody. The sample is incubated for 2 hrs at room temperature. Next the sample fluid is decanted, and the solid phase is washed with buffer to remove unbound material. 100 µL of a second monoclonal antibody (to a different determinant on the HPC2 peptide/protein) is added to the solid phase. This antibody is labeled with a detector molecule (e.g., 125-I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of HPC2 peptide/protein present in the sample, is quantitated. Separate assays are performed using monoclonal antibodies which are specific for the wild-type HPC2 as well as monoclonal antibodies specific for each of the mutations identified in HPC2.

Example 13

Two-Hybrid Assay to Identify Proteins that Interact with HPC2

Sequence encoding all or portions of HPC2 are ligated to pAS2-1 (Clontech) such that the coding sequence of HPC2 is in-frame with coding sequence for the GAL4p DNA-binding domain. This plasmid construct is introduced into the yeast reporter strain Y190 by transformation. A library of activation domain fusion plasmids prepared from human prostate cDNA (Clontech) is then introduced into strain Y190 carrying the pAS2-1-based fusion construct. Transformants are spread onto 20–150 mm plates of yeast minimal media lacking leucine, tryptophan, and histidine, and containing 25 mM 3-amino-1,2,4-triazole. After one week incubation at 30° C., yeast colonies are assayed for expression of the lacZ reporter gene by β-galactosidase filter assay. Colonies that both grow in the absence of histidine and are positive for production of β-galactosidase are chosen for further characterization.

The activation domain plasmid is purified from positive colonies by the smash-and-grab technique. These plasmids are introduced into *E. coli* DH5(by electroporation and purified from *E. coli* by the alkaline lysis method. To test for the specificity of the interaction, specific activation domain plasmids are cotransformed into strain Y190 with plasmids encoding various DNA-binding domain fusion proteins, including fusions to HPC2 and human lamin C. Transformants from these experiments are assayed for expression of the HIS3 and lacZ reporter genes. Positives that express reporter genes with HPC2 constructs and not with lamin C constructs encode bona fide HPC2 interacting proteins. These proteins are identified and characterized by sequence analysis of the insert of the appropriate activation domain plasmid.

This procedure is repeated with mutant forms of the HPC2 gene, to identify proteins that interact with only the mutant protein or to determine whether a mutant form of the HPC2 protein can or cannot interact with a protein known to interact with wild-type HPC2.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Altschul S F, et al. (1990). *J. Mol. Biol.* 215: 403–410.
Altschul S F, et al. (1997). *Nucl. Acids Res.* 25:3389–3402.
Anand R (1992). *Techniques for the Analysis of Complex Genomes*, (Academic Press).
Anderson W F, et al. (1980). *Proc. Natl. Acad. Sci. USA* 77:5399–5403.
Ausubel F M, et al. (1992). *Current Protocols in Molecular Biology*, (J. Wiley and Sons, NY).
Bandyopadhyay P K and Temin H M (1984). *Mol. Cell. Biol.* 4:749–754.
Bartel P L, et al. (1993). "Using the 2-hybrid system to detect protein-protein interactions." In: *Cellular Interactions in Development: A Practical Approach*, Oxford University Press, pp. 153–179.
Beaucage S L and Caruthers M H (1981). *Tetra. Letts.* 22:1859–1862.
Berglund P, et al. (1993). *Biotechnology* 11:916–920.
Berkner K L (1992). *Curr. Top. Microbiol. Immunol.* 158:39–66.
Berkner K L, et al. (1988). *BioTechniques* 6:616–629.
Borman S (1996). *Chemical & Engineering News*, December 9 issue, pp. 42–43.
Bouchardy C, et al. (1998). *Pharmacogenetics* 8:291–298.
Breakefield X O and Geller A I (1987). *Mol. Neurobiol.* 1:337–371.
Brinster R L, et al. (1981). *Cell* 27:223–231.
Buchschacher G L and Panganiban A T (1992). *J. Virol.* 66:2731–2739.
Cannon L, et al. (1982). *Cancer Surveys* 1:47–69.
Capecchi M R (1989). *Science* 244:1288–1292.
Cariello N F (1988). *Am. J. Human Genetics* 42:726–734.
Carter B S, et al. (1992). *Proc. Natl. Acad. Sci. USA* 89:3367–3371.
Carter B S, et al. (1993). *J. Urol.* 150:797–802.
Chee M, et al. (1996). *Science* 274:610–614.
Chevray P M and Nathans D N (1992). *Proc. Natl. Acad. Sci. USA* 89:5789–5793.
Compton J (1991). *Nature* 350:91–92.
Conner B J, et al. (1983). *Proc. Natl. Acad. Sci. USA* 80:278–282.
Costantini F and Lacy E (1981). *Nature* 294:92–94.
Cotton M, et al. (1990). *Proc. Natl. Acad. Sci. USA* 87:4033–4037.
Cotton R G, et al. (1988). *Proc. Natl. Acad. Sci. USA* 85:4397–4401.
Culver K W, et al. (1992). *Science* 256:1550–1552.
Curiel D T, et al. (1991). *Proc. Natl. Acad. Sci. USA* 88:8850–8854.
Curiel D T, et al. (1992). *Hum. Gene Ther.* 3:147–154.
DeRisi J, et al. (1996). *Nature Genetics* 14:457–460.
Deutscher, M (1990). *Meth. Enzymology* 182:83–89 (Academic Press, San Diego, Calif.).
Donehower L A, et al. (1992). *Nature* 356:215–221.

Durbin R and Thierry-Mieg J (1991). A *C. elegans* Database. Documentation, code and data available from anonymous FTP servers at lirmm.lirmm.fr, cele.mrc-lmb.cam.ac.uk and ncbi.nlm.nih.gov.
Editorial (1996). *Nature Genetics* 14:367–370.
Elghanian R, et al. (1997). *Science* 277:1078–1081.
*Enhancers and Eurkarvotic Gene Expression*, Cold Spring Harbor Press, Cold Spring Harbor, N.Y. (1983).
Erickson J, et al. (1990). *Science* 249:527–533.
Fahy E, et al. (1991). *PCR Methods Appl.* 1:25–33.
Feil et al., (1996). *Proc. Natl. Acad. Sci. USA* 93:10887–10890.
Felgner P L, et al. (1987). *Proc. Natl. Acad. Sci. USA* 84:7413–7417.
Fields S and Song O-K (1989). *Nature* 340:245–246.
Fiers W, et al. (1978). *Nature* 273:113–120.
Fincham S M, et al. (1990). *The Prostate* 17:189–206.
Fink D J, et al. (1992). *Hum. Gene Ther.* 3:11–19.
Fink D J, et al. (1996). *Ann. Rev. Neurosci.* 19:265–287.
Finkelstein J, et al. (1990). *Genomics* 7:167–172.
Fodor S P A (1997). *Science* 277:393–395.
Freese A, et al. (1990). *Biochem. Pharmacol.* 40:2189–2199.
Friedman T (1991). In: *Therapy for Genetic Diseases*, T. Friedman, ed., Oxford University Press, pp. 105–121.
Gagneten et al. (1997). *Nucl. Acids Res.* 25:3326–3331.
Giovannucci E, et al. (1997). *Proc. Natl. Acad. Sci. USA* 94:3320–3323.
Glover D (1985). *DNA Cloning*, I and II (Oxford Press).
Goding (1986). *Monoclonal Antibodies: Principles and Practice,* 2d ed. (Academic Press, NY).
Godowski P J, et al. (1988). *Science* 241:812–816.
Goldgar D E, et al. (1994). *J. Natl. Can. Inst.* 86:3:200–209.
Gordon J W, et al. (1980). *Proc. Natl. Acad. Sci. USA* 77:7380–7384.
Gordon J W (1989). *Intl. Rev. Cytol.* 115:171–229.
Gorziglia M and Kapikian A Z (1992). *J. Virol.* 66:4407–4412.
Graham F L and van der Eb A J (1973). *Virology* 52:456–467.
Grompe M (1993). *Nature Genetics* 5:111–117.
Grompe M, et al. (1989). *Proc. Natl. Acad. Sci. USA* 86:5855–5892.
Gu H, et al. (1994). *Science* 265:103–106.
Guthrie G and Fink G R (1991). *Guide to Yeast Genetics and Molecular Biology* (Academic Press).
Hacia J G, et al. (1996). *Nature Genetics* 14:441–447.
Harlow E and Lane D (1988). *Antibodies: A Laboratory Manual* (Cold Spring Harbor Laboratory, Cold Spring Harbor, N.Y.).
Harty L C, et al. (1997). *J. Natl. Cancer Inst.* 89:1698–1705.
Hasty P, et al. (1991). *Nature* 350:243–246.
Helseth E, et al. (1990). *J. Virol.* 64:2416–2420.
Hodgson J (1991). *Bio/Technology* 9:19–21.
Hori H, et al. (1997). *J. Clin. Gastroenterol.* 25:568–575.
Huse W D, et al. (1989). *Science* 246:1275–1281.
Innis M A, et al. (1990). *PCR Protocols: A Guide to Methods and Applications* (Academic Press, San Diego, Calif.).
Jablonski E, et al. (1986). *Nuc. Acids Res.* 14:6115–6128.
Jakoby W B and Pastan I H (eds.) (1979). *Cell Culture. Methods in Enzymology*, Vol. 58 (Academic Press, Inc., Harcourt Brace Jovanovich (NY)).
Johnson P A, et al. (1992). *J. Virol.* 66:2952–2965.
Johnson, et al. (1993). "Peptide Turn Mimetics" In: *Biotechnology and Pharmacy*, Pezzuto et al., eds., Chapman and Hall, NY.
Kaneda Y, et al. (1989). *J. Biol. Chem.* 264:12126–12129.
Kanehisa M (1984). *Nucl. Acids Res.* 12:203–213.
Kinszler K W, et al. (1991). *Science* 251:1366–1370.
Kohler G and Milstein C (1975). *Nature* 256:495–497.
Krain L S (1974). *Preventive Medicine* 3:154–159.
Kubo T, et al. (1988). *FEBS Lett.* 241:119–125.
Kyte J and Doolittle R F (1982). *J. Mol. Biol.* 157:105–132.
Landegren U, et al. (1988). *Science* 242:229–237.
Lasko M, et al. (1992). *Proc. Natl. Acad. Sci. USA* 89:6232–6236.
Lavitrano M, et al. (1989). *Cell* 57:717–723.
Lee J E, et al. (1995). *Science* 268:836–844.
Lim C S, et al. (1991). *Circulation* 83:2007–2011.
Lin Y Z, et al. (1995). *J. Biol. Chem.* 270:14255–14258.
Lipshutz R J, et al. (1995). *BioTechniques* 19:442–447.
Lo C W (1983). *Mol. Cell. Biol.* 3:1803–1814.
Lobe and Nagy (1998). *Bioessays* 20:200–208.
Lockhart D J, et al. (1996). *Nature Biotechnology* 14:1675–1680.
Madzak C, et al. (992). *J. Gen. Virol.* 73:1533–1536.
Maniatis T, et al. (1982). *Molecular Cloning: A Laboratory Manual* (Cold Spring Harbor Laboratory, Cold Spring Harbor, N.Y.).
Mann R and Baltimore D (1985). *J. Virol.* 54:401–407.
Margolskee R F (1992). *Curr. Top. Microbiol. Immunol.* 158:67–95.
Martin R, et al. (1990). *BioTechniques* 9:762–768.
Matteucci M D and Caruthers M H (1981). *J. Am. Chem. Soc.* 103:3185.
Matthews J A and Kricka L J (1988). *Anal, Biochem.* 169:1.
Meikle A W, et al. (1985). *Prostate* 6:121–128.
Merrifield B (1963). *J. Am. Chem. Soc.* 85:2149–2156.
Metzger D, et al. (1988). *Nature* 334:31–36.
Mifflin T E (1989). *Clinical Chem.* 35:1819–1825.
Miller A D (1992). *Curr. Top. Microbiol. Immunol.* 158:1–24.
Miller A D, et al. (1985). *Mol. Cell. Biol.* 5:431–437.
Miller A D, et al. (1988). *J. Virol.* 62:4337–4345.
Modrich P (1991). *Ann. Rev. Genet.* 25:229–253.
Mombaerts P, et al. (1992). *Cell* 68:869–877.
Morganti G, et al. (1956). *Acta Geneticae Medicae et Gemellogogiae* 6:304–305.
Moss B (1992). *Curr. Top. Microbiol. Immunol.* 158:25–38.
Moss B (1996). *Proc. Natl. Acad. Sci. USA* 93:11341–11348.
Muzyczka N (1992). *Curr. Top. Microbiol. Immunol.* 158:97–129.
Nabel (1992). *Hum. Gene Ther.* 3:399–410.
Nabel E G, et al. (1990). *Science* 249:1285–1288.
Naldini L, et al. (1996). *Science* 272:263–267.
Newton C R, et al. (1989). *Nucl. Acids Res.* 17:2503–2516.
Nguyen Q, et al. (1992). *BioTechniques* 13:116–123.
Novack D F, et al. (1986). *Proc. Natl. Acad. Sci. USA* 83:586–590.
Ohi S, et al. (1990). *Gene* 89:279–282.
Orita M, et al. (1989) *Proc. Natl. Acad. Sci. USA* 86:2776–2770.
Osterrieder and Wolf (1998). *Rev. Sci. Tech.* 17:351–364.
Page K A, et al. (1990). *J. Virol.* 64:5270–5276.
Pellicer A, et al. (1980). *Science* 209:1414–1422.
Petropoulos C J, et al. (1992). *J. Virol.* 66:3391–3397.
Philpott K L, et al. (1992). *Science* 256:1448–1452.
Quantin B, et al. (1992). *Proc. Natl. Acad. Sci. USA* 89:2581–2584.
*Remington's Pharmaceutical Sciences,* 18th Ed. (1990, Mack Publishing Co., Easton, Pa.).
Rigby P W J, et at (1977). *J. Mol. Biol.* 113:237–251.
Rojas M, et al. (1996). *J. Biol. Chem.* 271:27456–27461.
Rosenfeld M A, et al. (1992). *Cell* 68:143–155.

Ruano G and Kidd KK (1989). *Nucl. Acids Res.* 17:8392.
Russell D and Hirata R (1998). *Nature Genetics* 18:323–328.
Sambrook J, et at (1989). *Molecular Cloning: A Laboratogy Manual*, 2nd Ed. (Cold Spring Harbor Laboratory, Cold Spring Harbor, N.Y.).
Scharf S J (1986). *Science* 233:1076–1078.
Schneider G, et al. (1998). *Nature Genetics* 18:180–183.
Scopes R (1982). *Protein Purification: Principles and Practice*, (Springer-Verlag, NY).
Shastry et al. (1995). *Experientia* 51:1028–1039.
Shastry et al. (1998). *Mol. Cell. Biochem.* 181:163–179.
Sheffield V C, et al. (1989). *Proc. Natl. Acad. Sci. USA* 86:232–236.
Sheffield V C, et al. (1991). *Am. J. Hum. Genet.* 49:699–706.
Shenk T E, et at (1975). *Proc. Natl. Acad. Sci. USA* 72:989–993.
Shields P B (1997). *Proc. Dept. Defense BCRP Era of Hope meeting*, Vol. 1 ("Frontiers in Prevention and Detection"), pp.9–10.
Shimada T, et al. (1991). *J. Clin. Invest.* 88:1043–1047.
Shinkai Y, et al. (1992). *Cell* 68:855–867.
Shoemaker D D, et al. (1996). *Nature Genetics* 14:450–456.
Smith J R, et al. (1996). *Science* 274:1371–1374.
Smith S W, et a. (1994). *CABIOS* 10:671–675.
Snouwaert J N, et al. (1992). *Science* 257:1083–1088.
Sorge J, et al. (1984). *Mol. Cell. Biol.* 4:1730–1737.
Spargo C A, et al. (1996). *Mol. Cell. Probes* 10:247–256.
Steinberg G D, et a. (1990). *Prostate* 17:337–347.
Stewart M J, et at (1992). *Hum. Gene Ther.* 3:267–275.
Stratford-Perricaudet L D, et al. (1990). *Hum. Gene Ther.* 1:241–256.
Thierry-Mieg D, et al. (1995). Ace.mbly. A graphic interactive program to support shotgun and directed sequencing projects.
Thompson S, et al. (1989). *Cell* 56:313–321.
Valancius V and Smithies O (1991). *Mol. Cell Biol.* 11:1402–1408.
Van der Putten H, et al. (1985). *Proc. Natl. Acad. Sci. USA* 82:6148–6152.
Wagner E, et al. (1990). *Proc. Natl. Acad. Sci. USA* 87:3410–3414.
Wagner E, et al. (1991). *Proc. Natl. Acad. Sci. USA* 88:4255–4259.
Walker G T, et al. (1992). *Nucl. Acids Res.* 20:1691–1696.
Wang C Y and Huang L (1989). *Biochemistry* 28:9508–9514.
Wartell R M, et al. (1990). *Nucl. Acids Res.* 18:2699–2705.
Wells J A (1991). *Methods in Enzymol.* 202:390–411.
Wetmur J G and Davidson N (1968). *J. Mol. Biol.* 31:349–370.
White M B, et al. (1992). *Genomics* 12:301–306.
White R and Lalouel J M (1988). *Annu. Rev. Genet.* 22:259–279.
Wilkinson G W and Akrigg A (1992). *Nucleic Acids Res.* 20:2233–2239.
Wolff J A, et al. (1990). *Science* 247:1465–1468.
Wolff J A, et al. (1991). *BioTechniques* 11:474–485.
Woolf C M (1960). *Cancer* 13:739–744.,
Wu D Y and Wallace R B (1989). *Genomics* 4:560–569.
Wu C H, et al. (1989). *J. Biol. Chem.* 264:16985–16987.
Wu G Y, et al. (1991). *J. Biol. Chem.* 266:14338–14342.
Xu J, et al. (1998). *Nat. Genet.* 20:175–179.
Zenke M, et al. (1990). *Proc. Natl. Acad. Sci. USA* 87:3655–3659.
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,376,110
U.S. Pat. No. 4,486,530
U.S. Pat. No. 4,554,101
U.S. Pat. No. 4,683,195
U.S. Pat. No. 4,683,202
U.S. Pat. No. 4,816,567
U.S. Pat. No. 4,868,105
U.S. Pat. No. 4,873,191
U.S. Pat. No. 5,252,479
U.S. Pat. No. 5,270,184
U.S. Pat. No. 5,409,818
U.S. Pat. No. 5,436,146
U.S. Pat. No. 5,455,166
U.S. Pat. No. 5,550,050
U.S. Pat. No. 5,691,198
U.S. Pat. No. 5,735,500
U.S. Pat. No. 5,747,469
Hitzeman et al., EP 73,675A
EPO Publication No. 225,807
EP 425,731A
European Patent Application Publication No. 0332435
WO 84/03564
WO 90/07936
WO 92/19195
WO 93/07282
WO 94/25503
WO 95/01203
WO 95/05452
WO 96/02286
WO 96/02646
WO 96/11698
WO 96/40871
WO 96/40959
WO 97/12635

What is claimed is:

1. An isolated nucleic acid coding for a polypeptide comprising the amino acid sequence set forth in SEQ ID NO:2 or the complement of said nucleic acid.

2. A vector which comprises an isolated nucleic acid as claimed in claim 1.

3. Isolated host cells transformed with a vector as claimed in claim 2.

4. A cell culture comprising the isolated host cells of claim 3.

5. An expression vector which comprises an isolated nucleic acid of claim 1 wherein said nucleic acid is operably linked to regulatory sequences which control expression of said nucleic acid in host cells for said vector.

6. The isolated nucleic acid of claim 1 wherein said nucleic acid comprises the nucleotide sequence (a) set forth in SEQ ID NO:1, or (b) the complement of said nucleic acid.

7. The isolated nucleic acid of claim 1 wherein said nucleic acid comprises the nucleotide sequence set forth in (a) SEQ ID NO:3, (b) SEQ ID NO:28, or (c) the complements of said nucleic acids.

8. A method of producing a polypeptide of SEQ ID NO:2 which comprises (i) culturing host cells containing an expression vector encoding said polypeptide under conditions suitable for the production of said polypeptide and (ii) recovering said polypeptide.

9. A method as claimed in claim 8 which further comprises labeling the polypeptide which is recovered.

10. An isolated nucleic acid comprising SEQ ID NO:1 wherein a G is inserted between bases 1641 and 1642 or the complement of said nucleic acid.

11. A vector which comprises an isolated nucleic acid as claimed in claim 10.

12. Isolated host cells transformed with a vector as claimed in claim 11.

13. A cell culture comprising the isolated host cells of claim 12.

14. An expression vector which comprises an isolated nucleic acid of claim 10 and said nucleic acid is operably linked to regulatory sequences which control expression of said nucleic acid in host cells for said vector.

15. An isolated nucleic acid comprising SEQ ID NO:3 wherein a G inserted between bases 1691 and 1692 or the complement of said nucleic acid.

16. A vector which comprises an isolated nucleic acid as claimed in claim 15.

17. Isolated host cells transformed with a vector as claimed in claim 16.

18. A cell culture comprising the isolated host cells of claim 17.

19. An expression vector which comprises an isolated nucleic acid of claim 15 and said nucleic acid is operably linked to regulatory sequences which control expression of said nucleic acid in host cells for said vector.

20. An isolated nucleic acid comprising SEQ ID NO:28 wherein a G is inserted between bases 22292 and 22293 or the complement of said nucleic acid.

21. A vector which comprises an isolated nucleic acid as claimed in claim 20.

22. Isolated host cells transformed with a vector as claimed in claim 21.

23. A cell culture comprising the isolated host cells of claim 22.

24. An expression vector which comprises an isolated nucleic acid of claim 20 and said nucleic acid is operably linked to regulatory sequences which control expression of said nucleic acid in host cells for said vector.

25. A method of producing a polypeptide encoded by a nucleic acid comprising SEQ ID NO: 1, wherein G is inserted between bases 1641 and 1642, comprising (i) culturing host cells containing an expression vector encoding said polypeptide under conditions suitable for production of said polypeptide and (ii) recovering said polypeptide.

26. A method as claimed in claim 25 which further comprises labeling the polypeptide which is recovered.

\* \* \* \* \*

SEQUENCE LISTING

<160> NUMBER OF SEQ ID NOS: 213

<210> SEQ ID NO 1
<211> LENGTH: 2481
<212> TYPE: DNA
<213> ORGANISM: Homo sapiens
<220> FEATURE:

<221> NAME/KEY: CDS
<222> LOCATION: (1)..(2478)

<400> SEQUENCE: 1

| | | | | | | | | | | | | | | | | |
|---|---|---|---|---|---|---|---|---|---|---|---|---|---|---|---|---|
| atg | tgg | gcg | ctt | tgc | tcg | ctg | ctg | cgg | tcc | gcg | gcc | gga | cgc | acc | atg | 48 |
| Met | Trp | Ala | Leu | Cys | Ser | Leu | Leu | Arg | Ser | Ala | Ala | Gly | Arg | Thr | Met | |
| 1 | | | | 5 | | | | | 10 | | | | | 15 | | |

| tcg | cag | gga | cgc | acc | ata | tcg | cag | gca | ccc | gcc | cgc | cgc | gag | cgg | ccg | 96 |
|---|---|---|---|---|---|---|---|---|---|---|---|---|---|---|---|---|
| Ser | Gln | Gly | Arg | Thr | Ile | Ser | Gln | Ala | Pro | Ala | Arg | Arg | Glu | Arg | Pro | |
| | | | 20 | | | | | 25 | | | | | 30 | | | |

| cgc | aag | gac | ccg | ctg | cgg | cac | ctg | cgc | acg | cga | gag | aag | cgc | gga | ccg | 144 |
|---|---|---|---|---|---|---|---|---|---|---|---|---|---|---|---|---|
| Arg | Lys | Asp | Pro | Leu | Arg | His | Leu | Arg | Thr | Arg | Glu | Lys | Arg | Gly | Pro | |
| | | 35 | | | | | 40 | | | | | 45 | | | | |

| tcg | ggg | tgc | tcc | ggc | ggc | cca | aac | acc | gtg | tac | ctg | cag | gtg | gtg | gca | 192 |
|---|---|---|---|---|---|---|---|---|---|---|---|---|---|---|---|---|
| Ser | Gly | Cys | Ser | Gly | Gly | Pro | Asn | Thr | Val | Tyr | Leu | Gln | Val | Val | Ala | |
| 50 | | | | | 55 | | | | | 60 | | | | | | |

| gcg | ggt | agc | cgg | gac | tcg | ggc | gcc | gcg | ctc | tac | gtc | ttc | tcc | gag | ttc | 240 |
|---|---|---|---|---|---|---|---|---|---|---|---|---|---|---|---|---|
| Ala | Gly | Ser | Arg | Asp | Ser | Gly | Ala | Ala | Leu | Tyr | Val | Phe | Ser | Glu | Phe | |
| 65 | | | | 70 | | | | | 75 | | | | | 80 | | |

| aac | cgg | tat | ctc | ttc | aac | tgt | gga | gaa | ggc | gtt | cag | aga | ctc | atg | cag | 288 |
|---|---|---|---|---|---|---|---|---|---|---|---|---|---|---|---|---|
| Asn | Arg | Tyr | Leu | Phe | Asn | Cys | Gly | Glu | Gly | Val | Gln | Arg | Leu | Met | Gln | |
| | | | | 85 | | | | | 90 | | | | | 95 | | |

| gag | cac | aag | tta | aag | gtt | gct | cgc | ctg | gac | aac | ata | ttc | ctg | aca | cga | 336 |
|---|---|---|---|---|---|---|---|---|---|---|---|---|---|---|---|---|
| Glu | His | Lys | Leu | Lys | Val | Ala | Arg | Leu | Asp | Asn | Ile | Phe | Leu | Thr | Arg | |
| | | | 100 | | | | | 105 | | | | | 110 | | | |

| atg | cac | tgg | tct | aat | gtt | ggg | ggc | tta | agt | gga | atg | att | ctt | act | tta | 384 |
|---|---|---|---|---|---|---|---|---|---|---|---|---|---|---|---|---|
| Met | His | Trp | Ser | Asn | Val | Gly | Gly | Leu | Ser | Gly | Met | Ile | Leu | Thr | Leu | |
| | | 115 | | | | | 120 | | | | | 125 | | | | |

| aag | gaa | acc | ggg | ctt | cca | aag | tgt | gta | ctt | tct | gga | cct | cca | caa | ctg | 432 |
|---|---|---|---|---|---|---|---|---|---|---|---|---|---|---|---|---|
| Lys | Glu | Thr | Gly | Leu | Pro | Lys | Cys | Val | Leu | Ser | Gly | Pro | Pro | Gln | Leu | |
| | 130 | | | | | 135 | | | | | 140 | | | | | |

| gaa | aaa | tac | ctc | gaa | gca | atc | aaa | ata | ttt | tct | ggt | cca | ttg | aaa | gga | 480 |
|---|---|---|---|---|---|---|---|---|---|---|---|---|---|---|---|---|
| Glu | Lys | Tyr | Leu | Glu | Ala | Ile | Lys | Ile | Phe | Ser | Gly | Pro | Leu | Lys | Gly | |
| 145 | | | | | 150 | | | | | 155 | | | | | 160 | |

| ata | gaa | ctg | gct | gtg | cgg | ccc | cac | tct | gcc | cca | gaa | tac | gag | gat | gaa | 528 |
|---|---|---|---|---|---|---|---|---|---|---|---|---|---|---|---|---|
| Ile | Glu | Leu | Ala | Val | Arg | Pro | His | Ser | Ala | Pro | Glu | Tyr | Glu | Asp | Glu | |
| | | | | 165 | | | | | 170 | | | | | 175 | | |

| acc | atg | aca | gtt | tac | cag | atc | ccc | ata | cac | agt | gaa | cag | agg | agg | gga | 576 |
|---|---|---|---|---|---|---|---|---|---|---|---|---|---|---|---|---|
| Thr | Met | Thr | Val | Tyr | Gln | Ile | Pro | Ile | His | Ser | Glu | Gln | Arg | Arg | Gly | |
| | | | 180 | | | | | 185 | | | | | 190 | | | |

| aag | cac | caa | cca | tgg | cag | agt | cca | gaa | agg | cct | ctc | agc | agg | ctc | agt | 624 |
|---|---|---|---|---|---|---|---|---|---|---|---|---|---|---|---|---|
| Lys | His | Gln | Pro | Trp | Gln | Ser | Pro | Glu | Arg | Pro | Leu | Ser | Arg | Leu | Ser | |
| | | 195 | | | | | 200 | | | | | 205 | | | | |

| cca | gag | cga | tct | tca | gac | tcc | gag | tcg | aat | gaa | aat | gag | cca | cac | ctt | 672 |
|---|---|---|---|---|---|---|---|---|---|---|---|---|---|---|---|---|
| Pro | Glu | Arg | Ser | Ser | Asp | Ser | Glu | Ser | Asn | Glu | Asn | Glu | Pro | His | Leu | |
| | 210 | | | | | 215 | | | | | 220 | | | | | |

| cca | cat | ggt | gtt | agc | cag | aga | aga | ggg | gtc | agg | gac | tct | tcc | ctg | gtc | 720 |
|---|---|---|---|---|---|---|---|---|---|---|---|---|---|---|---|---|
| Pro | His | Gly | Val | Ser | Gln | Arg | Arg | Gly | Val | Arg | Asp | Ser | Ser | Leu | Val | |
| 225 | | | | | 230 | | | | | 235 | | | | | 240 | |

| gta | gct | ttc | atc | tgt | aag | ctt | cac | tta | aag | aga | gga | aac | ttc | ttg | gtg | 768 |
|---|---|---|---|---|---|---|---|---|---|---|---|---|---|---|---|---|
| Val | Ala | Phe | Ile | Cys | Lys | Leu | His | Leu | Lys | Arg | Gly | Asn | Phe | Leu | Val | |
| | | | | 245 | | | | | 250 | | | | | 255 | | |

| ctc | aaa | gca | aag | gag | atg | ggc | ctc | cca | gtt | ggg | aca | gct | gcc | atc | gct | 816 |
|---|---|---|---|---|---|---|---|---|---|---|---|---|---|---|---|---|
| Leu | Lys | Ala | Lys | Glu | Met | Gly | Leu | Pro | Val | Gly | Thr | Ala | Ala | Ile | Ala | |
| | | | 260 | | | | | 265 | | | | | 270 | | | |

| ccc | atc | att | gct | gct | gtc | aag | gac | ggg | aaa | agc | atc | act | cat | gaa | gga | 864 |
|---|---|---|---|---|---|---|---|---|---|---|---|---|---|---|---|---|
| Pro | Ile | Ile | Ala | Ala | Val | Lys | Asp | Gly | Lys | Ser | Ile | Thr | His | Glu | Gly | |
| | | 275 | | | | | 280 | | | | | 285 | | | | |

| aga | gag | att | ttg | gct | gaa | gag | ctg | tgt | act | cct | cca | gat | cct | ggt | gct | 912 |
|---|---|---|---|---|---|---|---|---|---|---|---|---|---|---|---|---|
| Arg | Glu | Ile | Leu | Ala | Glu | Glu | Leu | Cys | Thr | Pro | Pro | Asp | Pro | Gly | Ala | |

-continued

```
         290                 295                 300
gct ttt gtg gtg gta gaa tgt cca gat gaa agc ttc att caa ccc atc    960
Ala Phe Val Val Val Glu Cys Pro Asp Glu Ser Phe Ile Gln Pro Ile
305                 310                 315                 320 tgt gag aat gcc acc ttt cag agg tac caa gga aag gca gat gcc ccc   1008
Cys Glu Asn Ala Thr Phe Gln Arg Tyr Gln Gly Lys Ala Asp Ala Pro
                325                 330                 335 gtg gcc ttg gtg gtt cac atg gcc cca gca tct gtg ctt gtg gac agc   1056
Val Ala Leu Val Val His Met Ala Pro Ala Ser Val Leu Val Asp Ser
            340                 345                 350 agg tac cag cag tgg atg gag agg ttt ggg cct gac acc cag cac ttg   1104
Arg Tyr Gln Gln Trp Met Glu Arg Phe Gly Pro Asp Thr Gln His Leu
        355                 360                 365 gtc ctg aat gag aac tgt gcc tca gtt cac aac ctt cgc agc cac aag   1152
Val Leu Asn Glu Asn Cys Ala Ser Val His Asn Leu Arg Ser His Lys
    370                 375                 380 att caa acc cag ctc aac ctc atc cac ccg gac atc ttc ccc ctg ctc   1200
Ile Gln Thr Gln Leu Asn Leu Ile His Pro Asp Ile Phe Pro Leu Leu
385                 390                 395                 400 acc agt ttc cgc tgt aag aag gag ggc ccc acc ctc agt gtg ccc atg   1248
Thr Ser Phe Arg Cys Lys Lys Glu Gly Pro Thr Leu Ser Val Pro Met
                405                 410                 415 gtt cag ggt gaa tgc ctc ctc aag tac cag ctc cgt ccc agg agg gag   1296
Val Gln Gly Glu Cys Leu Leu Lys Tyr Gln Leu Arg Pro Arg Arg Glu
            420                 425                 430 tgg cag agg gat gcc att att act tgc aat cct gag gaa ttc ata gtt   1344
Trp Gln Arg Asp Ala Ile Ile Thr Cys Asn Pro Glu Glu Phe Ile Val
        435                 440                 445 gag gcg ctg cag ctt ccc aac ttc cag cag agc gtg cag gag tac agg   1392
Glu Ala Leu Gln Leu Pro Asn Phe Gln Gln Ser Val Gln Glu Tyr Arg
    450                 455                 460 agt gcg cag gac ggc cca gcc cca gca gag aaa aga agt cag tac        1440
Arg Ser Ala Gln Asp Gly Pro Ala Pro Ala Glu Lys Arg Ser Gln Tyr
465                 470                 475                 480 cca gaa atc atc ttc ctt gga aca ggg tct gcc atc ccg atg aag att   1488
Pro Glu Ile Ile Phe Leu Gly Thr Gly Ser Ala Ile Pro Met Lys Ile
                485                 490                 495 cga aat gtc agt gcc aca ctt gtc aac ata agc ccc gac acg tct ctg   1536
Arg Asn Val Ser Ala Thr Leu Val Asn Ile Ser Pro Asp Thr Ser Leu
            500                 505                 510 cta ctg gac tgt ggt gag ggc aca ttt ggg cag ctg tgc cgt cat tac   1584
Leu Leu Asp Cys Gly Glu Gly Thr Phe Gly Gln Leu Cys Arg His Tyr
        515                 520                 525 gga gac cag gtg gac agg gtc ctg ggc acc ctg gct gct gtg ttt gtg   1632
Gly Asp Gln Val Asp Arg Val Leu Gly Thr Leu Ala Ala Val Phe Val
    530                 535                 540 tcc cac ctg cac gca gat cac cac acg ggc ttg cca agt atc ttg ctg   1680
Ser His Leu His Ala Asp His His Thr Gly Leu Pro Ser Ile Leu Leu
545                 550                 555                 560 cag aga gaa cgc gcc ttg gca tct ttg gga aag ccg ctt cac cct ttg   1728
Gln Arg Glu Arg Ala Leu Ala Ser Leu Gly Lys Pro Leu His Pro Leu
                565                 570                 575 ctg gtg gtt gcc ccc aac cag ctc aaa gcc tgg ctc cag cag tac cac   1776
Leu Val Val Ala Pro Asn Gln Leu Lys Ala Trp Leu Gln Gln Tyr His
            580                 585                 590 aac cag tgc cag gag gtc ctg cac cac atc agt atg att cct gcc aaa   1824
Asn Gln Cys Gln Glu Val Leu His His Ile Ser Met Ile Pro Ala Lys
        595                 600                 605 tgc ctt cag gaa ggg gct gag atc tcc agt cct gca gtg gaa aga ttg   1872
```

-continued

```
Cys Leu Gln Glu Gly Ala Glu Ile Ser Ser Pro Ala Val Glu Arg Leu
        610                 615                 620 atc agt tcg ctg ttg cga aca tgt gat ttg gaa gag ttt cag acc tgt      1920
Ile Ser Ser Leu Leu Arg Thr Cys Asp Leu Glu Glu Phe Gln Thr Cys
625                 630                 635                 640 ctg gtg cgg cac tgc aag cat gcg ttt ggc tgt gcg ctg gtg cac acc      1968
Leu Val Arg His Cys Lys His Ala Phe Gly Cys Ala Leu Val His Thr
                645                 650                 655 tct ggc tgg aaa gtg gtc tat tcc ggg gac acc atg ccc tgc gag gct      2016
Ser Gly Trp Lys Val Val Tyr Ser Gly Asp Thr Met Pro Cys Glu Ala
            660                 665                 670 ctg gtc cgg atg ggg aaa gat gcc acc ctc ctg ata cat gaa gcc acc      2064
Leu Val Arg Met Gly Lys Asp Ala Thr Leu Leu Ile His Glu Ala Thr
        675                 680                 685 ctg gaa gat ggt ttg gaa gag gaa gca gtg gaa aag aca cac agc aca      2112
Leu Glu Asp Gly Leu Glu Glu Glu Ala Val Glu Lys Thr His Ser Thr
    690                 695                 700 acg tcc caa gcc atc agc gtg ggg atg cgg atg aac gcg gag ttc att      2160
Thr Ser Gln Ala Ile Ser Val Gly Met Arg Met Asn Ala Glu Phe Ile
705                 710                 715                 720 atg ctg aac cac ttc agc cag cgc tat gcc aag gtc ccc ctc ttc agc      2208
Met Leu Asn His Phe Ser Gln Arg Tyr Ala Lys Val Pro Leu Phe Ser
                725                 730                 735 ccc aac ttc agc gag aaa gtg gga gtt gcc ttt gac cac atg aag gtc      2256
Pro Asn Phe Ser Glu Lys Val Gly Val Ala Phe Asp His Met Lys Val
            740                 745                 750 tgc ttt gga gac ttt cca aca atg ccc aag ctg att ccc cca ctg aaa      2304
Cys Phe Gly Asp Phe Pro Thr Met Pro Lys Leu Ile Pro Pro Leu Lys
        755                 760                 765 gcc ctg ttt gct ggc gac atc gag gag atg gag gag cgc agg gag aag      2352
Ala Leu Phe Ala Gly Asp Ile Glu Glu Met Glu Glu Arg Arg Glu Lys
    770                 775                 780 cgg gag ctg cgg cag gtg cgg gcg gcc ctc ctg tcc agg gag ctg gca      2400
Arg Glu Leu Arg Gln Val Arg Ala Ala Leu Leu Ser Arg Glu Leu Ala
785                 790                 795                 800 ggc ggc ctg gag gat ggg gag cct cag cag aag cgg gcc cac aca gag      2448
Gly Gly Leu Glu Asp Gly Glu Pro Gln Gln Lys Arg Ala His Thr Glu
                805                 810                 815 gag cca cag gcc aag aag gtc aga gcc cag tga                          2481
Glu Pro Gln Ala Lys Lys Val Arg Ala Gln
            820                 825

<210> SEQ ID NO 2
<211> LENGTH: 826
<212> TYPE: PRT
<213> ORGANISM: Homo sapiens

<400> SEQUENCE: 2

Met Trp Ala Leu Cys Ser Leu Leu Arg Ser Ala Ala Gly Arg Thr Met
 1               5                  10                  15

Ser Gln Gly Arg Thr Ile Ser Gln Ala Pro Ala Arg Arg Glu Arg Pro
                20                  25                  30

Arg Lys Asp Pro Leu Arg His Leu Arg Thr Arg Glu Lys Arg Gly Pro
            35                  40                  45

Ser Gly Cys Ser Gly Gly Pro Asn Thr Val Tyr Leu Gln Val Val Ala
        50                  55                  60

Ala Gly Ser Arg Asp Ser Gly Ala Ala Leu Tyr Val Phe Ser Glu Phe
65                  70                  75                  80

Asn Arg Tyr Leu Phe Asn Cys Gly Glu Gly Val Gln Arg Leu Met Gln
```

-continued

```
                85                  90                  95
Glu His Lys Leu Lys Val Ala Arg Leu Asp Asn Ile Phe Leu Thr Arg
                100                 105                 110

Met His Trp Ser Asn Val Gly Gly Leu Ser Gly Met Ile Leu Thr Leu
            115                 120                 125

Lys Glu Thr Gly Leu Pro Lys Cys Val Leu Ser Gly Pro Pro Gln Leu
        130                 135                 140

Glu Lys Tyr Leu Glu Ala Ile Lys Ile Phe Ser Gly Pro Leu Lys Gly
145                 150                 155                 160

Ile Glu Leu Ala Val Arg Pro His Ser Ala Pro Glu Tyr Glu Asp Glu
                165                 170                 175

Thr Met Thr Val Tyr Gln Ile Pro Ile His Ser Glu Gln Arg Arg Gly
                180                 185                 190

Lys His Gln Pro Trp Gln Ser Pro Glu Arg Pro Leu Ser Arg Leu Ser
            195                 200                 205

Pro Glu Arg Ser Ser Asp Ser Glu Ser Asn Glu Asn Glu Pro His Leu
        210                 215                 220

Pro His Gly Val Ser Gln Arg Gly Val Arg Asp Ser Ser Leu Val
225                 230                 235                 240

Val Ala Phe Ile Cys Lys Leu His Leu Lys Arg Gly Asn Phe Leu Val
                245                 250                 255

Leu Lys Ala Lys Glu Met Gly Leu Pro Val Gly Thr Ala Ala Ile Ala
                260                 265                 270

Pro Ile Ile Ala Ala Val Lys Asp Gly Lys Ser Ile Thr His Glu Gly
            275                 280                 285

Arg Glu Ile Leu Ala Glu Leu Cys Thr Pro Pro Asp Pro Gly Ala
        290                 295                 300

Ala Phe Val Val Val Glu Cys Pro Asp Glu Ser Phe Ile Gln Pro Ile
305                 310                 315                 320

Cys Glu Asn Ala Thr Phe Gln Arg Tyr Gln Gly Lys Ala Asp Ala Pro
                325                 330                 335

Val Ala Leu Val Val His Met Ala Pro Ala Ser Val Leu Val Asp Ser
                340                 345                 350

Arg Tyr Gln Gln Trp Met Glu Arg Phe Gly Pro Asp Thr Gln His Leu
            355                 360                 365

Val Leu Asn Glu Asn Cys Ala Ser Val His Asn Leu Arg Ser His Lys
        370                 375                 380

Ile Gln Thr Gln Leu Asn Leu Ile His Pro Asp Ile Phe Pro Leu Leu
385                 390                 395                 400

Thr Ser Phe Arg Cys Lys Lys Glu Gly Pro Thr Leu Ser Val Pro Met
                405                 410                 415

Val Gln Gly Glu Cys Leu Leu Lys Tyr Gln Leu Arg Pro Arg Arg Glu
                420                 425                 430

Trp Gln Arg Asp Ala Ile Ile Thr Cys Asn Pro Glu Glu Phe Ile Val
            435                 440                 445

Glu Ala Leu Gln Leu Pro Asn Phe Gln Gln Ser Val Gln Glu Tyr Arg
        450                 455                 460

Arg Ser Ala Gln Asp Gly Pro Ala Pro Ala Glu Lys Arg Ser Gln Tyr
465                 470                 475                 480

Pro Glu Ile Ile Phe Leu Gly Thr Gly Ser Ala Ile Pro Met Lys Ile
                485                 490                 495

Arg Asn Val Ser Ala Thr Leu Val Asn Ile Ser Pro Asp Thr Ser Leu
                500                 505                 510
```

-continued

```
Leu Leu Asp Cys Gly Glu Gly Thr Phe Gly Gln Leu Cys Arg His Tyr
            515                 520                 525
Gly Asp Gln Val Asp Arg Val Leu Gly Thr Leu Ala Ala Val Phe Val
        530                 535                 540
Ser His Leu His Ala Asp His His Thr Gly Leu Pro Ser Ile Leu Leu
545                 550                 555                 560
Gln Arg Glu Arg Ala Leu Ala Ser Leu Gly Lys Pro Leu His Pro Leu
                565                 570                 575
Leu Val Val Ala Pro Asn Gln Leu Lys Ala Trp Leu Gln Gln Tyr His
            580                 585                 590
Asn Gln Cys Gln Glu Val Leu His His Ile Ser Met Ile Pro Ala Lys
        595                 600                 605
Cys Leu Gln Glu Gly Ala Glu Ile Ser Ser Pro Ala Val Glu Arg Leu
    610                 615                 620
Ile Ser Ser Leu Leu Arg Thr Cys Asp Leu Glu Glu Phe Gln Thr Cys
625                 630                 635                 640
Leu Val Arg His Cys Lys His Ala Phe Gly Cys Ala Leu Val His Thr
                645                 650                 655
Ser Gly Trp Lys Val Val Tyr Ser Gly Asp Thr Met Pro Cys Glu Ala
            660                 665                 670
Leu Val Arg Met Gly Lys Asp Ala Thr Leu Leu Ile His Glu Ala Thr
        675                 680                 685
Leu Glu Asp Gly Leu Glu Glu Glu Ala Val Glu Lys Thr His Ser Thr
    690                 695                 700
Thr Ser Gln Ala Ile Ser Val Gly Met Arg Met Asn Ala Glu Phe Ile
705                 710                 715                 720
Met Leu Asn His Phe Ser Gln Arg Tyr Ala Lys Val Pro Leu Phe Ser
                725                 730                 735
Pro Asn Phe Ser Glu Lys Val Gly Val Ala Phe Asp His Met Lys Val
            740                 745                 750
Cys Phe Gly Asp Phe Pro Thr Met Pro Lys Leu Ile Pro Pro Leu Lys
        755                 760                 765
Ala Leu Phe Ala Gly Asp Ile Glu Glu Met Glu Glu Arg Arg Glu Lys
    770                 775                 780
Arg Glu Leu Arg Gln Val Arg Ala Ala Leu Leu Ser Arg Glu Leu Ala
785                 790                 795                 800
Gly Gly Leu Glu Asp Gly Glu Pro Gln Gln Lys Arg Ala His Thr Glu
                805                 810                 815
Glu Pro Gln Ala Lys Lys Val Arg Ala Gln
            820                 825
```

<210> SEQ ID NO 3
<211> LENGTH: 2958
<212> TYPE: DNA
<213> ORGANISM: Homo sapiens
<220> FEATURE:
<221> NAME/KEY: misc_feature
<222> LOCATION: (51)..(2531)
<223> OTHER INFORMATION: coding sequence as in SEQ ID NO:1

<400> SEQUENCE: 3

```
cgcgggcgta ggtgaccggc ggctttctca gttttggtgg agacgggcgc atgtgggcgc      60
tttgctcgct gctgcggtcc gcggccggac gcaccatgtc gcaggacgcg accatatcgc     120
aggcacccgc ccgccgcgag cggccgcgca aggacccgct gcggcacctg cgcacgcgag     180
```

-continued

| | |
|---|---|
| agaagcgcgg accgtcgggg tgctccggcg gcccaaacac cgtgtacctg caggtggtgg | 240 |
| cagcgggtag ccgggactcg ggcgccgcgc tctacgtctt ctccgagttc aaccggtatc | 300 |
| tcttcaactg tggagaaggc gttcagagac tcatgcagga gcacaagtta aaggttgctc | 360 |
| gcctggacaa catattcctg acacgaatgc actggtctaa tgttgggggc ttaagtggaa | 420 |
| tgattcttac tttaaaggaa accgggcttc caaagtgtgt actttctgga cctccacaac | 480 |
| tggaaaaata cctcgaagca atcaaaatat tttctggtcc attgaaagga atagaactgg | 540 |
| ctgtgcggcc ccactctgcc ccagaatacg aggatgaaac catgacagtt taccagatcc | 600 |
| ccatacacag tgaacagagg aggggaaagc accaaccatg gcagagtcca gaaaggcctc | 660 |
| tcagcaggct cagtccagag cgatcttcag actccgagtc gaatgaaaat gagccacacc | 720 |
| ttccacatgt tgttagccag agaagagggg tcagggactc ttccctggtc gtagctttca | 780 |
| tctgtaagct tcacttaaag agaggaaact tcttggtgct caaagcaaag gagatgggcc | 840 |
| tcccagttgg gacagctgcc atcgctccca tcattgctgc tgtcaaggac gggaaaagca | 900 |
| tcactcatga aggaagagag attttggctg aagagctgtg tactcctcca gatcctggtg | 960 |
| ctgcttttgt ggtggtagaa tgtccagatg aaagcttcat caacccatc tgtgagaatg | 1020 |
| ccaccttca gaggtaccaa ggaaaggcag atgcccccgt ggccttggtg gttcacatgg | 1080 |
| ccccagcatc tgtgcttgtg gacagcaggt accagcagtg gatggagagg tttgggcctg | 1140 |
| acacccagca cttggtcctg aatgagaact gtgcctcagt tcacaacctt cgcagccaca | 1200 |
| agattcaaac ccagctcaac ctcatccacc cggacatctt cccctgctc accagtttcc | 1260 |
| gctgtaagaa ggagggcccc accctcagtg tgcccatggt tcagggtgaa tgcctcctca | 1320 |
| agtaccagct ccgtcccagg agggagtggc agagggatgc cattattact tgcaatcctg | 1380 |
| aggaattcat agttgaggcg ctgcagcttc ccaacttcca gcagagcgtg caggagtaca | 1440 |
| ggaggagtgc gcaggacggc ccagcccag cagagaaaag aagtcagtac cagaaatca | 1500 |
| tcttccttgg aacagggtct gccatcccga tgaagattcg aaatgtcagt gccacacttg | 1560 |
| tcaacataag ccccgacacg tctctgctac tggactgtgg tgagggcaca tttgggcagc | 1620 |
| tgtgccgtca ttacggagac caggtggaca gggtcctggg caccctggct gctgtgtttg | 1680 |
| tgtcccacct gcacgcagat caccacacg gcttgccaag tatcttgctg cagagagaac | 1740 |
| gcgccttggc atctttggga aagccgcttc acccttgct ggtggttgcc cccaaccagc | 1800 |
| tcaaagcctg gctccagcag taccacaacc agtgccagga ggtcctgcac acatcagta | 1860 |
| tgattcctgc caaatgcctt caggaagggg ctgagatctc cagtcctgca gtggaaagat | 1920 |
| tgatcagttc gctgttgcga acatgtgatt tggaagagtt tcagacctgt ctggtgcggc | 1980 |
| actgcaagca tgcgtttggc tgtgcgctgg tgcacacctc tggctggaaa gtggtctatt | 2040 |
| ccggggacac catgccctgc gaggctctgg tccggatggg gaaagatgcc accctcctga | 2100 |
| tacatgaagc caccctggaa gatggtttgg aagaggaagc agtggaaaag acacacagca | 2160 |
| caacgtccca agccatcagc gtggggatgc ggatgaacgc ggagttcatt atgctgaacc | 2220 |
| acttcagcca gcgctatgcc aaggtccccc tcttcagccc caacttcagc gagaaagtgg | 2280 |
| gagttgcctt tgaccacatg aaggtctgct ttggagactt ccaacaatg cccaagctga | 2340 |
| ttcccccact gaaagccctg tttgctggcg acatcgagga gatggaggag cgcagggaga | 2400 |
| agcgggagct gcgcaggtg cgggcggccc tcctgtccag ggagctggca ggcggcctgg | 2460 |
| aggatgggga gcctcagcag aagcgggccc acacagagga gccacaggcc aagaaggtca | 2520 |
| gagcccagtg aagatctggg agaccctgaa ctcagaaggc tgtgtgtctt ctgccccacg | 2580 |

```
cacgcacccg tatctgccct ccttgctggt agaagctgaa gagcacggtc ccccaggagg      2640
cagctcagga taggtggtat ggagctgtgc cgaggcttgg gctcccacat aagcactagt      2700
ctatagatgc ctcttaggac tggtgcctgg cacagccgcg ggccaggagg ctgccacacg      2760
gaagcaagca gatgaactaa tttcatttca aggcagtttt taaagaagtc ttggaaacag      2820
acggcggcac ctttcctcta atccagcaaa gtgattccct gcacaccaga gacaagcaga      2880
gtaacaggat cagtgggtct aagtgtccga gacttaacga aaatagtatt tcagctgcaa      2940
taaagattga gtttgcaa                                                   2958

<210> SEQ ID NO 4
<211> LENGTH: 295
<212> TYPE: DNA
<213> ORGANISM: Homo sapiens
<220> FEATURE:
<221> NAME/KEY: misc_feature
<222> LOCATION: (51)..(295)
<223> OTHER INFORMATION: exon 1

<400> SEQUENCE: 4
cgcgggcgta ggtgaccggc ggctttctca gttttggtgg agacgggcgc atgtgggcgc       60
tttgctcgct gctgcggtcc gcggccggac gcaccatgtc gcaggacgc accatatcgc       120 aggcacccgc ccgccgcgag cggccgcgca aggacccgct gcggcacctg cgcacgcgag      180
agaagcgcgg accgtcgggg tgctccggcg gcccaaacac cgtgtacctg caggtggtgg      240
cagcgggtag ccgggactcg ggcgccgcgc tctacgtctt ctccgagttc aaccg          295

<210> SEQ ID NO 5
<211> LENGTH: 51
<212> TYPE: DNA
<213> ORGANISM: Homo sapiens
<220> FEATURE:
<221> NAME/KEY: misc_feature
<222> LOCATION: (1)..(51)
<223> OTHER INFORMATION: exon 2

<400> SEQUENCE: 5
gtatctcttc aactgtggag aaggcgttca gagactcatg caggagcaca a                51

<210> SEQ ID NO 6
<211> LENGTH: 71
<212> TYPE: DNA
<213> ORGANISM: Homo sapiens
<220> FEATURE:
<221> NAME/KEY: misc_feature
<222> LOCATION: (1)..(71)
<223> OTHER INFORMATION: exon 3

<400> SEQUENCE: 6
gttaaaggtt gctcgcctgg acaacatatt cctgacacga atgcactggt ctaatgttgg       60
gggcttaagt g                                                           71

<210> SEQ ID NO 7
<211> LENGTH: 65
<212> TYPE: DNA
<213> ORGANISM: Homo sapiens
<220> FEATURE:
<221> NAME/KEY: misc_feature
<222> LOCATION: (1)..(65)
<223> OTHER INFORMATION: exon 4

<400> SEQUENCE: 7
```

```
gaatgattct tactttaaag gaaaccgggc ttccaaagtg tgtactttct ggacctccac     60
aactg                                                                65
```

<210> SEQ ID NO 8
<211> LENGTH: 58
<212> TYPE: DNA
<213> ORGANISM: Homo sapiens
<220> FEATURE:
<221> NAME/KEY: misc_feature
<222> LOCATION: (1)..(58)
<223> OTHER INFORMATION: exon 5

<400> SEQUENCE: 8

```
gaaaaatacc tcgaagcaat caaaatattt tctggtccat tgaaaggaat agaactgg     58
```

<210> SEQ ID NO 9
<211> LENGTH: 69
<212> TYPE: DNA
<213> ORGANISM: Homo sapiens
<220> FEATURE:
<221> NAME/KEY: misc_feature
<222> LOCATION: (1)..(69)
<223> OTHER INFORMATION: exon 6

<400> SEQUENCE: 9

```
ctgtgcggcc ccactctgcc ccagaatacg aggatgaaac catgacagtt taccagatcc     60
ccatacaca                                                             69
```

<210> SEQ ID NO 10
<211> LENGTH: 120
<212> TYPE: DNA
<213> ORGANISM: Homo sapiens
<220> FEATURE:
<221> NAME/KEY: misc_feature
<222> LOCATION: (1)..(120)
<223> OTHER INFORMATION: exon 7

<400> SEQUENCE: 10

```
gtgaacagag gaggggaaag caccaaccat ggcagagtcc agaaaggcct ctcagcaggc     60
tcagtccaga gcgatcttca gactccgagt cgaatgaaaa tgagccacac cttccacatg    120
```

<210> SEQ ID NO 11
<211> LENGTH: 59
<212> TYPE: DNA
<213> ORGANISM: Homo sapiens
<220> FEATURE:
<221> NAME/KEY: misc_feature
<222> LOCATION: (1)..(59)
<223> OTHER INFORMATION: exon 8

<400> SEQUENCE: 11

```
gtgttagcca gagaagaggg gtcagggact cttccctggt cgtagctttc atctgtaag     59
```

<210> SEQ ID NO 12
<211> LENGTH: 59
<212> TYPE: DNA
<213> ORGANISM: Homo sapiens
<220> FEATURE:
<221> NAME/KEY: misc_feature
<222> LOCATION: (1)..(59)
<223> OTHER INFORMATION: exon 9

<400> SEQUENCE: 12

```
cttcacttaa agagaggaaa cttcttggtg ctcaaagcaa aggagatggg cctcccagt      59
```

<210> SEQ ID NO 13
<211> LENGTH: 73
<212> TYPE: DNA
<213> ORGANISM: Homo sapiens
<220> FEATURE:
<221> NAME/KEY: misc_feature
<222> LOCATION: (1)..(73)
<223> OTHER INFORMATION: exon 10

<400> SEQUENCE: 13
tgggacagct gccatcgctc ccatcattgc tgctgtcaag gacgggaaaa gcatcactca      60
tgaaggaaga gag                                                        73

<210> SEQ ID NO 14
<211> LENGTH: 113
<212> TYPE: DNA
<213> ORGANISM: Homo sapiens
<220> FEATURE:
<221> NAME/KEY: misc_feature
<222> LOCATION: (1)..(113)
<223> OTHER INFORMATION: exon 11

<400> SEQUENCE: 14
attttggctg aagagctgtg tactcctcca gatcctggtg ctgcttttgt ggtggtagaa      60
tgtccagatg aaagcttcat tcaacccatc tgtgagaatg ccacctttca gag            113

<210> SEQ ID NO 15
<211> LENGTH: 96
<212> TYPE: DNA
<213> ORGANISM: Homo sapiens
<220> FEATURE:
<221> NAME/KEY: misc_feature
<222> LOCATION: (1)..(96)
<223> OTHER INFORMATION: exon 12

<400> SEQUENCE: 15
gtaccaagga aaggcagatg ccccgtggc cttggtggtt cacatggccc cagcatctgt       60
gcttgtggac agcaggtacc agcagtggat ggagag                               96

<210> SEQ ID NO 16
<211> LENGTH: 139
<212> TYPE: DNA
<213> ORGANISM: Homo sapiens
<220> FEATURE:
<221> NAME/KEY: misc_feature
<222> LOCATION: (1)..(139)
<223> OTHER INFORMATION: exon 13

<400> SEQUENCE: 16
gtttgggcct gacacccagc acttggtcct gaatgagaac tgtgcctcag ttcacaacct      60
tcgcagccac aagattcaaa cccagctcaa cctcatccac ccggacatct tccccctgct     120
caccagtttc cgctgtaag                                                 139

<210> SEQ ID NO 17
<211> LENGTH: 86
<212> TYPE: DNA
<213> ORGANISM: Homo sapiens
<220> FEATURE:
<221> NAME/KEY: misc_feature
<222> LOCATION: (1)..(86)
<223> OTHER INFORMATION: exon 14

<400> SEQUENCE: 17
aaggagggcc ccaccctcag tgtgcccatg gttcagggtg aatgcctcct caagtaccag      60
ctccgtccca ggagggagtg gcagag            86

<210> SEQ ID NO 18
<211> LENGTH: 119
<212> TYPE: DNA
<213> ORGANISM: Homo sapiens
<220> FEATURE:
<221> NAME/KEY: misc_feature
<222> LOCATION: (1)..(119)
<223> OTHER INFORMATION: exon 15

<400> SEQUENCE: 18
ggatgccatt attacttgca atcctgagga attcatagtt gaggcgctgc agcttcccaa       60
cttccagcag agcgtgcagg agtacaggag gagtgcgcag gacggcccag ccccagcag      119

<210> SEQ ID NO 19
<211> LENGTH: 97
<212> TYPE: DNA
<213> ORGANISM: Homo sapiens
<220> FEATURE:
<221> NAME/KEY: misc_feature
<222> LOCATION: (1)..(97)
<223> OTHER INFORMATION: exon 16

<400> SEQUENCE: 19
agaaaagaag tcagtaccca gaaatcatct tccttggaac agggtctgcc atcccgatga       60
agattcgaaa tgtcagtgcc acacttgtca acataag                               97

<210> SEQ ID NO 20
<211> LENGTH: 139
<212> TYPE: DNA
<213> ORGANISM: Homo sapiens
<220> FEATURE:
<221> NAME/KEY: misc_feature
<222> LOCATION: (1)..(139)
<223> OTHER INFORMATION: exon 17

<400> SEQUENCE: 20
ccccgacacg tctctgctac tggactgtgg tgagggcaca tttgggcagc tgtgccgtca       60
ttacggagac caggtggaca gggtcctggg caccctggct gctgtgtttg tgtcccacct     120
gcacgcagat caccacacg                                                   139

<210> SEQ ID NO 21
<211> LENGTH: 39
<212> TYPE: DNA
<213> ORGANISM: Homo sapiens
<220> FEATURE:
<221> NAME/KEY: misc_feature
<222> LOCATION: (1)..(39)
<223> OTHER INFORMATION: exon 18

<400> SEQUENCE: 21
ggcttgccaa gtatcttgct gcagagagaa cgcgccttg                              39

<210> SEQ ID NO 22
<211> LENGTH: 110
<212> TYPE: DNA
<213> ORGANISM: Homo sapiens
<220> FEATURE:
<221> NAME/KEY: misc_feature
<222> LOCATION: (1)..(110)
<223> OTHER INFORMATION: exon 19

<400> SEQUENCE: 22
gcatctttgg gaaagccgct tcacccttg ctggtggttg ccccccaacca gctcaaagcc       60

-continued tggctccagc agtaccacaa ccagtgccag gaggtcctgc accacatcag    110

<210> SEQ ID NO 23
<211> LENGTH: 100
<212> TYPE: DNA
<213> ORGANISM: Homo sapiens
<220> FEATURE:
<221> NAME/KEY: misc_feature
<222> LOCATION: (1)..(100)
<223> OTHER INFORMATION: exon 20

<400> SEQUENCE: 23
tatgattcct gccaaatgcc ttcaggaagg ggctgagatc tccagtcctg cagtggaaag    60
attgatcagt tcgctgttgc gaacatgtga tttggaagag    100

<210> SEQ ID NO 24
<211> LENGTH: 121
<212> TYPE: DNA
<213> ORGANISM: Homo sapiens
<220> FEATURE:
<221> NAME/KEY: misc_feature
<222> LOCATION: (1)..(121)
<223> OTHER INFORMATION: exon 21

<400> SEQUENCE: 24
tttcagacct gtctggtgcg gcactgcaag catgcgtttg gctgtgcgct ggtgcacacc    60
tctggctgga aagtggtcta ttccggggac accatgccct gcgaggctct ggtccggatg    120
g    121

<210> SEQ ID NO 25
<211> LENGTH: 79
<212> TYPE: DNA
<213> ORGANISM: Homo sapiens
<220> FEATURE:
<221> NAME/KEY: misc_feature
<222> LOCATION: (1)..(79)
<223> OTHER INFORMATION: exon 22

<400> SEQUENCE: 25
ggaaagatgc caccctcctg atacatgaag ccaccctgga agatggtttg gaagaggaag    60
cagtggaaaa gacacacag    79

<210> SEQ ID NO 26
<211> LENGTH: 145
<212> TYPE: DNA
<213> ORGANISM: Homo sapiens
<220> FEATURE:
<221> NAME/KEY: misc_feature
<222> LOCATION: (1)..(145)
<223> OTHER INFORMATION: exon 23

<400> SEQUENCE: 26
cacaacgtcc caagccatca gcgtggggat gcggatgaac gcggagttca ttatgctgaa    60
ccacttcagc cagcgctatg ccaaggtccc cctcttcagc cccaacttca gcgagaaagt    120
gggagttgcc tttgaccaca tgaag    145

<210> SEQ ID NO 27
<211> LENGTH: 655
<212> TYPE: DNA
<213> ORGANISM: Homo sapiens
<220> FEATURE:
<221> NAME/KEY: misc_feature
<222> LOCATION: (1)..(228)

```
<223> OTHER INFORMATION: exon 24
<220> FEATURE:
<221> NAME/KEY: polyA_signal
<222> LOCATION: (636)..(641)

<400> SEQUENCE: 27
gtctgctttg gagactttcc aacaatgccc aagctgattc ccccactgaa agccctgttt     60
gctggcgaca tcgaggagat ggaggagcgc agggagaagc gggagctgcg gcaggtgcgg    120
gcggccctcc tgtccaggga gctggcaggc ggcctggagg atggggagcc tcagcagaag    180
cgggcccaca cagaggagcc acaggccaag aaggtcagag cccagtgaag atctgggaga    240
ccctgaactc agaaggctgt gtgtcttctg ccccacgcac gcacccgtat ctgccctcct    300
tgctggtaga agctgaagag cacggtcccc caggaggcag ctcaggatag gtggtatgga    360
gctgtgccga ggcttgggct cccacataag cactagtcta tagatgcctc ttaggactgg    420
tgcctggcac agccgcgggc caggaggctg ccacacggaa gcaagcagat gaactaattt    480
catttcaagg cagtttttaa agaagtcttg gaaacagacg gcggcaccttt cctctaatc    540 cagcaaagtg attccctgca caccagagac aagcagagta acaggatcag tgggtctaag    600
tgtccgagac ttaacgaaaa tagtatttca gctgcaataa agattgagtt tgcaa         655

<210> SEQ ID NO 28
<211> LENGTH: 26664
<212> TYPE: DNA
<213> ORGANISM: Homo sapiens
<220> FEATURE:
<221> NAME/KEY: misc_feature
<222> LOCATION: (910)..(13104)
<223> OTHER INFORMATION: exon 1: 910-1154; exon 2: 1736-1786; exon 3:
      1925-1995; exon 4: 3025-3089; exon 5: 4361-4418;
      exon 6: 5582-5650; exon 7: 7075-7194; exon 8:
      8186-8244; exon 9: 12878-12936; exon 10:
      13032-13104;
<220> FEATURE:
<221> NAME/KEY: misc_feature
<222> LOCATION: (13756)..(22917)
<223> OTHER INFORMATION: exon 11: 13756-13868; exon 12: 15283-15378;
      exon 13: 16278-16416; exon 14: 16498-16583; exon 15:
      18583-18701; exon 16: 20349-20445; exon 17:
      22172-22310; exon 18: 22879-22917
<220> FEATURE:
<221> NAME/KEY: misc_feature
<222> LOCATION: (23045)..(26452)
<223> OTHER INFORMATION: exon 19: 23045-23154; exon 20: 23795-23895;
      exon 21: 23973-24093; exon 22: 24354-24432; exon 23:
      25026-25170; exon 24: 25812-26036; polyadenylation
      signal: 26447-26452
<220> FEATURE:
<221> NAME/KEY: variation
<222> LOCATION: (826)..(23879)
<223> OTHER INFORMATION: s at positions 826 and 23180 is G or C; y at
      positions 1914, 5568, 7165, 16431, 1857 and 20486
      is C or T; n at position 13128 is t or tgat; r at
      positions 22211 and 23879 is A or G.

<400> SEQUENCE: 28
tatcaggtga ctgaattcta tattctgaag taggagatac tgttattgct gttattacat     60
tttacacata agaaagctga ggctctgaga ggtcaagatc acgcagctaa caaatgagcc    120
aagactcttg ctttagagct tgtcctctat tcttgctttt ctttccaaaa aacactacaa    180
tttttgtttt gttttgtttt gttttgagac agggtctcga ggtgtcaccc aggctggagt    240
gcagtggcgc gatttcgact caccgcaacc tccgcctccg cgcttaagcg attctcctgc    300
ctcagcctcc caagtagctg ggactacaag ctcgggacac cacgtaaaaa tgatcaagtt    360
ctaacatgta tgcatacgaa ttacaatgga aataaaatta gcaaagcgct tatgctaatg    420
```

```
ctcaatacaa ttgatttcct cacatttaat cctcacaacc actacaacca cctctaactc    480
aagctctgag ggactgacgt gcccggagga cacagctctt atctggtgag aacaggagcg    540
ttttagcgaa actccaaact cctaggtccc gccttcccca ggaaggcttt tcctggcact    600
gtgcttccgg aagtcccgcc ccaggagaaa acagcttcc ggaaaaaatt gcggccggca     660
aaccggaaca gaactagggg cggggccgct tgagacgctc tagtattcct ctactctatg    720
gccactgtca attgacaagt cccgagcggt aaagctcctt tctattggat gagcagcctc    780
gcgtaggcgg gaagctcggt gcacggcgcg ctgattggct ggatcsgcca tgcggagcgg    840
ctaggtggtg cacgggaaac gcgggcgtag gtgaccggcg gctttctcag ttttggtgga    900
gacgggcgca tgtgggcgct tgctcgctg ctgcggtccg cggccggacg caccatgtcg      960
cagggacgca ccatatcgca ggcacccgcc cgccgcgagc ggccgcgcaa ggacccgctg   1020
cggcacctgc gcacgcgaga gaagcgcgga ccgtcgggt gctccggcgg cccaaacacc    1080
gtgtacctgc aggtggtggc agcgggtagc cgggactcgg gcgccgcgct ctacgtcttc   1140
tccgagttca accggtcagt caacgagcca cgccccgtcc cgctgggccc tcagtgcggc   1200
gcagcctctg agcatcgggg cacctcccag ggcttcggct tccctgcttc acacatgtgg   1260
ttcactgttg cggggttcg tggagttatg gtgggtggga aatccgagat tctttgcatc      1320
catgtgattt ctgcggatct gtgaagaact tcaggcctgg gtctgagcgt cctttccca     1380
acccttgggc cccggcctgg ctgtcagcac tttcggagct ccaccctctt ccgtgcaccc    1440
caaggccagt gtgtcgttgt tagcgtgtgg ggtggacaga tctggtgtgt agccggtggt   1500
ggagaaagga ctcattttgt cctagcaccc acacacacag gcccccactc ctctccacct   1560
ctgctaagga gggctcaaaa cccaccagca taaatgtggc tcggtagtcc aacgtggact   1620
tttaatttt ttttcttttt tttttttcca gagtctacaa taaaacatct aattggtgtc       1680
agagagttta cagaataaaa ccttctgaat gtcttgtgta atgtttgtct tgtaggtatc    1740
tcttcaactg tggagaaggc gttcagagac tcatgcagga gcacaagtga gtcagtctct   1800
tgctttcgga gggggagttg attacggggc ttgaaagccg aaatgagagg ccagttgttt   1860
tttatagcaa aagtggtcct tgttctgttc atgttatcct gtttaaatgt tttytcattc     1920
ttaggttaaa ggttgctcgc ctggacaaca tattcctgac acgaatgcac tggtctaatg   1980
ttgggggctt aagtggtgag tatattcttt gcagtgtcag aggctggtgg aagtctctg     2040
ggattttaac cggcttacc attttttccaa gtctggggtg gcagctact ttttttttt        2100
ttttttttt tgtcagtggc gtgatcttgg ctcactgcaa cctttgcctt ctgggctcag      2160
gtgatccct cacctcagcc tcccaaatag ctgggaccac acgtgtgccc catcacacct      2220
ggctaatttt ttttgtatgt tttgtagcga cggggttttg ctatgttgcc caggctggtc    2280
tcaaacttct gcgatcctcc tgtctcggcc tcccagagtg ctgggattac aggcatgagc    2340
caccgcacct ggcctggaat tctttttata ccagcccagt cagcagcagc acagagcatt    2400
aaaagctgtg actcaggaga acagattta atatggatac cacctcttaa gtgttaccat     2460
ccacttagtt tcttgcgttg cggggacaga gatttgtggc agtaaactgg agagtctagc    2520
agtggtgatt acagttaata tgtttaccgc agacgccatt ggcacattgg cagccacaca    2580
catacccact gtccagatta ccctgtcatt tatgtctatc aaccggaagg tcaggattgt    2640
gttgcagcca aattgtgtgg gcttggtggc atgaccgga aggagtgaag tgttagacca     2700
gtctccttc tcagggctga gactagggtg aggcacttag ggtgccagcc cttcacttgc      2760
```

-continued

```
atgattcctt acattttgca cactgggtgc cttgctgctt caccctagtg acagctcagc    2820
ccattctaga ggcatttaaa gaatatttgg tgtctgttac acctctagct ggcatcactt    2880
ctgctctgta catcttccct ggttgtactt ccaaagctgg aaggtggaga tgtagataaa    2940
tagttggatt agtacgggt gctcctcctg ttagtgacga caggtcaaat tgatgagaga     3000 tctgattta tgcatccttt ttaggaatga ttcttacttt aaaggaaacc ggcttccaa      3060 agtgtgtact ttctggacct ccacaactgg tgagtctttc ctgacacatc tttcaaaagc    3120
aatctttcct tttgtaatat cagtaacaag aattttcctt tttgcaaatc agtcttctgc    3180
cctccagaga tacctggtcg ttgaaacgct tccccttca agttaaaaag acttgagttc     3240
tgattaacta tgtgaccttg atcaagttac tttaccttc tgagctttag tttattcatc     3300
tataagatga ctatcacgtt tcatagagtt gttaaagatt aaatgacgta gcagcacata    3360
taaagcacta aatcactta ttagatatat gtttggcacc aagtaggcac acaagaaagg     3420
gcagcttttg tttttattca ataaattct gacatcttct tacctttcag tccagcttat     3480
tacactcttg agaaggcgtg tgtgtgttgt tgaatataac agttcattt ccagtcctta     3540 agaagaaagt caccaagacc tgttaagtct ttccccaaaa taacgtttga aatccatcca    3600
tttgtctctt attgaggcct tccttatttc tgttttctat gcctgtaaac tacaatagcc    3660
tcccatattc attctcgcct tcctgtaatc catctgccac acagcagcca gagaggtcac    3720
ttcaagacag aaaagtagtg tgtcacttgc caccctaaag cccttcatgg gctccccatt    3780
gcaatacaat caaaacacct tgatatggcc tacaagtcct gtaggccccg gccgctaccc    3840
acacttccat ctgtacccat cgctgaactg cagctgcatg ggctgactct tatgtccctc    3900
taactccctg gccacttcag gactttcgcc cttccgcggg ttccctctgc ctcttctaat    3960
tgctgcctat attgttactg aaccttcagg gctcagctag agggtcattt actccagaac    4020
tgcctcttct tctctagaca agttggatcc cagccttctg tatttttcat tttccttgca    4080
gagcacttag cataatgcca ctaagctgtt tctgttatcg tgtttccttt tgtctcctcc    4140
actggcctga ttagagcaag gcctccatct cttttttcctg ctatatcctt ggcatctgat   4200
ataatggata ctcagtaaat atttgtaata atgatgttc aaaatattta ctaagctttg     4260
ttttatgttg ataccatattg gtaaccttt aaatacttga atagttgctg tgttctacat    4320 tgttcaacc ataactgctc atttctttgt ttttcattag gaaaaatacc tcgaagcaat     4380
caaaatattt tctggtccat tgaaaggaat agaactgggt acgtctttgt ctgtgactca    4440
tcctctgcta tttctaactt atatatgccc tgacctctca aattagaatc cattaaaaac    4500
atcaacatca aacctcaaaa tcaaatgctt catcaccacg agatttttt ttttttttt     4560 ttttttggat agagtcttgc tttcttacca ggctggagtg cagtggcatg atctcggctc    4620
actgcaacct ccacctcctg ggttcaagcc attctcccac ctcagcctcc tgagtagcta    4680
ggactacagg cgcatgccat cacgctcagc taatttttg tatttttagt agagacgggg     4740
tttcaccatg ttggccagga tagtctcgat ctcttgacct tgtgatctgc ccgcctcagc    4800
ctcccaaaat gagctaccat gtggctggag atgggatttc taaatagtga catttctgt     4860 gttcccacct catgctgtaa aaatagggc caggtcggca ggagtgattg aacagctgat     4920
gcctgcctgt gtacatgctg tgtggcattc tccatccaga cggcaggct cctgcctcag     4980 ttccagaggt gcttctcgtc gttgagttgc tttgagttgg gggcgggggt gacaagggtt    5040
ccctagaggt tttgtggcca actttgtaca ttgaaacgca gctccagctg cgcagggggg    5100
cttacagcct cttgatggga agaggcctca ctgaggatgc tagtagggct cttgtcctgg    5160
```

```
cactggtgtg tatctgtggc ttgttaatac tcctctttta tagaaacact aatactttgt  5220
ttcaaaatat acatcagctc ttctggtttg cgatgatagg ttccctggct tcactattct  5280
gtttgttaac ttgggtctct gaaagttgag tactagtttc ttgttttttca atttttaacg  5340 gatagtcacc aaagattata atgtcttttc atctggctgt agtaaatata aatggctgac  5400
caaaatacac ttttatttat ttcctaaaaa tggtaatctc cttagaaagt ctggttttcg  5460
tgtcagattc ccaccataat tctgaggcaa ttcagttgct cgtggttggt gatcctgaag  5520
ttactcttcc cacacatctt cactaatgca atcacttttgc tgttgtgygg ttttcttgta  5580
gctgtgcggc cccactctgc cccagaatac gaggatgaaa ccatgacagt ttaccagatc  5640
cccatacaca gtgagtatga aagccaggtt tcccaggagg agggtgtacg tcctgagtaa  5700
agaaaacatg gatgaaaata gaaactgaac acttgctgtg ggcaccctgt tttgtgttct  5760
gagcatgatt agaaaattta gttgaggaat gaagatatgg ctcctgccct ggcttataaa  5820
cttacggatg tctgacttat gcctaatgat agtgattatg ctttggaata ttagataatc  5880
aagcactgtt ggtaaataga ttgcattcaa gtttgcacat tcattgcttg gaggtttttt  5940
cccacaggcg taatacctc ttttgatcag acgatcatga agaggtttgc acagatagat  6000
ttttttaaat aaataatgat tacagcaacc taaagaagt gttgttgggg gttagaagct  6060
cctgcaaatt ccgaagtatc agggccagat gatgtggtct tagcttagga aaagagttag  6120
tcttgtcctt gaacttggct aaagacattc atgtctggtt ttacttacat gtgaagagag  6180
taccaagcag taggggtatt tccttgttag tactaactaa tgtgatgctt actaagtagt  6240
gctgatgggt gacagaccag agcacccagc aaaggccaga gaagtccaga acctggcgag  6300
gagatgaggc ttcactgac tgaaggcaga aggcagcagg gaggagagga atgtgccgga  6360
gcaatggcac aagtgctcct aggccagtgc tgtgatgagc tgatcagcac tcccattgcc  6420
tggcttgctc ctcctgctca gatgccttct ctcacctgac cctgctgta gccacccca  6480 gcctgagttg catccacctg tttgttgtcc atttccagca ccctgttctt cgctccatgg  6540
catgtgacag ttaactttca tatgtgattt gcgtgatcga tgttaacatg ctcagttttg  6600
ccgatcactg ttttttcagt gtccagcggc cctcagtgag tgaacttacg ttcattctcg  6660
ttgcagctgt gctttagctt cttagagcag cgaattttttt tcccttgatc ttgagccta  6720 actaaatgta aaatgaggct ccttcttgag ataggtaccc tttgggtcta tgtgttttag  6780
cgggagtgat gataataaat aagcatgtct acaacccaca tgctgtttag ataacacgtt  6840
gttgagttgg tactgtggcc gaggctgtga gctaagcaga aacataaaca ttaataggac  6900
ataggtgcag cccagaaacc aggtaggaag ttaactaact agttatttcc tactgtatag  6960
taaaaggtgt gctgatttaa ttggcgttct ggcattccca tgtatgaacg tctgggcctt  7020
ggctgtcagc tcaccttgtg cagtgtgtaa tttggtggta tctgtactga ccaggtgaac  7080
agaggagggg aaagcaccaa ccatggcaga gtccagaaag gcctctcagc aggctcagtc  7140
cagagcgatc ttcagactcc gagtygaatg aaaatgagcc acaccttcca catggtaata  7200
gtataaacaa aacagagcag cagaaaggct tgcgttttct taattctctg ccttgtaatg  7260
cttgtagaga gtcattattg taagaaagcc aggtgtgtaa acagatcctt cttcctgggc  7320
ttactataac ttggcccgtt ggggaatga gaagggttgt tgtaaaggtg gcagcctgca  7380
actttaataa tgaccagtcc acagttttgg ccacccaggg tctgggtagg cccaaaactg  7440
tgttctgttt tcccagagga gaacagggcc tgacaaacgg attcattttg tatttttcat  7500
```

-continued

```
taatgtaaca tttatgcaaa ttttccatta atgtggaaac tataactgct aagccaatga    7560
gacagtcaaa tcagtgagag gctctgcacg tcttccagaa tgacagccca ctgggaaacg    7620
gagttaaaag tccaagatga gatgtagctc aggagtcagg ccgcttcggg agtttgttgt    7680
ccttaacaga aggtcagcgt tggcaaagct cggcagctcc tctttctgtc ctgaggtctt    7740
gtctagtgac tgagaacagg ctgacccta tgtgctgtcc ttgtttggat ggcaccgggt     7800
aaagactgac accagcattt tctctgcagg cctttgaact tttgtgttat ttcatatatt    7860
atatgtgtta taaagcacat tacaatatat ttttctctgt cttctccagt cctaggtgaa    7920
atgtgtcatt taaaaaaaat ttcacttgcc attctaaagt ttttctggtg agagttttgt   7980
gttttttcatt tacgcaaaca catctccaca taagtaggga aaaaagtct tcttgagtat   8040
attagtgtct tcagccttg tattgggaca gtagcgtcca ttaatttta tgtgaagtga    8100
aattaggtat cgggtcataa tcagtctgtg atgtcttcac agctttcaca tttaccttgt    8160
gataatcaag tgtgtttttc ctcaggtgtt agccagagaa gagggtcag ggactcttcc    8220
ctggtcgtag ctttcatctg taaggtaagg aagactttcc ggagggctgt acatgactgg    8280
ggtcttggtc agcgacctct ggtttgcact ttttcattaa tttgagggta ggcactcctg    8340
ttacctgaga caagaagaga tagcagatct tcagaaaagc tgatggaagg ccgggtgcag    8400
tggctcacgc ctgtaatccc agcactttgg gagtccaagg caggtggatc acgaggtcag    8460
gagtttgaga acagcctgac caacgtggtg aaaccctgtc tgtactaaaa atacaaaaat    8520
tagctgggtg tggtggcgca tgcctgtaat cccagctact tgagaggcca aggcaagaga    8580
atcgcttgaa cacaggaggc ggaggttgca gtgagttgag attgcaccat tgcactccag    8640
cctgggtgac agagcaagac tctctcaaag aaaaaaaaaa ttcgatagaa atgacactgg    8700
caatgagcct gcaacaagta ttactactga cctttcataa ttgtcatcac ttgtaggttt    8760
cagagtttag atgctctgtt tctcaaaata accccatact tttatttcct tttaaatttt    8820
tttccagtgc cctgtcagcc tccgtacatt tttttttttt tttttgaga ccatgtctgt     8880
ctccatcgcc taggctggag tgtgcagtgg cacaatctcg gctcactgca gcctccacct    8940
cccaggttca agtgattctc ctgcctcagc ctcccaagta gctaggatta taggtgcgcg    9000
ccaccacacc cagttaattt ttgtattttt agtagagatg gggtttcacc atgttggcca    9060
ggctggtttc actcctgacc tcaggtgatc cacccacctt ggcctcccaa aatgctggga    9120
ttacaggcgt gaagcactgt gcctggtcca tattctttta tatttgccaa tgattggtcc    9180
ttttagaatt cagaaattat tgaaggcagc tgtgtttgtt ttccttcaac tccatcaggc    9240
ctttattcaa agtcttttaa ctctgttta ctttatttca ttccctgca atagctaagg     9300
tctaacacca gattaattgg aatattagct agcattcaca aaggcctaga tctgtaactc    9360
tgaaattggt caaattccat taaaaatttt tgttacaata agctgtttgt aagatctgac    9420
tagtggctta ttttaatag aattttgcat taaaatttta tcaatacaat ttgcaacaaa    9480
tttgtctaaa tatgtgaaaa gatttcattg cctttttgtg ggcttagatt attttttaat    9540
gttgattttg aaatatattt ggaattgtta tctaaattct aaaagctaca agtgaaaata    9600
ataatgaaag taagtagtta atattagtgg caagatcatt gccagtatca tttctatcga    9660
tttatttgaa taatgtgatt ttcataaaag ttaagtacta ctgttaacag gcttattact    9720
tgtatgtttc tgagttttag atagcaaaat cattttttaa agttttaaaa atattttatt    9780
tttgataatc tatattttata ttgtctgatt tttaaactgt tttctatggt aatctttaaa    9840
tcgtattcct gctttccgga ataggtaaca gtgagcatga tgaaaagtga caagctcact    9900
```

-continued

```
tttacacact cgggcagttg ccctattatc aggcagccgt tcctgggggc tgccagctgc    9960
ctgccctggc ttttccatct ccttccttgc tgtcttctgc ggctccttct gagggctgct   10020
gtcactggat tagcctataa cgcctttccc ctcttctaat taatttgctg ctctcaggtg   10080
aggttttgga aagcaataaa gctgagctag gtcaagttcc aggagtctct tggcatgagg   10140
acctgaaaaa ctcatctgtt ggaagacctc ggctttgggc agctggtgca ctgtggggc    10200
gttattggct gcgttctggc tctcatcagt cttccagata ctctgcattc ctcagagagg   10260
aacatatctc catgggttga gttcagctcc cagggagatg ggtttccctg ccttaagtcg   10320
gcaagtacct ttttttttct tttttgaga cagagtctcg ctctgtcacc aggctggagt    10380
gcagtggtgc gatcttggct cactgcaacc tctgcctccc agggtcaagc agttctcctg   10440
cctcagcctc ccgagtagct gggactacag gagcgcacca ccatgcccag ctaattttg    10500
tatttttta gtagagacgg ggtttcacca tgttggccag gatggtctgg atctcttgat   10560
ttcctgatcc gcctgccttg gcctcccaaa gtgctgggat tacaggcgtg agccatcatg   10620
accagccttt atgtttcttt gtttgttttg tttttctgag atggagtctc gctctgttgc   10680
ccaggctgga gtgcagtgtt gccatctcga cttactgcaa cctctgcctt ccaggttcaa   10740
gtgattcctt gcctcagcct cccgtgtagc tgggatcaca ggtgcctgcc accatgcccg   10800
gctaattttt gtattgttag tagacacagg gtttcgccat gttggccagg ctagtctcga   10860
actcctgacc tcaagtgatc tgccttcctc agcctcctaa agtgctgggg ttacaggagt   10920
gaaccaccat gcccagcctt caattacctt ttatttattt tatttattta tttattttg    10980
agacggagtc tttctgtgtt gcccaggctg gagtgcggtg gcgcaatctt agctcactgc   11040
aacctcctcc tcccaggctc aagtgattct catgcatcag cttcccgagt agctgggact   11100
tcaggtgccc gccaccacac ttggctaatt tttgtgtttt tagtagagac ggggtttcac   11160
catgttggca aggctggtct tgaatttctg acctcaaatg atcctcctgc ttcagcctcc   11220
caaagtgctg ggattacagg cgtgagccac tgcccccaac agcaagtacc ttttaaacat   11280
tagagacatt tagttgccat cctcaaaccc gtttgggtgt gtggagagaa tgttgggtcg   11340
tgacatggtt gttagttatc taaagatgtc agccatcaat catcactgtg tgatgtgcac   11400
actgaagctg taatccttca tctaggatga tattttttaa gatggaaaat tctacaaccc   11460
tgagaataag gatttcagat ccaaatttga gactcagccc tacgagtaac tctttaactt   11520
cagagagtta aaagaagatg cacagttgat gaagatttaa aggagaaaat ggaaatcaaa   11580
tgtcatttag cactcaaagg cctacatgtc atttctgaca ttttctgtt tgtgtgaaat    11640
ttttttttc ctataaaatg attgtgaagt tttctggtag aattattgtt tgcctttcta   11700
atgtaatagc atattagggt tttttttttt ttcttttct tttttgaga cagagtctca    11760
ctctgtcgcc caggctggag tgcagtggca cgatctcggg tcactgcaat cttccgcctc   11820
ctgggttcct gcctcagcct cccgagtagc tgggactaca ggcgcacgtc accacacccg   11880
gctaattttt tgtattttta gtagtgacag ggattcaccg tcttagccag ggtggtcttg   11940
atctcctgac ctcatgatct acccgcctcg gcttcccaaa gtgctgggat tacaggcatg   12000
agccgctgtg cctggctatt agagattttt tattataatt tatctccaag ataaaagcag   12060
tgacattata ttgccacata attgaaaaat acaagagaaa taaaaatcat ccatgctttt   12120
gttagcctat cactgtcatt gaaatattat gttacatggc agtttgcttg ctggttgctc   12180
tgttaggcaa cgctctggtg acattccttt agctattaat tgaggaatgt agaatgacag   12240
```

```
aacagtgttt ctcctcaatg atacttgaag gatatttatt aactttcata ttgaattaca   12300
ttttattaaa tttataatga gttaatgctg ggaaataaaa cactgattta agtcattttg   12360
gcttttagta ctaaagcatt tgacaataaa tgacttcttc agaatatggt ataccttctg   12420
aaagcaataa acgcatttta atgaattgta aggaaacaac atcattttat tttttatttt   12480 ttttttgag acagctttc gcttttgttg cctaggctgg agtgcaatgg cgcgatctcg   12540
gctcactgca acatccgcct ctgggttcaa gcgattctcc tgcctcagct tcctgagttg   12600
ctgggattac aggcacgtgc caccacgcct ggccaattt gtattttag tagagacggg   12660 gtttctccac gttggtcagg ctggtctcaa actcctgacc tcaggtgatc tgcccgcctc   12720
agcctccgaa agtactggaa ttacaggcgt gagccaccgt gcctggccaa cattattatt   12780
tttttttaat ctagaaaaat acacttctaa gaaaattgat taaaaccaac cttcttcatt   12840
agcccctaag atcacatcta tgttctcttt gttgcagctt cacttaaaga gaggaaactt   12900
cttggtgctc aaagcaaagg agatgggcct cccagtgtga gtgtgggggg taaggcttct   12960
ggggactcac tgggtacacc tgtccactta aggaaatcac atttcacaga ggccttgcct   13020
cttcatttca gtgggacagc tgccatcgct cccatcattg ctgctgtcaa ggacgggaaa   13080
agcatcactc atgaaggaag agaggtgaga tgcctggttt tcttgatnca gcagttacag   13140
gtagggtctg aaatgctggg cagagtctgt cttcttcagg ccctacagac accactttg   13200 aaggacgtgg aacagtttgg acatcactca gctaagtgat aaaatggcct cttttatctg   13260
tgtttgtccc gcatgtcaac acggctgcat tcgagcattt ttgtagattg tccatttagg   13320
atctagtcac cgtcctcctt aaagggtgca tgctttcctt ggtacttgag ctcaggacag   13380
tgtctaacaa cagaccccat atggatgggc ctggggttta tggtccagag gaatgccaca   13440
gtattctatg tcaagatatt tcctctgact tctgaggaca ttaggaccag tggccacaga   13500
ctgaagaaaa ccttaatgcc aagcctcctt tcctggccag tgtaggcctg aagtgcctca   13560
acctgacagt tacctgttta ggtatccaca aagagaccag aagggtgttg atggtgatgt   13620
gtaaagttgg ttttgtgctt tgtttacctc tcagctcact ggataggata tgtcatgtta   13680
gcagttgcct tgaaggcagt tcagtttggt ggctgagctg tgaccccag tgggcgggct   13740 tatttggttt tgcagatttt ggctgaagag ctgtgtactc ctccagatcc tggtgctgct   13800
tttgtggtgg tagaatgtcc agatgaaagc ttcattcaac ccatctgtga gaatgccacc   13860
tttcagaggt aatgaggggt ctctagggtg ggagaagtga gagctgaaac ccagcccagc   13920
atcgacatgg gcatcttgtg gcaagagctg tgtttctggg aagaccacta tctgggttta   13980
cagttcagag gccggcactc ctgccttaag tcactgttgg tagttggtgg gctccggtgt   14040
acacagcctc aaagtgaaat tagaaaagat tgaaaactag aaacaactga ggactagaaa   14100
ttcaactaga actcttacag ctcttatacc agaagaaatt ctagaacttt tttgaattct   14160
aactaatgcc ccagattatc atttggatta ttttgaactg aattaatttt cttccattac   14220
ctgcattgaa acaaatgagg tgggtcagag tgtgtgagac tgtcgtggtc aagagtccgt   14280
gttatgggat ggactcacag ctggggaatg tcttttgggc taactgccac tctgttgttg   14340
tcctctatcg aagttaacca gttttgcggt tcagctttca ttccagatgg aatcatcttt   14400
gacccaccta tctgagtttg aatcttttcc cccactctta atggtttacc tgtatttttc   14460
ctgttcctag tttgtatcta tctgtatttt ttcacttgtt tttttctact taccacaaca   14520
aatccttttg ggctgctgta cccccttccga gtcagagcgt taggagttgt ttcatggtct   14580
gctttattct ctgtgggtga atttggatgc gctggtagcc ccggctttgt attttaatcc   14640
```

```
agttttgggc agcaaaacct cttcaatgaa tcaggtgtca tttgagagcc atgtgtggat   14700
gtgtgatgat gctgggatag ataaaaatag ctactgtgta tatttctttt taaagggaac   14760
tggagggaaa cacatcagca tgttagtaag tggtctgttg tccaggtggt gaaatttcag   14820
atgattttca tttctcgtgc ctgtgtctca ggtcctctgg aaggcagaca ccagggtggc   14880
attggaggtg caggaggttt attcgaggaa atttgactgt gagagaggaa ggagagaggg   14940
agcaggagga ggcagggaga gcctgggtct ggctttgcag gttggacccg tatgagtgga   15000
gagggtagga aggaagtgca gtgctgagaa aggatcagcc aggcctactg aaagcccag    15060 agcagagctt gccagataca ggaatcccac gtccattgga aatggcccag caccggggtc   15120
tgccgtgagc agcctgctgt gagagcatgg cctgggcgtg gaggctgtca gctcactgca   15180
gtgctgcaga gggccgcacg ataccctcc ctggctgcgt ggtccctgtc ttggtgtgtc    15240
ctgagtctgc atcactttgt aaagcccac tcttctgccc aggtaccaag gaaaggcaga    15300
tgcccccgtg gccttggtgg ttcacatggc cccagcatct gtgcttgtgg acagcaggta   15360
ccagcagtgg atggagaggt atggagccca gcccagcggc acttgggta actcttctgg    15420 gcagtggtgg attcccctt cctcccctcg tgctctttcc agcgctacct acccttctgc    15480
acctgcctaa actttctgtg ggattcctgc cttcccagaa ttctaggctt cccagatctg   15540
tgctacactc gtgaagaaaa tgcaccgcta ggtggcgcag tgtccacacg attccattta   15600
ttttacaccc tccacactct tcagggtgtc tgaacaaata ctgccgtttg gttgaggatt   15660
ccataagtga attccaaaga agagattgca gctataaaat gatagcttcc atttactgaa   15720
tgcccacttt gtgggaggca gtgtgtgaaa tacccttcat ttcacttcat ttcctctagg   15780
gtcgtcgcca gcagccctgg gaggtagatg tttagtcact ggaaggcatc tttttcctcg   15840
gggcatcgct ggccagggcc aggtggagga gtatgagttg agctcgggtg cggggtgacc   15900
ttgggctgct ttttggcccc tgcccgtatc tccccacatg gcccgtttac ctgcccctca   15960
ctccatggcc tgctctcctg ctgtctcttt cattcctcag ggtttgggtc ccctatttgt   16020
atgccctgga catcttcttt ttcttgtttt tcctctcact cttcccagca cacctgaaag   16080
gcagctgagc tagggaacac cgggctttga dacagcagga gtgggaccat gtttggccat   16140
gtagtaacac tgcttggggc aagtcactga actgtttgaa cacctcatcc tcattaccac   16200
tcctgagctc agcaccactc ctcaggggga gctgcctcct aacagacgct gcaaatgccg   16260
ggtctgtttc ttcacaggtt tgggcctgac acccagcact tggtcctgaa tgagaactgt   16320
gcctcagttc acaaccttcg cagccacaag attcaaaccc agctcaacct catccacccg   16380
gacatcttcc ccctgctcac cagtttccgc tgtaaggtag tgtctcagac yggccccttg   16440
tcggcccagc tctcgtcccc tctctttctc tccatgaatg tgttttgtct ctttcagaag   16500 gagggccccca ccctcagtgt gcccatggtt cagggtgaat gcctcctcaa gtaccagctc   16560
cgtcccagga gggagtggca gaggtctgtg ccatcttgaa ctaatggaat cgtctcagtc   16620
gagttgggaa acatttctgt aaatagccac atagtaaatg ttccaggagg ctctccagac   16680
catatggtct ctgttgtaac tattcaactc cgctttgagc acaaaagaaa cacggacaat   16740
aagctaatga atgggcttgg ctgtgtgcca gcgtgaattt atttagaaaa gcagcctact   16800
ccaggctggg ttgaggtggg cggattgggg ccagtagttc tccttttcca aaattgcctt   16860
gcatgggaat agcagtgata gagctcgtgt gtttcacagt atagaaaata ggaaatgtgt   16920
gatgaacaaa gtcacccata atcctgttgc ccagagataa tgattgataa cattttgtgt   16980
```

-continued

```
ttcttgattt gtgtatgtgg gtttatattg tcagtcttt cctgtatcac taaacagtct    17040
taagtaacaa gatttttatt ggtattccaa atagggatgt ttactcattt gggatgtttc    17100
caattttttg ttgttttaa tgaatgaaac aataaatgtc ttatatataa atctttgatg    17160
ggaactctgt tcccttcaag tcattcctaa atgtgggatt actggcccag agtgtgagac    17220
ttgttaaggt acttgataaa tgtaagatgc catcttgaaa gcctcttcca gtacaatcca    17280
accaggaaag tgaacagcct tactgcccca catctttatt ttaattaatt aatttattta    17340
ttttatttat ttatttattt ttttgagacg gagtttcact cttgttgccc aggctggagt    17400
gcaatggcgt gatctcagct cactgcaacc tccgcctccc gggttcaagc atttctcctg    17460
ccccagcctc ccgaatagct ggaattacag gcgcctgcta ccacgcccgg ctaattttt    17520 gtaattttag cagagacggg tttcaccatg ttggcaggct ggtctcgaac tcctgacctc    17580
aggtgatcca cccacctcag cctcccaaag tgttgggatt acaggcgtga gccgtgcccg    17640
gcctgtttta atttttaagg atctgaacct tgattttaag tttcctgccc actccacagt    17700
atttgtatta gaatagagca tgtgctggat tatgactgga tgctgtgtgc tgttgaggtt    17760
gggtagttgg ggccctttaa gagactatac tagcaagact cgggcccaca ggcaacatca    17820
cggggttgaa gaacctggtg tccctttgtt ggcatctgcg caggctctta acacacagca    17880
gcgatacaca gccctagccg acattcagat ttaccttgtg cttgtgaaaa atattgcaca    17940
gggcctgccc tagacctagt gaattagaat cttgagagtt aggcttggga ctcacaagct    18000
cccagatgat tttaatgctc agcgaggttg aagagccgcc tgtccaagga gttgccactc    18060
cgtgtgatct ggggcttgct aggaaagtgg gatctcaggc ctcactgcag agctgccgaa    18120
ctggcttctg cgttttgcca aggttcctgg gtgtgaacat gagtttcaga gtcactcctc    18180
tagggcccct gcttctcagc tcggaccatt gaccctcag aggacatttg caacatctg    18240 gaaacgttct tggttgtcac agcctaggag gtgggtagtg gtgctgctag tgggtagagg    18300 tcagggtac tgcaccagga cagcagcact ggccacagaa aaaaactgtc ttgccctgag    18360
catcagtagt tccccgttga ctggccctga ggcagagcga tgcagcatcc aaaaggcggt    18420
ggagcagacc tgccccagat cctagtcact taaccttcag tgttgatctg aaggaacttc    18480
ctgcagattg tccccctgaa tttattctgg acatccccaa tggggtctgc tgaggccata    18540
taccctgtcc gtcacctgag atgcttctct ctctyccctgc agggatgcca ttattacttg    18600
caatcctgag gaattcatag ttgaggcgct gcagcttccc aacttccagc agagcgtgca    18660
ggagtacagg aggagtgcgc aggacggccc agccccagca ggtgagtggg agcccacaga    18720
gcagcctttc tttcctgggc tctgcccctg ctgctgtttt cctagcatta agtgagtgc    18780 tggtggggcg cattctaacc tggcttttca gtctaatcca gggcttctct actcagctct    18840
acattagaat tatagtcatt ggaggagggg gctttgggga gtttaagaat cccaattcct    18900
ggctgggcgc ggtggctcac acctgtaatc ccagcacttc gggaggccga ggcaggtgga    18960
tcgcgaggtc gggagatcga gaccatcctg gctaacatga tgaaacccg tctctactaa    19020 aaatacaaaa attagctggg cgtggcgcg ggcgcctgta gtcccagcta ctcgggagac    19080
tgaggcagga gaatggcgag aacccgggag gcggagcttg cagtgagcca aggtcgtgcc    19140
actgcgctcc agcctggacg acagagtgag actccgtctc aaaaaaaaaa atcccaattc    19200
ctgtgcccca tcccacccaa tcagagcatt tggcgatggc acccaggcat tcttggcaag    19260
gcacgcactg agtgaaacgt tttagtgaac acctgtggaa agagctctga gcagggactt    19320
ggctggcaga gatctagtcc tggctttgcg gatgcaaatc catggaggat cttggccacg    19380
```

```
tcactcaact gaggctgagg gccgggcaca ggctttggaa ccatcgggtc tccctggatt     19440
tgaatcctga ccctgcctct taccatcttc actggagacc tgggcgtctg agcctgtttc     19500 cccccttggga agcagagcat ttcctacctg gtagggctgg gaggatgcga ccgaagtgca     19560
tggtcttgca gtgagagctg gatgcaaggc acacactgtt ctcttgaaat aaatgacagt     19620
tcccagcata agaaatgtc attttttaaa tgtaaaagaa ttacagcaat tcttttgaag      19680
aaaggactgg agaatttatt tgttcttctt agccttttgg tgacagatag cctgtgggtc     19740
ccacactggt gcgaagtcct ttgtttcaga gcggttgcca ggggcctgcc agtccccctc     19800
ctgggaagct ggatagaact atgttgctta cccatctgtc ttagtctgtg ttttgttatt     19860
ataaaagaat atgtgagact gggtaattta tcaagaaaag aggtgtattt agttcacggt     19920
tctgcgggct gagaattgaa ggtcacggcc ctagcttcca gtgaaggctt ccatgctgca     19980
tcataacgtg gcagaggagc gcaagtagga agtggacgct tgtgaagacg ggataacctg     20040
agctgcactc tggctttata caaccccccc tctcctggga acaaatccat tcccttgaga     20100
agtaatgcag tctcctgaga gccagtactt actactgcag ctccaagcca ctcaggaggg     20160
tccgtccctg tagcccaaac gccttccact aggccccgcc tccaaaaacc gccatactag     20220
ggagcacgtt tccacatgag gtctggggac aaaccaatga cactcaaacc attgcacctt     20280
ctcatggctg catgctggct cacttttgac ccaaaggaat ggattgtttc acatggattt     20340
tttcacagag aaaagaagtc agtacccaga aatcatcttc cttggaacag gtctgccat      20400 cccgatgaag attcgaaatg tcagtgccac acttgtcaac ataaggtatg ctgctttccc     20460
aggaagcatc cttccatcaa gggcaygttt acttttttaaa caaaagtcct gctgtactca     20520
ccagtcgatt tgaaatgcgg tatcaagccc tgtcacttgt catgtcgact ggagtgtcca     20580
ggagaggagc gtggccttac tgcatttat agcctcagta gcaaacttta ccctgggaat      20640
caccaaaatt catcccatga tgtctttttaa taaacagctg attttactgt gggcagtaca    20700
cctagctaag aaattagctc ctttaatttt tacattaatc ctatgaagtg gtgaataact     20760
acccattttg ttgatgagtg acctgatatt cagagaggtg acttgctatg gttcctacag     20820
ctggtaagtg gggcatctga agtttgagcg gggacttggg gtcttgattg ctacatggta     20880
ttgtccccca gccatttgtt ggtagtatgt taaaaagctt tagggttttg cacatttgtg     20940
ttcagaacct ttattggatt cccccttgaca tgtttttttag ttgattctct tgggtttgcc    21000
tggggtcatc agcagagaga ttagtcaaat gcgttgtgac atgtacacgt tatctctaca    21060
gatagtatgt gaagaaaata agattgtgaa ttaccaggtt tgttttaaat tttgctctgc    21120
catcttacat gctagtggtg gatgataaac aaccaaatag tgcattaaat atatacagca    21180
gtgacgagat gtgccctgac atcagaaata tacaatctgg ggtgtgtttc tctgtggatg    21240
aggacatgca ataaagcagc ttggagtgag ccggcctctc ccgggggctg agatcctggg    21300
ggaagaaggg cttttttgagt ttgacctgac accctgcgag cagcttttga accagctgaa    21360
gctaatggga aggtgctatt gccaccttgc ctccgcctcc cgactccttt tcccccagga    21420
aggtaatgtc ttagcaccgg ggcttctctc tgcaaaatgg gtgcagccct ctcagtgttc    21480
gtggctcctc ccagagaatg aaggaggcca gagcgggtca gcactctctc tgccttggag    21540
cagagcttct gaaatggact gcacagcaga atagcccaag aagtttgtca gaatccagac    21600
ttccagagcc ctgcctaaaa ccaagtcaga aaccccgagt gacacctggg agtctgcgtt    21660
aactggctcc ctgaatgaag cacctgcagc ccgccctgca ccaggtgtct ttgaggacat    21720
```

```
gagctgagga aaccccgacc acttgcaaag ggggaaaagt ccgatggcag ctggacctag    21780
aaagagtctc atatggccca gtgcctgtcc tggtattttc aacagaggct gtggccacag    21840
tcaatctgca tggtcagatt cattgttagg actaaatgct ttaagcctcc tataaacttt    21900
tttttttttt ttttgatgcc cagcctttgt gtaagtctac ttgaaagggt ttcagggttc    21960
catggatact tctttgctat aaagaggatg acacatgtaa aatcacctttt atggttaaat   22020 taattggctt ttatattagc tcctcaaagc aaagcaggag agacagaaat ttctgcagtt    22080
gcttcttggt cctgtccaaa gcagacatca gcctctgaac catcagcagt cttcctagtg    22140
gcagtgactc tcttcctctt ctcttctgca gccccgacag gtctctgcta ctggactgtg    22200
gtgagggcac rtttgggcag ctgtgccgtc attacggaga ccaggtggac agggtcctgg    22260
gcaccctggc tgctgtgttt gtgtcccacc tgcacgcaga tcaccacacg gtgagtgttg    22320
ggctggacca caaagctgga gcctggagga ggcactgcca cgttgagttg gccctttggc    22380
tgcgtctttt cctccgcttc caaacttgcc cagagctttt gttactcatc tctggctagg    22440
aaatggtttt ttgcaaaact caacatagtc cttctgcgcc acaagaatgt cttctcttcc    22500
tgttcagttc ctttcctgca gcaggacagg tttgagttta cccagccttc cttgagtctt    22560
gaatctcaca cggcctgctc agcggaagct ttgaccggat gcaggaggtg tggctatgag    22620
accctcacct tggtctcctg gggtgccggg ccctgggccg ttgccctctt cccagcacgg    22680
gtcgtgtcgc tttctgcctg tgacatttca gggccatggc gcaggggct cggcctgtgc     22740 cacccccact gcggctgtgt tagaggctgg tgggtgacgt cgggctggca actcctgcaa    22800
gagagagggc tgcagaccct aacccggagg ggatggccct ggggcctggc tgacgcatgt    22860
ctcctgtttc cttgccaggg cttgccaagt atcttgctgc agagagaacg cgccttggta    22920
agtgtggcac ttgatgggcg ttctgagttt cagcggttta cacatcatcc gccatgcctc    22980
ttggcactcc agtttttatt gagatgttct gtcgtcgagt cggcacttgc attttttgtt    23040
ccaggcatct ttgggaaagc cgcttcaccc tttgctggtg gttgcccca accagctcaa     23100 agcctggctc cagcagtacc acaaccagtg ccaggaggtc ctgcaccaca tcaggtgagc    23160
atccagggca gcctggcccg stgggctgtt gcttgctgcc gtctccttca gaagctcaag    23220
gtggacactg gggtagttac caatatcccc cagcagcctt gcccttgaca tggtcccaga    23280
tggcagaagc aggggagaag tgcattggct gaaggacaga aaccattaga tagttcccat    23340
gtaatgctta ttttcttaga agcatttctt cccagtcctc atttgagttc tgagctgctt    23400
tctaaacttc gagcagcttt tcttgatgag acagttccag agccaagcac ccaaatagtg    23460
gctagcacag agaatgtcca tagcaggtgt gtggctagct ggcaggtggc accatcctca    23520
ccccaagggg aaggagtccc ctctgctgga gccatccgtg gcccgtgctg cctgagccgg    23580
aggcagcatt cacctgctgg gtttctccca gtggcctaga ggctttggtt tggctctta    23640 tatttgactg ctgtttcctc atcatagtga ctatgattta actcatgttt tctcctaaga    23700
atgattttgg ggttctccag ccaaagactt aaactttggt tccagatgtc caagaaacgt    23760
ttattatcat tttaaatgtt ttgtcttttt acagtatgat tcctgccaaa tgccttcagg    23820
aaggggctga gatctccagt cctgcagtgg aaagattgat cagttcgctg ttgcgaacrt    23880
gtgatttgga agaggtaagg ggcacagccg caggcatcat gggggcgagg tggggagcag    23940
agctgcagag ccctccagcc ccaccctttc agtttcagac ctgtctggtg cggcactgca    24000
agcatgcgtt tggctgtgcg ctggtgcaca cctctggctg gaaagtggtc tattccgggg    24060
acaccatgcc ctgcgaggct ctggtccgga tgggtgagta gaggaagaag caagccaccc    24120
```

-continued

```
tgaggttgct ctggggtttg tgtagctgga ggtgaatgca ggtgggcttg cagggaaacg    24180
tcagcagagg caggagactc aggtccccac cctcagagtc tctggttgtc atcctagtag    24240
gcagacccag ggccagggga gctgagtgtt gagaccagga acagcacgt gactgaggcc     24300 tgtgtgccgc tctcgcagag aactctgccc tgatccttgt gctgcttctc cagggaaaga    24360
tgccaccctc ctgatacatg aagccaccct ggaagatggt ttggaagagg aagcagtgga    24420
aaagacacac aggtagcaaa ggccggtcag tccttgtcgc ccacatcctc tccctccccc    24480
actacgtgac actgagcagc cgtcgtttgt ctccactgat gtggggctgc cctgcttcct    24540
atcaagggct atgggggctt ccttgacctg tggcagtgct cacaggctct tggcctttat    24600
ttttgcagaa ttttctaagc aagattctag agtgaggcac agttttttga aagcatctag    24660
aaatcggctg aataaactat aagccatgtc agggaattgc caggggaagg cggggctgg     24720 gggactgaat ttttggctgc taatttcaac gaaagagtgc attacccag gtgggccctg     24780 tggtttctct tgggtgccct catggacaga tttggcagcc agcacagagg gtgggcttca    24840
tccaggggtg tgtgcgaagg ctctggcccct caggggagat tgtgctggct acggaggtgc   24900
ccgttaagaa aacccaccag cttccccggg tgccctggca gttgatggcc agggtctgtg    24960
ccactgtctg ctttgcagtc ttgcagttga gttcagcttc agtctgctct gtccttcacc    25020
tgcagcacaa cgtcccaagc catcagcgtg gggatgcgga tgaacgcgga gttcattatg    25080
ctgaaccact tcagccagcg ctatgccaag gtccccctct tcagcccccaa cttcagcgag    25140 aaagtgggag ttgcctttga ccacatgaag gtctgtatgt cacacggaca gcacagggcg    25200 gggacgggc agggagacag gactctacac actgagtagg acggtcagct ggagtttgct    25260
ttcttatttg gggccaccgt gggaaaaggt tatctaccca tcactaacca ggtcgaacca    25320
ccctgggttt gctggtgaga cccacctcct gcaggggcca actagtcttc agtctcagtt    25380
cactggaaat ttctgagaat ccttttaggc ctggactgct cacacagtca tggcatttga    25440
gcctcagcac agacctgtga cacaggtggt tgcctcttgt gagtgggaaa gccaggcctg    25500
acccttggcc ttccggaatg aagggggcaga gccggagcca ggcctcgttt ttcaggagct   25560
tgattttgag agcatctgga ctgctctccc ttccctctcc ggaggccctt agccaggcct    25620
ggggagcctc tgccccttta gagggttccc tccatgccat tcttttttcc atttcagctg    25680
tggcctgttg gcttgtgcca aggaaggggc gttggcgctg ctgtgtgagc acatgactgc    25740
atcccttcca gctcctgtcc cccaccccctg cccctctgag acatgtcctt gtcttctatt   25800
gtgtcttcta ggtctgcttt ggagactttc caacaatgcc caagctgatt cccccactga    25860
aagccctgtt tgctggcgac atcgaggaga tggaggagcg cagggagaag cgggagctgc    25920
ggcaggtgcg ggcggccctc ctgtccaggg agctggcagg cggcctggag gatggggagc    25980
ctcagcagaa gcgggcccac acagaggagc cacaggccaa gaaggtcaga gcccagtgaa    26040
gatctgggag accctgaact cagaaggctg tgtgtcttct gccccacgca cgcacccgta    26100
tctgccctcc ttgctggtag aagctgaaga gcacggtccc ccaggaggca gctcaggata    26160
ggtggtatgg agctgtgccg aggcttgggc tcccacataa gcactagtct atagatgcct    26220
cttaggactg gtgcctggca cagccgcggg ccaggaggct gccacacgga agcaagcaga    26280
tgaactaatt tcatttcaag gcagttttta aagaagtctt ggaaacagac ggcggcacct    26340
ttcctctaat ccagcaaagt gattcccctgc acaccagaga caagcagagt aacaggatca    26400
gtgggtctaa gtgtccgaga cttaacgaaa atagtatttc agctgcaata aagattgagt    26460
```

```
ttgcaattgt gagttctttt gcttcctcct gctgctgcta cagagcaggg tctgctgtgc    26520
accaccttgg agaaggctct ctgtgctgta gtgtggcagc tgcctggtac ccgggtggct    26580
tggaagaagt cagctcccgt cgtagtgagc acctctggaa cctgtcctca gagagccacc    26640
cttattcgcc aagtctttt gaca                                             26664

<210> SEQ ID NO 29
<211> LENGTH: 31
<212> TYPE: DNA
<213> ORGANISM: Homo sapiens

<400> SEQUENCE: 29
caggaattca gcacatactc attgttcagn n                                    31

<210> SEQ ID NO 30
<211> LENGTH: 21
<212> TYPE: DNA
<213> ORGANISM: Homo sapiens

<400> SEQUENCE: 30
caggaattca gcacatactc a                                               21

<210> SEQ ID NO 31
<211> LENGTH: 22
<212> TYPE: DNA
<213> ORGANISM: Homo sapiens

<400> SEQUENCE: 31
ttcagcacat actcattgtt ca                                              22

<210> SEQ ID NO 32
<211> LENGTH: 19
<212> TYPE: DNA
<213> ORGANISM: Homo sapiens

<400> SEQUENCE: 32
tgaacgcctt ctccacagt                                                  19

<210> SEQ ID NO 33
<211> LENGTH: 17
<212> TYPE: DNA
<213> ORGANISM: Homo sapiens

<400> SEQUENCE: 33
gtacccgctg ccaccac                                                    17

<210> SEQ ID NO 34
<211> LENGTH: 33
<212> TYPE: DNA
<213> ORGANISM: Homo sapiens

<400> SEQUENCE: 34
gctaggatcc gccaccatgt gggcgctttg ctc                                  33

<210> SEQ ID NO 35
<211> LENGTH: 29
<212> TYPE: DNA
<213> ORGANISM: Homo sapiens

<400> SEQUENCE: 35
gctactcgag tcactgggct ctgaccttc                                       29
```

```
<210> SEQ ID NO 36
<211> LENGTH: 17
<212> TYPE: DNA
<213> ORGANISM: Homo sapiens

<400> SEQUENCE: 36
gtaaaacgac ggccagt                                                    17

<210> SEQ ID NO 37
<211> LENGTH: 19
<212> TYPE: DNA
<213> ORGANISM: Homo sapiens

<400> SEQUENCE: 37
ggaaacagct atgaccatg                                                  19

<210> SEQ ID NO 38
<211> LENGTH: 17
<212> TYPE: DNA
<213> ORGANISM: Homo sapiens

<400> SEQUENCE: 38
tgcgcacgcg agagaag                                                    17

<210> SEQ ID NO 39
<211> LENGTH: 17
<212> TYPE: DNA
<213> ORGANISM: Homo sapiens

<400> SEQUENCE: 39
cgcttctctc gcgtgcg                                                    17

<210> SEQ ID NO 40
<211> LENGTH: 18
<212> TYPE: DNA
<213> ORGANISM: Homo sapiens

<400> SEQUENCE: 40
tctaatgttg ggggctta                                                   18

<210> SEQ ID NO 41
<211> LENGTH: 18
<212> TYPE: DNA
<213> ORGANISM: Homo sapiens

<400> SEQUENCE: 41
taagccccca acattaga                                                   18

<210> SEQ ID NO 42
<211> LENGTH: 18
<212> TYPE: DNA
<213> ORGANISM: Homo sapiens

<400> SEQUENCE: 42
tgaaaatgag ccacacct                                                   18

<210> SEQ ID NO 43
<211> LENGTH: 18
<212> TYPE: DNA
<213> ORGANISM: Homo sapiens

<400> SEQUENCE: 43
aggtgtggct cattttca                                                   18
```

-continued

```
<210> SEQ ID NO 44
<211> LENGTH: 18
<212> TYPE: DNA
<213> ORGANISM: Homo sapiens

<400> SEQUENCE: 44
cattcaaccc atctgtga                                                 18

<210> SEQ ID NO 45
<211> LENGTH: 18
<212> TYPE: DNA
<213> ORGANISM: Homo sapiens

<400> SEQUENCE: 45
tcacagatgg gttgaatg                                                 18

<210> SEQ ID NO 46
<211> LENGTH: 18
<212> TYPE: DNA
<213> ORGANISM: Homo sapiens

<400> SEQUENCE: 46
tgaatgcctc ctcaagta                                                 18

<210> SEQ ID NO 47
<211> LENGTH: 18
<212> TYPE: DNA
<213> ORGANISM: Homo sapiens

<400> SEQUENCE: 47
tacttgagga ggcattca                                                 18

<210> SEQ ID NO 48
<211> LENGTH: 18
<212> TYPE: DNA
<213> ORGANISM: Homo sapiens

<400> SEQUENCE: 48
gctactggac tgtggtga                                                 18

<210> SEQ ID NO 49
<211> LENGTH: 18
<212> TYPE: DNA
<213> ORGANISM: Homo sapiens

<400> SEQUENCE: 49
tcaccacagt ccagtagc                                                 18

<210> SEQ ID NO 50
<211> LENGTH: 19
<212> TYPE: DNA
<213> ORGANISM: Homo sapiens

<400> SEQUENCE: 50
tggaagagtt tcagacctg                                                19

<210> SEQ ID NO 51
<211> LENGTH: 19
<212> TYPE: DNA
<213> ORGANISM: Homo sapiens

<400> SEQUENCE: 51
caggtctgaa actcttcca                                                19
```

<210> SEQ ID NO 52
<211> LENGTH: 17
<212> TYPE: DNA
<213> ORGANISM: Homo sapiens

<400> SEQUENCE: 52
cgcagggacg caccata                                                17

<210> SEQ ID NO 53
<211> LENGTH: 18
<212> TYPE: DNA
<213> ORGANISM: Homo sapiens

<400> SEQUENCE: 53
ggttgaactc ggagaaga                                               18

<210> SEQ ID NO 54
<211> LENGTH: 19
<212> TYPE: DNA
<213> ORGANISM: Homo sapiens

<400> SEQUENCE: 54
caactggaaa aatacctcg                                              19

<210> SEQ ID NO 55
<211> LENGTH: 17
<212> TYPE: DNA
<213> ORGANISM: Homo sapiens

<400> SEQUENCE: 55
gcagagtcca gaaaggc                                                17

<210> SEQ ID NO 56
<211> LENGTH: 19
<212> TYPE: DNA
<213> ORGANISM: Homo sapiens

<400> SEQUENCE: 56
agaggaaact tcttggtgc                                              19

<210> SEQ ID NO 57
<211> LENGTH: 18
<212> TYPE: DNA
<213> ORGANISM: Homo sapiens

<400> SEQUENCE: 57
accaaggaaa ggcagatg                                               18

<210> SEQ ID NO 58
<211> LENGTH: 18
<212> TYPE: DNA
<213> ORGANISM: Homo sapiens

<400> SEQUENCE: 58
gtcaacataa gccccgac                                               18

<210> SEQ ID NO 59
<211> LENGTH: 18
<212> TYPE: DNA
<213> ORGANISM: Homo sapiens

<400> SEQUENCE: 59
ggctgctgtg tttgtgtc                                            18

<210> SEQ ID NO 60
<211> LENGTH: 17
<212> TYPE: DNA
<213> ORGANISM: Homo sapiens

<400> SEQUENCE: 60
gaaggcattt ggcagga                                             17

<210> SEQ ID NO 61
<211> LENGTH: 18
<212> TYPE: DNA
<213> ORGANISM: Homo sapiens

<400> SEQUENCE: 61
tatgattcct gccaaatg                                            18

<210> SEQ ID NO 62
<211> LENGTH: 17
<212> TYPE: DNA
<213> ORGANISM: Homo sapiens

<400> SEQUENCE: 62
tccagccaga ggtgtgc                                             17

<210> SEQ ID NO 63
<211> LENGTH: 17
<212> TYPE: DNA
<213> ORGANISM: Homo sapiens

<400> SEQUENCE: 63
tgcgaggctc tggtccg                                             17

<210> SEQ ID NO 64
<211> LENGTH: 18
<212> TYPE: DNA
<213> ORGANISM: Homo sapiens

<400> SEQUENCE: 64
gggcattgtt ggaaagtc                                            18

<210> SEQ ID NO 65
<211> LENGTH: 17
<212> TYPE: DNA
<213> ORGANISM: Homo sapiens

<400> SEQUENCE: 65
tgtttgctgg cgacatc                                             17

<210> SEQ ID NO 66
<211> LENGTH: 31
<212> TYPE: DNA
<213> ORGANISM: Homo sapiens

<400> SEQUENCE: 66
caggaattca gcacatactc attgttcagn n                             31

<210> SEQ ID NO 67
<211> LENGTH: 21
<212> TYPE: DNA
<213> ORGANISM: Homo sapiens

<400> SEQUENCE: 67

```
caggaattca gcacatactc a                                      21

<210> SEQ ID NO 68
<211> LENGTH: 22
<212> TYPE: DNA
<213> ORGANISM: Homo sapiens

<400> SEQUENCE: 68
ttcagcacat actcattgtt ca                                     22

<210> SEQ ID NO 69
<211> LENGTH: 19
<212> TYPE: DNA
<213> ORGANISM: Homo sapiens

<400> SEQUENCE: 69
cagaacacat ttgggaagc                                         19

<210> SEQ ID NO 70
<211> LENGTH: 18
<212> TYPE: DNA
<213> ORGANISM: Homo sapiens

<400> SEQUENCE: 70
gatgttgtcc aagcgagc                                          18

<210> SEQ ID NO 71
<211> LENGTH: 17
<212> TYPE: DNA
<213> ORGANISM: Homo sapiens

<400> SEQUENCE: 71
tgacacacag cacctga                                           17

<210> SEQ ID NO 72
<211> LENGTH: 17
<212> TYPE: DNA
<213> ORGANISM: Homo sapiens

<400> SEQUENCE: 72
gaagatgtca gggtgga                                           17

<210> SEQ ID NO 73
<211> LENGTH: 18
<212> TYPE: DNA
<213> ORGANISM: Homo sapiens

<400> SEQUENCE: 73
caggcatacc actacaga                                          18

<210> SEQ ID NO 74
<211> LENGTH: 20
<212> TYPE: DNA
<213> ORGANISM: Homo sapiens

<400> SEQUENCE: 74
tatcaacttc taggcaagtg                                        20

<210> SEQ ID NO 75
<211> LENGTH: 19
<212> TYPE: DNA
<213> ORGANISM: Homo sapiens
```

```
<400> SEQUENCE: 75
gcaccatgtc gcagggttc                                               19

<210> SEQ ID NO 76
<211> LENGTH: 19
<212> TYPE: DNA
<213> ORGANISM: Homo sapiens

<400> SEQUENCE: 76
gaaccctgcg acatggtgc                                               19

<210> SEQ ID NO 77
<211> LENGTH: 19
<212> TYPE: DNA
<213> ORGANISM: Homo sapiens

<400> SEQUENCE: 77
tcgcagggtt cggctcgtc                                               19

<210> SEQ ID NO 78
<211> LENGTH: 19
<212> TYPE: DNA
<213> ORGANISM: Homo sapiens

<400> SEQUENCE: 78
aaccctgcga catggtgcg                                               19

<210> SEQ ID NO 79
<211> LENGTH: 19
<212> TYPE: DNA
<213> ORGANISM: Homo sapiens

<400> SEQUENCE: 79
aaagacccac tgcgacacc                                               19

<210> SEQ ID NO 80
<211> LENGTH: 19
<212> TYPE: DNA
<213> ORGANISM: Homo sapiens

<400> SEQUENCE: 80
gcaggtgtcg cagtgggtc                                               19

<210> SEQ ID NO 81
<211> LENGTH: 20
<212> TYPE: DNA
<213> ORGANISM: Homo sapiens

<400> SEQUENCE: 81
ccgaacaccg tgtacctgca                                              20

<210> SEQ ID NO 82
<211> LENGTH: 19
<212> TYPE: DNA
<213> ORGANISM: Homo sapiens

<400> SEQUENCE: 82
caggtacacg gtgttcggg                                               19

<210> SEQ ID NO 83
<211> LENGTH: 21
<212> TYPE: DNA
<213> ORGANISM: Homo sapiens
```

```
<400> SEQUENCE: 83
gtcttctcgg aatacaacag g                                           21

<210> SEQ ID NO 84
<211> LENGTH: 20
<212> TYPE: DNA
<213> ORGANISM: Homo sapiens

<400> SEQUENCE: 84
ctgttgtatt ccgagaagac                                             20

<210> SEQ ID NO 85
<211> LENGTH: 20
<212> TYPE: DNA
<213> ORGANISM: Homo sapiens

<400> SEQUENCE: 85
aaggcgtcca acgacttatg                                             20

<210> SEQ ID NO 86
<211> LENGTH: 20
<212> TYPE: DNA
<213> ORGANISM: Homo sapiens

<400> SEQUENCE: 86
agtcgttgga cgccttctcc                                             20

<210> SEQ ID NO 87
<211> LENGTH: 20
<212> TYPE: DNA
<213> ORGANISM: Homo sapiens

<400> SEQUENCE: 87
tccgagtcag aaagatgttg                                             20

<210> SEQ ID NO 88
<211> LENGTH: 17
<212> TYPE: DNA
<213> ORGANISM: Homo sapiens

<400> SEQUENCE: 88
gccttgtcag cctggtg                                                17

<210> SEQ ID NO 89
<211> LENGTH: 17
<212> TYPE: DNA
<213> ORGANISM: Homo sapiens

<400> SEQUENCE: 89
aggaagtgag cagagcg                                                17

<210> SEQ ID NO 90
<211> LENGTH: 33
<212> TYPE: DNA
<213> ORGANISM: Homo sapiens

<400> SEQUENCE: 90
gctaaagctt gccaccatgt gggcgctccg ctc                              33

<210> SEQ ID NO 91
<211> LENGTH: 27
<212> TYPE: DNA
```

```
<213> ORGANISM: Homo sapiens

<400> SEQUENCE: 91
gctactcgag tcacactcgc gctccta                                        27

<210> SEQ ID NO 92
<211> LENGTH: 16
<212> TYPE: DNA
<213> ORGANISM: Homo sapiens

<400> SEQUENCE: 92
gccttctccg cagtta                                                    16

<210> SEQ ID NO 93
<211> LENGTH: 21
<212> TYPE: DNA
<213> ORGANISM: Homo sapiens

<400> SEQUENCE: 93
ccgcctgaga cgctctagta t                                              21

<210> SEQ ID NO 94
<211> LENGTH: 19
<212> TYPE: DNA
<213> ORGANISM: Homo sapiens

<400> SEQUENCE: 94
gctccgaaag tgctgacag                                                 19

<210> SEQ ID NO 95
<211> LENGTH: 39
<212> TYPE: DNA
<213> ORGANISM: Homo sapiens

<400> SEQUENCE: 95
gttttcccag tcacgacgtt tctattggat gagcagcct                           39

<210> SEQ ID NO 96
<211> LENGTH: 38
<212> TYPE: DNA
<213> ORGANISM: Homo sapiens

<400> SEQUENCE: 96
aggaaacagc tatgaccatg cctgcgatat ggtgcgtc                            38

<210> SEQ ID NO 97
<211> LENGTH: 37
<212> TYPE: DNA
<213> ORGANISM: Homo sapiens

<400> SEQUENCE: 97
gttttcccag tcacgacgct cagttttggt ggagacg                             37

<210> SEQ ID NO 98
<211> LENGTH: 37
<212> TYPE: DNA
<213> ORGANISM: Homo sapiens

<400> SEQUENCE: 98
aggaaacagc tatgaccatg tgccccgatg ctcagag                             37

<210> SEQ ID NO 99
<211> LENGTH: 22
```

<212> TYPE: DNA
<213> ORGANISM: Homo sapiens

<400> SEQUENCE: 99
aatggtgtca gagagtttac ag                                              22

<210> SEQ ID NO 100
<211> LENGTH: 19
<212> TYPE: DNA
<213> ORGANISM: Homo sapiens

<400> SEQUENCE: 100
gctatttggg aggctgagg                                                  19

<210> SEQ ID NO 101
<211> LENGTH: 40
<212> TYPE: DNA
<213> ORGANISM: Homo sapiens

<400> SEQUENCE: 101
gttttcccag tcacgacgaa tggtgtcaga gagtttacag                           40

<210> SEQ ID NO 102
<211> LENGTH: 41
<212> TYPE: DNA
<213> ORGANISM: Homo sapiens

<400> SEQUENCE: 102
aggaaacagc tatgaccatg aacaaggacc acttttgcta t                         41

<210> SEQ ID NO 103
<211> LENGTH: 40
<212> TYPE: DNA
<213> ORGANISM: Homo sapiens

<400> SEQUENCE: 103
gttttcccag tcacgacgtt tatagcaaaa gtggtccttg                           40

<210> SEQ ID NO 104
<211> LENGTH: 38
<212> TYPE: DNA
<213> ORGANISM: Homo sapiens

<400> SEQUENCE: 104
aggaaacagc tatgaccatg agacttccca ccagcctc                             38

<210> SEQ ID NO 105
<211> LENGTH: 19
<212> TYPE: DNA
<213> ORGANISM: Homo sapiens

<400> SEQUENCE: 105
ccttgctgct tcaccctag                                                  19

<210> SEQ ID NO 106
<211> LENGTH: 21
<212> TYPE: DNA
<213> ORGANISM: Homo sapiens

<400> SEQUENCE: 106
tgctttatat gtgctgctac g                                               21

<210> SEQ ID NO 107

```
<211> LENGTH: 39
<212> TYPE: DNA
<213> ORGANISM: Homo sapiens

<400> SEQUENCE: 107
gttttcccag tcacgacgca tcttccctgg ttgtacttc                               39

<210> SEQ ID NO 108
<211> LENGTH: 39
<212> TYPE: DNA
<213> ORGANISM: Homo sapiens

<400> SEQUENCE: 108
aggaaacagc tatgaccatc tggagggcag aagactgat                               39

<210> SEQ ID NO 109
<211> LENGTH: 23
<212> TYPE: DNA
<213> ORGANISM: Homo sapiens

<400> SEQUENCE: 109
ctacatttgt tcaaccataa ctg                                                23

<210> SEQ ID NO 110
<211> LENGTH: 23
<212> TYPE: DNA
<213> ORGANISM: Homo sapiens

<400> SEQUENCE: 110
gattttgagg tttgatgttg atg                                                23

<210> SEQ ID NO 111
<211> LENGTH: 39
<212> TYPE: DNA
<213> ORGANISM: Homo sapiens

<400> SEQUENCE: 111
gttttcccag tcacgacgca tttgttcaac cataactgc                               39

<210> SEQ ID NO 112
<211> LENGTH: 39
<212> TYPE: DNA
<213> ORGANISM: Homo sapiens

<400> SEQUENCE: 112
aggaaacagc tatgaccata tttgagaggt cagggcata                               39

<210> SEQ ID NO 113
<211> LENGTH: 21
<212> TYPE: DNA
<213> ORGANISM: Homo sapiens

<400> SEQUENCE: 113
tcgtgtcaga ttcccaccat a                                                  21

<210> SEQ ID NO 114
<211> LENGTH: 21
<212> TYPE: DNA
<213> ORGANISM: Homo sapiens

<400> SEQUENCE: 114
aggcataagt cagacatccg t                                                  21
```

```
<210> SEQ ID NO 115
<211> LENGTH: 40
<212> TYPE: DNA
<213> ORGANISM: Homo sapiens

<400> SEQUENCE: 115
gttttcccag tcacgacggt tactcttccc acacatcttc                              40

<210> SEQ ID NO 116
<211> LENGTH: 41
<212> TYPE: DNA
<213> ORGANISM: Homo sapiens

<400> SEQUENCE: 116
aggaaacagc tatgaccatc acagcaagtg ttcagtttct a                            41

<210> SEQ ID NO 117
<211> LENGTH: 21
<212> TYPE: DNA
<213> ORGANISM: Homo sapiens

<400> SEQUENCE: 117
cattcccatg tatgaacgtc t                                                  21

<210> SEQ ID NO 118
<211> LENGTH: 22
<212> TYPE: DNA
<213> ORGANISM: Homo sapiens

<400> SEQUENCE: 118
atagtaagcc caggaagaag ga                                                 22

<210> SEQ ID NO 119
<211> LENGTH: 39
<212> TYPE: DNA
<213> ORGANISM: Homo sapiens

<400> SEQUENCE: 119
gttttcccag tcacgacgca ttcccatgta tgaacgtct                               39

<210> SEQ ID NO 120
<211> LENGTH: 41
<212> TYPE: DNA
<213> ORGANISM: Homo sapiens

<400> SEQUENCE: 120
aggaaacagc tatgaccatc tacaagcatt acaaggcaga g                            41

<210> SEQ ID NO 121
<211> LENGTH: 22
<212> TYPE: DNA
<213> ORGANISM: Homo sapiens

<400> SEQUENCE: 121
agtgtcttca gcctttgtat tg                                                 22

<210> SEQ ID NO 122
<211> LENGTH: 23
<212> TYPE: DNA
<213> ORGANISM: Homo sapiens

<400> SEQUENCE: 122
atctgctatc tcttcttgtc tca                                                23
```

-continued

<210> SEQ ID NO 123
<211> LENGTH: 40
<212> TYPE: DNA
<213> ORGANISM: Homo sapiens

<400> SEQUENCE: 123
gttttcccag tcacgacgat cgggtcataa tcagtctgtg         40

<210> SEQ ID NO 124
<211> LENGTH: 42
<212> TYPE: DNA
<213> ORGANISM: Homo sapiens

<400> SEQUENCE: 124
aggaaacagc tatgaccata tctcttcttg tctcaggtaa ca      42

<210> SEQ ID NO 125
<211> LENGTH: 22
<212> TYPE: DNA
<213> ORGANISM: Homo sapiens

<400> SEQUENCE: 125
cttctgaaag caataaacgc at                            22

<210> SEQ ID NO 126
<211> LENGTH: 20
<212> TYPE: DNA
<213> ORGANISM: Homo sapiens

<400> SEQUENCE: 126
gatgtccaaa ctgttccacg                               20

<210> SEQ ID NO 127
<211> LENGTH: 40
<212> TYPE: DNA
<213> ORGANISM: Homo sapiens

<400> SEQUENCE: 127
gttttcccag tcacgacgta aaaccaacct tcttcattag         40

<210> SEQ ID NO 128
<211> LENGTH: 38
<212> TYPE: DNA
<213> ORGANISM: Homo sapiens

<400> SEQUENCE: 128
aggaaacagc tatgaccata gcaatgatgg gagcgatg           38

<210> SEQ ID NO 129
<211> LENGTH: 37
<212> TYPE: DNA
<213> ORGANISM: Homo sapiens

<400> SEQUENCE: 129
gttttcccag tcacgacggg cttctgggga ctcactg            37

<210> SEQ ID NO 130
<211> LENGTH: 41
<212> TYPE: DNA
<213> ORGANISM: Homo sapiens

<400> SEQUENCE: 130
aggaaacagc tatgaccatc cttcaaaagt ggtgtctgta g       41

```
<210> SEQ ID NO 131
<211> LENGTH: 22
<212> TYPE: DNA
<213> ORGANISM: Homo sapiens

<400> SEQUENCE: 131
gtatccacaa agagaccaga ag                                              22

<210> SEQ ID NO 132
<211> LENGTH: 23
<212> TYPE: DNA
<213> ORGANISM: Homo sapiens

<400> SEQUENCE: 132
caccaactac caacagtgac tta                                             23

<210> SEQ ID NO 133
<211> LENGTH: 41
<212> TYPE: DNA
<213> ORGANISM: Homo sapiens

<400> SEQUENCE: 133
gttttcccag tcacgacggc tcactggata ggatatgtca t                         41

<210> SEQ ID NO 134
<211> LENGTH: 39
<212> TYPE: DNA
<213> ORGANISM: Homo sapiens

<400> SEQUENCE: 134
aggaaacagc tatgaccatc cagaaacaca gctcttgcc                            39

<210> SEQ ID NO 135
<211> LENGTH: 20
<212> TYPE: DNA
<213> ORGANISM: Homo sapiens

<400> SEQUENCE: 135
gcttgccaga tacaggaatc                                                 20

<210> SEQ ID NO 136
<211> LENGTH: 20
<212> TYPE: DNA
<213> ORGANISM: Homo sapiens

<400> SEQUENCE: 136
acagaaagtt taggcaggtg                                                 20

<210> SEQ ID NO 137
<211> LENGTH: 37
<212> TYPE: DNA
<213> ORGANISM: Homo sapiens

<400> SEQUENCE: 137
gttttcccag tcacgacgac gataccctc cctggct                               37

<210> SEQ ID NO 138
<211> LENGTH: 39
<212> TYPE: DNA
<213> ORGANISM: Homo sapiens

<400> SEQUENCE: 138
```

| | |
|---|---|
| aggaaacagc tatgaccata cagaaagttt aggcaggtg | 39 |

<210> SEQ ID NO 139
<211> LENGTH: 20
<212> TYPE: DNA
<213> ORGANISM: Homo sapiens

<400> SEQUENCE: 139

| | |
|---|---|
| cctctcactc ttcccagcac | 20 |

<210> SEQ ID NO 140
<211> LENGTH: 22
<212> TYPE: DNA
<213> ORGANISM: Homo sapiens

<400> SEQUENCE: 140

| | |
|---|---|
| ggagtaggct gcttttctaa at | 22 |

<210> SEQ ID NO 141
<211> LENGTH: 40
<212> TYPE: DNA
<213> ORGANISM: Homo sapiens

<400> SEQUENCE: 141

| | |
|---|---|
| gttttcccag tcacgacgga acacctcatc ctcattacca | 40 |

<210> SEQ ID NO 142
<211> LENGTH: 41
<212> TYPE: DNA
<213> ORGANISM: Homo sapiens

<400> SEQUENCE: 142

| | |
|---|---|
| aggaaacagc tatgaccata agagacaaaa cacattcatg g | 41 |

<210> SEQ ID NO 143
<211> LENGTH: 39
<212> TYPE: DNA
<213> ORGANISM: Homo sapiens

<400> SEQUENCE: 143

| | |
|---|---|
| gttttcccag tcacgacggt ttccgctgta aggtagtgt | 39 |

<210> SEQ ID NO 144
<211> LENGTH: 42
<212> TYPE: DNA
<213> ORGANISM: Homo sapiens

<400> SEQUENCE: 144

| | |
|---|---|
| aggaaacagc tatgaccatc tggaacattt actatgtggc ta | 42 |

<210> SEQ ID NO 145
<211> LENGTH: 20
<212> TYPE: DNA
<213> ORGANISM: Homo sapiens

<400> SEQUENCE: 145

| | |
|---|---|
| tgctagtggg tagaggtcag | 20 |

<210> SEQ ID NO 146
<211> LENGTH: 21
<212> TYPE: DNA
<213> ORGANISM: Homo sapiens

<400> SEQUENCE: 146

```
actgaaagcc aggttagaat g                                              21

<210> SEQ ID NO 147
<211> LENGTH: 37
<212> TYPE: DNA
<213> ORGANISM: Homo sapiens

<400> SEQUENCE: 147
gttttcccag tcacgacgac cctgtccgtc acctgag                             37

<210> SEQ ID NO 148
<211> LENGTH: 38
<212> TYPE: DNA
<213> ORGANISM: Homo sapiens

<400> SEQUENCE: 148
aggaaacagc tatgaccatc ccaccagcac tccactta                            38

<210> SEQ ID NO 149
<211> LENGTH: 21
<212> TYPE: DNA
<213> ORGANISM: Homo sapiens

<400> SEQUENCE: 149
tgtgaagacg ggataacctg a                                              21

<210> SEQ ID NO 150
<211> LENGTH: 19
<212> TYPE: DNA
<213> ORGANISM: Homo sapiens

<400> SEQUENCE: 150
gacagggctt gataccgca                                                 19

<210> SEQ ID NO 151
<211> LENGTH: 38
<212> TYPE: DNA
<213> ORGANISM: Homo sapiens

<400> SEQUENCE: 151
gttttcccag tcacgacgat gctggctcac ttttgacc                            38

<210> SEQ ID NO 152
<211> LENGTH: 39
<212> TYPE: DNA
<213> ORGANISM: Homo sapiens

<400> SEQUENCE: 152
aggaaacagc tatgaccatg actggtgagt acagcagga                           39

<210> SEQ ID NO 153
<211> LENGTH: 21
<212> TYPE: DNA
<213> ORGANISM: Homo sapiens

<400> SEQUENCE: 153
ccagcctttg tgtaagtcta c                                              21

<210> SEQ ID NO 154
<211> LENGTH: 19
<212> TYPE: DNA
<213> ORGANISM: Homo sapiens
```

<400> SEQUENCE: 154
tctgggcaag tttggaagc                                               19

<210> SEQ ID NO 155
<211> LENGTH: 39
<212> TYPE: DNA
<213> ORGANISM: Homo sapiens

<400> SEQUENCE: 155
gttttcccag tcacgacgtc caaagcagac atcagcctc                         39

<210> SEQ ID NO 156
<211> LENGTH: 38
<212> TYPE: DNA
<213> ORGANISM: Homo sapiens

<400> SEQUENCE: 156
aggaaacagc tatgaccatg gaggaaaaga cgcagcca                          38

<210> SEQ ID NO 157
<211> LENGTH: 19
<212> TYPE: DNA
<213> ORGANISM: Homo sapiens

<400> SEQUENCE: 157
cgctttctgc ctgtgacat                                               19

<210> SEQ ID NO 158
<211> LENGTH: 20
<212> TYPE: DNA
<213> ORGANISM: Homo sapiens

<400> SEQUENCE: 158
ttctgtcctt cagccaatgc                                              20

<210> SEQ ID NO 159
<211> LENGTH: 37
<212> TYPE: DNA
<213> ORGANISM: Homo sapiens

<400> SEQUENCE: 159
gttttcccag tcacgacgtt agaggctggt gggtgac                           37

<210> SEQ ID NO 160
<211> LENGTH: 42
<212> TYPE: DNA
<213> ORGANISM: Homo sapiens

<400> SEQUENCE: 160
aggaaacagc tatgaccatc atctcaataa aaactggagt gc                     42

<210> SEQ ID NO 161
<211> LENGTH: 20
<212> TYPE: DNA
<213> ORGANISM: Homo sapiens

<400> SEQUENCE: 161
cacttgatgg gcgttctgag                                              20

<210> SEQ ID NO 162
<211> LENGTH: 20
<212> TYPE: DNA
<213> ORGANISM: Homo sapiens

<400> SEQUENCE: 162
ttctgtcctt cagccaatgc                                               20

<210> SEQ ID NO 163
<211> LENGTH: 38
<212> TYPE: DNA
<213> ORGANISM: Homo sapiens

<400> SEQUENCE: 163
gttttcccag tcacgacgtt ccagcggttt acacatca                           38

<210> SEQ ID NO 164
<211> LENGTH: 38
<212> TYPE: DNA
<213> ORGANISM: Homo sapiens

<400> SEQUENCE: 164
aggaaacagc tatgaccatt accccagtgt ccaccttg                           38

<210> SEQ ID NO 165
<211> LENGTH: 20
<212> TYPE: DNA
<213> ORGANISM: Homo sapiens

<400> SEQUENCE: 165
gggttctcca gccaaagact                                               20

<210> SEQ ID NO 166
<211> LENGTH: 19
<212> TYPE: DNA
<213> ORGANISM: Homo sapiens

<400> SEQUENCE: 166
ctgagtctcc tgcctctgc                                                19

<210> SEQ ID NO 167
<211> LENGTH: 38
<212> TYPE: DNA
<213> ORGANISM: Homo sapiens

<400> SEQUENCE: 167
gttttcccag tcacgacggg gttctccagc caaagact                           38

<210> SEQ ID NO 168
<211> LENGTH: 38
<212> TYPE: DNA
<213> ORGANISM: Homo sapiens

<400> SEQUENCE: 168
aggaaacagc tatgaccatg tggggctgga aggctctg                           38

<210> SEQ ID NO 169
<211> LENGTH: 37
<212> TYPE: DNA
<213> ORGANISM: Homo sapiens

<400> SEQUENCE: 169
gttttcccag tcacgacgaa gaggtaaggg gcacagc                            37

<210> SEQ ID NO 170
<211> LENGTH: 38
<212> TYPE: DNA

<213> ORGANISM: Homo sapiens

<400> SEQUENCE: 170
aggaaacagc tatgaccatc tgagtctcct gcctctgc         38

<210> SEQ ID NO 171
<211> LENGTH: 20
<212> TYPE: DNA
<213> ORGANISM: Homo sapiens

<400> SEQUENCE: 171
gctgagtgtt gagaccagga         20

<210> SEQ ID NO 172
<211> LENGTH: 19
<212> TYPE: DNA
<213> ORGANISM: Homo sapiens

<400> SEQUENCE: 172
agacaaacga cggctgctc         19

<210> SEQ ID NO 173
<211> LENGTH: 38
<212> TYPE: DNA
<213> ORGANISM: Homo sapiens

<400> SEQUENCE: 173
gttttcccag tcacgacgtt gagaccagga aacagcac         38

<210> SEQ ID NO 174
<211> LENGTH: 38
<212> TYPE: DNA
<213> ORGANISM: Homo sapiens

<400> SEQUENCE: 174
aggaaacagc tatgaccatg agaggatgtg ggcgacaa         38

<210> SEQ ID NO 175
<211> LENGTH: 19
<212> TYPE: DNA
<213> ORGANISM: Homo sapiens

<400> SEQUENCE: 175
gggagatggt gctggctac         19

<210> SEQ ID NO 176
<211> LENGTH: 21
<212> TYPE: DNA
<213> ORGANISM: Homo sapiens

<400> SEQUENCE: 176
cctggttagt gatgggtaga t         21

<210> SEQ ID NO 177
<211> LENGTH: 37
<212> TYPE: DNA
<213> ORGANISM: Homo sapiens

<400> SEQUENCE: 177
gttttcccag tcacgacgca gggtctgtgc cactgtc         37

<210> SEQ ID NO 178
<211> LENGTH: 40

```
<212> TYPE: DNA
<213> ORGANISM: Homo sapiens

<400> SEQUENCE: 178
aggaaacagc tatgaccatc tcagtgtgta gagtcctctc                          40

<210> SEQ ID NO 179
<211> LENGTH: 22
<212> TYPE: DNA
<213> ORGANISM: Homo sapiens

<400> SEQUENCE: 179
ttgattttga gagcatctgg ac                                             22

<210> SEQ ID NO 180
<211> LENGTH: 21
<212> TYPE: DNA
<213> ORGANISM: Homo sapiens

<400> SEQUENCE: 180
ctcggacact tagacccact g                                              21

<210> SEQ ID NO 181
<211> LENGTH: 37
<212> TYPE: DNA
<213> ORGANISM: Homo sapiens

<400> SEQUENCE: 181
gttttcccag tcacgacgtg catcccttcc agctcct                             37

<210> SEQ ID NO 182
<211> LENGTH: 41
<212> TYPE: DNA
<213> ORGANISM: Homo sapiens

<400> SEQUENCE: 182
aggaaacagc tatgaccatg acacacagcc ttctgagttc a                        41

<210> SEQ ID NO 183
<211> LENGTH: 37
<212> TYPE: DNA
<213> ORGANISM: Homo sapiens

<400> SEQUENCE: 183
gttttcccag tcacgacgcc acacagagga gccacag                             37

<210> SEQ ID NO 184
<211> LENGTH: 42
<212> TYPE: DNA
<213> ORGANISM: Homo sapiens

<400> SEQUENCE: 184
aggaaacagc tatgaccata ccagtcctaa gaggcatcta ta                       42

<210> SEQ ID NO 185
<211> LENGTH: 19
<212> TYPE: DNA
<213> ORGANISM: Homo sapiens

<400> SEQUENCE: 185
ccacacagag gagccacag                                                 19

<210> SEQ ID NO 186
```

```
<211> LENGTH: 20
<212> TYPE: DNA
<213> ORGANISM: Homo sapiens

<400> SEQUENCE: 186
ccagaggtgc tcactacgac                                              20

<210> SEQ ID NO 187
<211> LENGTH: 39
<212> TYPE: DNA
<213> ORGANISM: Homo sapiens

<400> SEQUENCE: 187
gttttcccag tcacgacgag gtcagagccc agtgaagat                         39

<210> SEQ ID NO 188
<211> LENGTH: 39
<212> TYPE: DNA
<213> ORGANISM: Homo sapiens

<400> SEQUENCE: 188
aggaaacagc tatgaccatc atctgcttgc ttccgtgtg                         39

<210> SEQ ID NO 189
<211> LENGTH: 39
<212> TYPE: DNA
<213> ORGANISM: Homo sapiens

<400> SEQUENCE: 189
gttttcccag tcacgacgtc aggataggtg gtatggagc                         39

<210> SEQ ID NO 190
<211> LENGTH: 40
<212> TYPE: DNA
<213> ORGANISM: Homo sapiens

<400> SEQUENCE: 190
aggaaacagc tatgaccatc ggacacttag acccactgat                        40

<210> SEQ ID NO 191
<211> LENGTH: 23
<212> TYPE: DNA
<213> ORGANISM: Homo sapiens

<400> SEQUENCE: 191
agactccgag tygaatgaaa atg                                          23

<210> SEQ ID NO 192
<211> LENGTH: 23
<212> TYPE: DNA
<213> ORGANISM: Homo sapiens

<400> SEQUENCE: 192
ggtgagggca crtttgggca gct                                          23

<210> SEQ ID NO 193
<211> LENGTH: 23
<212> TYPE: DNA
<213> ORGANISM: Homo sapiens

<400> SEQUENCE: 193
gcaccctggc trctgtgttt gtg                                          23
```

```
<210> SEQ ID NO 194
<211> LENGTH: 23
<212> TYPE: DNA
<213> ORGANISM: Homo sapiens

<400> SEQUENCE: 194
gtgtcccacc tgcacgcaga tca                                    23

<210> SEQ ID NO 195
<211> LENGTH: 24
<212> TYPE: DNA
<213> ORGANISM: Homo sapiens

<400> SEQUENCE: 195
gtgtcccacc tggcacgcag atca                                   24

<210> SEQ ID NO 196
<211> LENGTH: 23
<212> TYPE: DNA
<213> ORGANISM: Homo sapiens

<400> SEQUENCE: 196
aagccgcttc aycctttgct ggt                                    23

<210> SEQ ID NO 197
<211> LENGTH: 24
<212> TYPE: DNA
<213> ORGANISM: Homo sapiens

<400> SEQUENCE: 197
gctgttgcga acrtgtgatt tgga                                   24

<210> SEQ ID NO 198
<211> LENGTH: 22
<212> TYPE: DNA
<213> ORGANISM: Homo sapiens

<400> SEQUENCE: 198
gaggcttggg stcccacata ag                                     22

<210> SEQ ID NO 199
<211> LENGTH: 23
<212> TYPE: DNA
<213> ORGANISM: Homo sapiens

<400> SEQUENCE: 199
cctggcacag cygcgggcca gga                                    23

<210> SEQ ID NO 200
<211> LENGTH: 23
<212> TYPE: DNA
<213> ORGANISM: Homo sapiens

<400> SEQUENCE: 200
aatccagcaa artgattccc tgc                                    23

<210> SEQ ID NO 201
<211> LENGTH: 21
<212> TYPE: DNA
<213> ORGANISM: Homo sapiens

<400> SEQUENCE: 201 taaatgttttt ytcattctta g                                     21
```

```
<210> SEQ ID NO 202
<211> LENGTH: 23
<212> TYPE: DNA
<213> ORGANISM: Homo sapiens

<400> SEQUENCE: 202
ttgctgttgt gyggttttct tgt                                    23

<210> SEQ ID NO 203
<211> LENGTH: 24
<212> TYPE: DNA
<213> ORGANISM: Homo sapiens

<400> SEQUENCE: 203
ggttttcttg attcagcagt taca                                   24

<210> SEQ ID NO 204
<211> LENGTH: 27
<212> TYPE: DNA
<213> ORGANISM: Homo sapiens

<400> SEQUENCE: 204
ggttttcttg atgattcagc agttaca                                27

<210> SEQ ID NO 205
<211> LENGTH: 23
<212> TYPE: DNA
<213> ORGANISM: Homo sapiens

<400> SEQUENCE: 205
gtgtctcaga cyggcccctt gtc                                    23

<210> SEQ ID NO 206
<211> LENGTH: 23
<212> TYPE: DNA
<213> ORGANISM: Homo sapiens

<400> SEQUENCE: 206
tgccatcttg awctaatgga atc                                    23

<210> SEQ ID NO 207
<211> LENGTH: 23
<212> TYPE: DNA
<213> ORGANISM: Homo sapiens

<400> SEQUENCE: 207
cttctctctc tycctgcagg gat                                    23

<210> SEQ ID NO 208
<211> LENGTH: 23
<212> TYPE: DNA
<213> ORGANISM: Homo sapiens

<400> SEQUENCE: 208
catcaagggc aygtttactt ttt                                    23

<210> SEQ ID NO 209
<211> LENGTH: 23
<212> TYPE: DNA
<213> ORGANISM: Homo sapiens

<400> SEQUENCE: 209
cagccttgcc csctgggctg ttg                                    23
```

<210> SEQ ID NO 210
<211> LENGTH: 350
<212> TYPE: DNA
<213> ORGANISM: Homo sapiens
<220> FEATURE:
<221> NAME/KEY: CDS
<222> LOCATION: (51)..(293)

<400> SEQUENCE: 210

```
cgcgggcgta ggtgaccggc ggctttctca gttttggtgg agacgggcgc atg tgg       56
                                                        Met Trp
                                                          1 gcg ctt tgc tcg ctg ctg cgg tcc gcg gcc gga cgc acc atg tcg cag      104
Ala Leu Cys Ser Leu Leu Arg Ser Ala Ala Gly Arg Thr Met Ser Gln
      5                  10                  15 gga cgc acc ata tcg cag gca ccc gcc cgc cgc gag cgg ccg cgc aag      152
Gly Arg Thr Ile Ser Gln Ala Pro Ala Arg Arg Glu Arg Pro Arg Lys
 20                  25                  30 gac ccg ctg cgg cac ctg cgc acg cga gag aag cgc gga ccg tcg ggg      200
Asp Pro Leu Arg His Leu Arg Thr Arg Glu Lys Arg Gly Pro Ser Gly
 35                  40                  45                  50 tgc tcc ggc ggc cca aac acc gtg tac ctg cag gtg gtg gca gcg ggt      248
Cys Ser Gly Gly Pro Asn Thr Val Tyr Leu Gln Val Val Ala Ala Gly
              55                  60                  65 agc cgg gac tcg ggc gcc gcg ctc tac gtc ttc tcc gag ttc aac          293
Ser Arg Asp Ser Gly Ala Ala Leu Tyr Val Phe Ser Glu Phe Asn
         70                  75                  80 cggtcagtca acgagccacg ccccgtcccg ctgggccctc agtgcggcgc agcctct       350
```

<210> SEQ ID NO 211
<211> LENGTH: 81
<212> TYPE: PRT
<213> ORGANISM: Homo sapiens

<400> SEQUENCE: 211

```
Met Trp Ala Leu Cys Ser Leu Leu Arg Ser Ala Ala Gly Arg Thr Met
  1               5                  10                  15

Ser Gln Gly Arg Thr Ile Ser Gln Ala Pro Ala Arg Arg Glu Arg Pro
             20                  25                  30

Arg Lys Asp Pro Leu Arg His Leu Arg Thr Arg Glu Lys Arg Gly Pro
         35                  40                  45

Ser Gly Cys Ser Gly Gly Pro Asn Thr Val Tyr Leu Gln Val Val Ala
     50                  55                  60

Ala Gly Ser Arg Asp Ser Gly Ala Ala Leu Tyr Val Phe Ser Glu Phe
 65                  70                  75                  80

Asn
```

<210> SEQ ID NO 212
<211> LENGTH: 326
<212> TYPE: DNA
<213> ORGANISM: Mus musculus
<220> FEATURE:
<221> NAME/KEY: CDS
<222> LOCATION: (51)..(269)

<400> SEQUENCE: 212

```
tggcggcgtg aggggtctgg ctgccttgtc agcctggtgt ggtcgggtgc atg tgg       56
                                                        Met Trp
                                                          1 gcg ctc cgc tca ctg ttg cgt ccc ctt ggc ctg cgc acc atg tcg cag      104
```

-continued

```
Ala Leu Arg Ser Leu Leu Arg Pro Leu Gly Leu Arg Thr Met Ser Gln
         5                   10                  15 ggt tcg gct cgt cgg ccg cgg cca ccc aag gac cca ctg cga cac ctg     152
Gly Ser Ala Arg Arg Pro Arg Pro Pro Lys Asp Pro Leu Arg His Leu
        20                  25                  30 cgt acg cgg gag aag cgc ggc ccg ggt ccc ggg ggc ccg aac acc gtg     200
Arg Thr Arg Glu Lys Arg Gly Pro Gly Pro Gly Gly Pro Asn Thr Val
 35                  40                  45                  50 tac ctg cag gtg gtg gcg gcg ggc ggc cgg gac gcg ggg gct gct ctc     248
Tyr Leu Gln Val Val Ala Ala Gly Gly Arg Asp Ala Gly Ala Ala Leu
                55                  60                  65 tat gtc ttc tcg gaa tac aac aggtcagagt gggccgacag ccctggggga        299
Tyr Val Phe Ser Glu Tyr Asn
                70 ttggccccag cgccacgtgc tcgggag                                       326
```

<210> SEQ ID NO 213
<211> LENGTH: 73
<212> TYPE: PRT
<213> ORGANISM: Mus musculus

<400> SEQUENCE: 213

```
Met Trp Ala Leu Arg Ser Leu Leu Arg Pro Leu Gly Leu Arg Thr Met
 1               5                   10                  15

Ser Gln Gly Ser Ala Arg Arg Pro Arg Pro Pro Lys Asp Pro Leu Arg
                20                  25                  30

His Leu Arg Thr Arg Glu Lys Arg Gly Pro Gly Pro Gly Gly Pro Asn
            35                  40                  45

Thr Val Tyr Leu Gln Val Val Ala Ala Gly Gly Arg Asp Ala Gly Ala
        50                  55                  60

Ala Leu Tyr Val Phe Ser Glu Tyr Asn
 65                  70
```